(12) United States Patent
Leung et al.

(10) Patent No.: US 7,052,891 B2
(45) Date of Patent: May 30, 2006

(54) HUMAN LYSOPHOSHATIDIC ACID ACYLTRANSFERASE GAMMA-1 POLYPEPTIDE

(75) Inventors: David W. Leung, Mercer Island, WA (US); Daniel Adourel, Woodinville, WA (US); David Hollenback, Seattle, WA (US)

(73) Assignee: Cell Therapeutics Inc., Seattle, WA (US)

( * ) Notice: Subject to any disclaimer, the term of this patent is extended or adjusted under 35 U.S.C. 154(b) by 27 days.

(21) Appl. No.: 10/667,494

(22) Filed: Sep. 23, 2003

(65) Prior Publication Data

US 2004/0043465 A1   Mar. 4, 2004

Related U.S. Application Data

(60) Division of application No. 09/970,989, filed on Oct. 5, 2001, now Pat. No. 6,670,143, which is a division of application No. 09/215,252, filed on Dec. 18, 1998, now Pat. No. 6,300,487, which is a continuation-in-part of application No. 08/618,651, filed on Mar. 19, 1996, now Pat. No. 6,136,964.

(51) Int. Cl.
G12N 9/10       (2006.01)
(52) U.S. Cl. ..................................... 435/193
(58) Field of Classification Search ............... 435/193
See application file for complete search history.

(56) References Cited

U.S. PATENT DOCUMENTS

| 5,288,721 | A | * | 2/1994 | Klein et al. ............ 514/263.23 |
| 5,470,878 | A | * | 11/1995 | Michnick et al. ........... 514/558 |
| 5,888,793 | A |   | 3/1999 | Hillman et al. |
| 6,001,620 | A |   | 12/1999 | Hillman et al. |
| 2003/0049771 | A1 | * | 3/2003 | Baker et al. ............... 435/69.1 |
| 2003/0073174 | A1 |   | 4/2003 | Baker et al. |
| 2003/0082711 | A1 |   | 5/2003 | Baker et al. |

OTHER PUBLICATIONS

Brown et al., "Isolation and characterisation of a maize cDNA that complements a 1-acyl sn-glcerol-3-phosphate acyltransferase mutant of *Escherichia coli* and encodes a protein which has similarities to other acyltransferases," *Plant Molecular Biology*, Oct. 1994, pp. 211-223, vol. 26, No. 1, Kluwer Academic Publishers, Belgium.

Brown et al., "Identification of cDNA that encodes a 1-acyl-sn-glycerol-3-phosphate acyltransferase from *Limnanthes douglasii*," *Plant Molecular Biology*, Oct. 1995, pp. 267-278, vol. 29, No. 2, Kluwer Academic Publishers, Belguim.

Coleman et al., "Characterization of the *Escherichia coli* gene for 1-acyl-sn-glycerol-3-phosphate acyltransferase (*plsC*)," *Mol. Gen. Genet.*, 1992, pp. 295-303, vol. 232, No. 2, Springer-Verlag.

Hanke et al., "A plant acyltransferase involved in triacylglycerol biosynthesis complements an *Escherichia coli* sn-1-acylglycerol-3-phosphate acyltransferase mutant," *Eur. J. Biochem.*, Sep. 1995, pp. 806-810, vol. 232, No. 3, Springer International.

Knutzon et al., "Cloning of a Cocunut Endosperm cDNA Encoding a 1-Acyl-sn-Glycerol-3-Phosphate Acyltransferase That Accepts Medium-Chain-Length Substrates," *Plant Physiol.*, Nov. 1995, pp. 999-1006, vol. 109, No. 3.

Lassner et al., "Lysophosphatidic Acid Acyltransferase from Meadowfoam mediates Insertion of Erucic Acid at the sn-2 Position of Triacylglycerol in Transgenic Rapeseed Oil," *Plant Physiol.*, Dec. 1995, pp. 1389-1394, vol. 109, No. 4.

Nagiec et al., "A Suppressor Gene That Enables *Saccharomyces cerevisiae* to Grow without Making Sphingolipids Encodes a Protein That Resembles an *Escherichia coli* Fatty Acyltransferase," *The Journal of Biological Chemistry*, Oct. 15, 1993, pp. 22156-22163, vol. 268, No. 29, The American Society for Biochemistry and Molecular Biology, Inc., USA.

West et al., "Cloning and Expressing of Two Human Lysophosphatidic Acid Acyltransferase cDNAs That Enhance Cytokine-Induced Signaling Responses in Cells," *DNA and Cell Biology*, Jun. 1997, vol. 16, No. 6, Mary Ann Liebert, Inc., USA.

Swartley et al., "Membrane glycerophospholipid biosynthesis in *Neisseria meningitidis* and *Neisseria gonorrhoeae*: identification, characterization, and mutagenesis of a lysophosphatidic acid acyltransferase," *Molecular Microbiology*, Nov. 1995, pp. 401-412, vol. 18, No. 3, Blackwell Science Ltd.

* cited by examiner

*Primary Examiner*—David J. Steadman
(74) *Attorney, Agent, or Firm*—Foley & Lardner LLP

(57) ABSTRACT

Polypeptides are obtained, for example, via expression of encoding cDNA sequences, that have the activity of the enzyme lysophosphatidic acid acyltransferase (LPAAT), also known as 1-acyl sn-glycerol-3-phosphate acyltransferase.

1 Claim, 33 Drawing Sheets

Figure 1A

```
  1 GGAAGTCAGCAGGCGTTGGGGAGGGTGGCGGGGAATAGCGGCGGCAGC
 51 AGCCCCAGCCCTCAGAGACAGAAAGGGAGGGAGGAGGGTGCTGG
101 GGGGACAGCCCCCACCATTCCTACCGCTATGGGCCAACCTCCCACTCC
151 CACCTCCCCTCCATCGGCCGGGCTAGGACACCCCAAATCCGTCGCCC
201 CCTTGGCACCGACACCCCGACAGAGACAGAGACACCATCCGCCACCA
251 CCGCTGCCGCCAGCCTGGCTGGGGAGGGCCAGCCCCCCAGCCCCCTAC
301 CCCTCTGAGGTGGCCAGA ATG GAT TTG TGG CCA GGG GCA TGG
                     Met Asp Leu Trp Pro Gly Ala Trp
343 ATG CTG CTG CTG CTC TTC CTG CTG CTC TTC C
    Met Leu Leu Leu Leu Phe Leu Leu Leu Phe L
                   10                       20
380 TG CTG CCC ACC CTG TGG TTC TGC AGC CCC AGT GCC AAG
    eu Leu Pro Thr Leu Trp Phe Cys Ser Pro Ser Ala Lys
                                30
```

Figure 1B

```
418  TAC TTC TTC AAG ATG GCC TTC TAC AAT GGC TGG ATC C
     Tyr Phe Phe Lys Met Ala Phe Tyr Asn Gly Trp Ile L
                          40

455  TC TTC CTG GCT GTG CTC GCC ATC CCT GTG TGT GCC GTG
     eu Phe Leu Ala Val Leu Ala Ile Pro Val Cys Ala Val
                          50

493  CGA GGA CGC AAC GTC GAG AAC ATG AAG ATC TTG CGT C
     Arg Gly Arg Asn Val Glu Asn Met Lys Ile Leu Arg L
                    60                          70

530  TA ATG CTG CTC CAC ATC AAA TAC CTG TAC GGG ATC CGA
     eu Met Leu Leu His Ile Lys Tyr Leu Tyr Gly Ile Arg
                                      80
```

Figure 1C

```
568  GTG GAG GTG CGA GGG GCT CAC CAC TTC CCT CCC TCG C
     Val Glu Val Arg Gly Ala His His Phe Pro Pro Ser G
                                90

605  AG CCC TAT GTT GTT GTC TCC AAC CAC CAG AGC TCT CTC
     ln Pro Tyr Val Val Val Ser Asn His Gln Ser Ser Leu
                              100

643  GAT CTG CTT GGG ATG ATG GAG GTA CTG CCA GGC CGC T
     Asp Leu Leu Gly Met Met Glu Val Leu Pro Gly Arg C
                            110                    120

680  GT GTG CCC ATT GCC AAG CGC GAG CTA CTG TGG GCT GGC
     ys Val Pro Ile Ala Lys Arg Glu Leu Leu Trp Ala Gly
                                130
```

Figure 1D

```
718 TCT GCC GGG CTG GCC TGC TGG CTG GCA GGA GTC ATC T
    Ser Ala Gly Leu Ala Cys Trp Leu Ala Gly Val Ile P
                            140

755 TC ATC GAC CGG AAG CGC ACG GGG GAT GCC ATC AGT GTC
    he Ile Asp Arg Lys Arg Thr Gly Asp Ala Ile Ser Val
                            150

793 ATG TCT GAG GTC GCC CAG ACC CTG CTC ACC CAG GAC G
    Met Ser Glu Val Ala Gln Thr Leu Leu Thr Gln Asp V
                            160

830 TG AGG GTC TGG GTG TTT CCT GAG GGA ACG AGA AAC CAC
    al Arg Val Trp Val Phe Pro Glu Gly Thr Arg Asn His
                            180
```

Figure 1E

```
868  AAT GGC TCC ATG CTG CCC TTC AAA CGT GGC GCC TTC C
     Asn Gly Ser Met Leu Pro Phe Lys Arg Gly Ala Phe H
                              190

905  AT CTT GCA GTG CAG GCC CAG GTT CCC ATT GTC CCC ATA
     is Leu Ala Val Gln Ala Gln Val Pro Ile Val Pro Ile
                                200

943  GTC ATG TCC TCC TAC CAA GAC TTC TAC TGC AAG AAG G
     Val Met Ser Ser Tyr Gln Asp Phe Tyr Cys Lys Lys G
                     210                            220

980  AG CGT CGC TTC ACC TCG GGA CAA TGT CAG GTG CGG GTG
     lu Arg Arg Phe Thr Ser Gly Gln Cys Gln Val Arg Val
                              230
```

Figure 1F

```
1018 CTG CCC CCA GTG CCC ACG GAA GGG CTG ACA CCA GAT G
     Leu Pro Pro Val Pro Thr Glu Gly Leu Thr Pro Asp A
                                240

1055 AC GTC CCA GCT CTG GCT GAC AGA GTC CGG CAC TCC ATG
     sp Val Pro Ala Leu Ala Asp Arg Val Arg His Ser Met
                        250

1093 CTC ACT GTT TTC CGG GAA ATC TCC ACT GAT GGC CGG G
     Leu Thr Val Phe Arg Glu Ile Ser Thr Asp Gly Arg G
                        260

1130 GT GGT GGT GAC TAT CTG AAG AAG CCT GGG GGC GGT GGG
     ly Gly Gly Asp Tyr Leu Lys Lys Pro Gly Gly Gly 280
                                            270

1168 TGA ACCCTGGCTCTGAGCTCTCCTCCTCCCATCTGTCCCCATCTTCCTCCC

1216 CACACCTACCCACCCAGTGGGCCCTGAAGCAGGGCCAAACCCTCTTCCTT

1266 GTCTCCCCTCTCCCCACTTATTCTCCTCTTTGAATCTTCAACTTCTGAA
```

Figure 1G

```
1316  GTGAATGTGGATACAGCGCCACTCCTGCCCCCTCTTGGCCCCATCCATGG
1366  ACTCTTGCCTCGGTGCAGTTTCCACTCTTGACCCCACTTCCTACTGTCT
1416  TGTCTGTGGGACAGTTGCCTCCCCCTCATCTCCAGTGACTCAGCCTACAC
1466  AAGGGAGGGAACATTCCATCCCCAGTGAGTCTCTTCCTATGTGGTCTT
1516  CTCTACCCCTCTACCCCCACATTGGCCAGTGGACTCATCCATTCTTTGGA
1566  ACAAATCCCCCCACTCCAAAGTCCATGGATTCAATGGACTCATCCATT
1616  TGTGAGGAGGACTTCTCGCCCTCTGGCTGGAAGCTGATACCTGAAGCACT
1666  CCCAGGCTCATCCTGGGAGCTTTCCTCAGCACCTTCACCTTCCCTCCCAG
1716  TGTAGCCCTCCGTCAGTGGGGCTGGACCCTTTCTAATTCAGAGGTCTCAT
1766  GCCTGCCCTTGCCCAGATGCCCAGGGTCGTGCACTCTCTGGATACCAGT
1816  TCAGTCTCCACATTTCTGGTTTTCTGTCCCCATAGTACAGTTCTTCAGTG
1866  GACATGACCCCACCCAGCCCCTGCAGCCCTGACCATCTCACCAGAC
1916  ACAAGGGGAAGAAGCAGACATCAGGTGCTGCACTCACTTCTGCCCCTGG
1966  GGAGTTGGGGAAAGGAACGAACCCTGGCTGGAGGGGATAGGAGGGCTTTT
```

Figure 1H

2016 AATTTATTTCTTTTCTGTTGAGGCTTCCCCCTCTCTGAGCCCAGTTTTCA
2066 TTTCTTCCCTGGTGGCATTAGCCACTCCCTGCCTCTCACTCCAGACCTGTT
2116 CCCACAACTGGGGAGGTAGGCTGGGAGCAAAAGGAGAGGGTGGGACCCAG
2166 TTTTGCGTGGTTGGTTTTTATTAATTATCTGGATAACAGCAAAAAACTG
2216 AAAATAAAGAGAGAGAGAAAAAAAAA

Figure 2A

```
                    10         20         30         40         50
Human LPAAT    1 MDLWPGAWM- ----LLLLLF LL-LLFLLPT LWFCSPSAKY F-----FKMA
Yeast LPAAT    1 MSV-IGRFLY YLRSVL-VVL AL-AG----- ----C----- ---------G
E.coli LPAAT   1 M--------- ------LYIF RL-IITVIYS ILVCVFGSIY ----------
Maize LPAAT    1 MAI------- ---PLVLVVL PLGLLFLLSG LIVNAIQAVL FVTIRPFSKS 60         70         80         90        100
Human LPAAT   51 FYNGWILFLA VLAIPVCAVR GRNVENMKIL RLMLLHIKYL -YGIRVEVRG
Yeast LPAAT   51 FY-------G VIASILCTLI GKQHLAQWIT ARCFYHVMKL MLGLDV---K
E.coli LPAAT  51 --------- --------- CLFS PRNPKHVATF GHMFGRLAPL -FGLKVECRK
Maize LPAAT   51 FYRRINRFLA EL-------- ---------- -------L-- WLQLVWVDW WAGVKVQLHA 110        120        130        140        150
Human LPAAT  101 AHHF-PPSQ- -PYVVVSNHQ SSLDLLGMME VL--PGRC-- -VPI-AKREL
Yeast LPAAT  101 VVGE-ENLAK KPYIMIANHQ STLDIFMLGR IF--PPGCT- ---VTAKKSL
E.coli LPAAT 101 PTDA-ESYG- -NAIYIANHQ NNYDMVTASN IVQ-PP---- TVTV-GKKSL
Maize LPAAT  101 DEETYRSMGK EHALIISNHR SDIDWL-IGW ILAQRSGCLG STLAVMKKSS 160        170        180        190        200
Human LPAAT  151 LWAGSAGLAC W--LAGVIF_ IDRKRTGDAI SVMSEVAQTL LTQDVRVWV-
Yeast LPAAT  151 KYVPFLG--- WFMALSGTYF LDRSKRQEAI DTLNKGLENV KKNKRALWV-
E.coli LPAAT 151 LWIPFFGQLY W--LTGNLL_ IDRNNNRTKAH GTIAEVVNHF KKRRISIWM-
Maize LPAAT  151 KFLPVIGWSM WF--AEYLF_ LERS-WAKDE KTLKWGLQRL KDFPRPFWLA 210        220        230        240        250
Human LPAAT  201 -FPEGTRNHN GS-------- ---------- MLPFKRGAFH LAVQAQVPIV
Yeast LPAAT  201 -FPEGTRSYT SEL------- ---------- MLPFKKGAFH LAQQGKIPIV
E.coli LPAAT 201 -FPEGTRSRG RGL------- ----T----- -LPFKTGAFH AAIAAGVPII
Maize LPAAT  201 LFVEGTRFTP AKLLAAQEYA ASQGLPAPRN VLIPRTKGFV SAVSIMRDFV
```

Figure 2 B

```
                   260        270        280        290        300
Human LPAAT   251  PIVMSSYQDF YCKKERRFTS GQCQVRVLPP VPTEGLTPDD VPALADR---
Yeast LPAAT   251  PVVVSNTSTL VSPKYGVFNR GCMIVRILKP ISTENLTKDK IGEFAEK---
E.coli LPAAT  251  PVCVSTISNK I--NLNRLHN GLVIVEMLPP IDVSQYGKDQ VRELAAH---
Maize LPAAT   251  PAIYDTT--V IVPKDSPQPT MLRILKGQSS VIHVRMKRHA MSEMPKSDED 310        320        330        340        350
Human LPAAT   301  ---------- VRHSMLTV-F REISTDGRGG GDYLKKPGGG G*........
Yeast LPAAT   301  ---------- VRDQMVDT-L KEIGYSPAIN DTTLPPQ--- ..........
E.coli LPAAT  301  ---------- CRSIMEQK-I AELDKEVAE- ----REAAGK V*........
Maize LPAAT   301  VSKWCKDIFV AKDALLDKHL ATGTFDEEIR PIGRPVKSLL VTLFWSCLLL 360        370        380        390        400
Human LPAAT   351  .......... .......... .......... .......... ..........
Yeast LPAAT   351  --AIEY---A AL-------Q HDKKVNKKIK NEPVPSVSIS NDVNTHNEGS
E.coli LPAAT  351  .......... .......... .......... .......... ..........
Maize LPAAT   351  FGAIEFFKWT QLLSTWRGVA FTAAGMALVT GVMHVFIMFS QA------ERS 410        420        430        440        450
Human LPAAT   401  .......... .......... .......... .......... ..........
Yeast LPAAT   401  S-------V KKMH*...... .......... .......... ..........
E.coli LPAAT  401  .......... .......... .......... .......... ..........
Maize LPAAT   401  SSARAARNRV KKE*....... .......... .......... ..........
```

Figure 3 A

```
         10         20         30         40         50         60
GGAGCGAGCT GGCGGCGCCG TCGGGCGCCG GGCCGGGCCA TGGAGCTGTG GCCGTGTCTG 70         80         90        100        110        120
GCCGCGGCGC TGCTGTTGCT GCTGCTGCTG GTGCAGCTGA GCCGGCGGGC CGAGTTCTAC 130        140        150        160        170        180
GCCAAGGTCG CCCTGTACTG CGCGCTGTGC TTCACGGTGT CCGCCGTGGC CTCGCTCGTC 190        200        210        220        230        240
TGCCTGCTGT GCCACGGGCG CCGGACGGTG GAGAACATGA GCATCATCGG CTGGTTCGTG 250        260        270        280        290        300
CGAAGCTTCA AGTACTTTTA CGGGCTCCGC TTCGAGGTGC GGGACCCGCG CAGGCTGCAG 310        320        330        340        350        360
GAGGCCCGTC CCTGTGTCAT CGTCTCCAAC CACCAGAGCA TCCTGGACAT GATGGGCCTC 370        380        390        400        410        420
ATGGAGGTCC TTCCGGAGCG CTGCGTGCAG ATCGCCAAGC GGGAGCTGCT CTTCCTGGGG 430        440        450        460        470        480
CCCGTGGGCC TCATCATGTA CCTCGGGGGC GTCTTCTTCA TCAACCGGCA GCGCTCTAGC 490        500        510        520        530        540
ACTGCCATGA CAGTGATGGC CGACCTGGGC GAGGCCATGG TCAGGGAGAA CCTCAAAGTG
```

Figure 3B

```
550        560        570        580        590        600
TGGATCTATC CCGAGGGTAC TCGCAACGAC AATGGGGACC TGCTGCCTTT TAAGAAGGGC 610        620        630        640        650        660
GCCTTCTACC TGGCAGTCCA GGCACAGGTG CCCATCGTCC CCGTGGTGTA CTCTTCCTTC 670        680        690        700        710        720
TCCTCCTTCT ACAACACCAA GAAGAAGTTC TTCACTTCAG GAACAGTCAC AGTGCAGGTG 730        740        750        760        770        780
CTGGAAGCCA TCCCCACCAG CGGCCTCACT GCGGCGGACG TCCCTGCGCT CGTGGACACC 790        800        810        820        830        840
TGCCACCGGG CCATGAGGAC CACCTTCCTC CACATCTCCA AGACCCCCA GGAGAACGGG 850        860        870        880        890        900
GCCACTGCGG GGTCTGGCGT GCAGCCGGCC CAGTAGCCCA GACCACGGCA GGGCATGACC 910        920        930        940        950        960
TGGGGAGGGC AGGTGGAAGC CGATGGCTGG AGGATGGGCA GAGGGGACTC CTCCCGGCTT 970        980        990        1000       1010       1020
CCAAATACCA CTCTGTCCGG CTCCCCCAGC TCTCACTCAG CCCGGGAAGC AGGAAGCCCC 1030       1040       1050       1060       1070       1080
TTCTGTCACT GGTCTCAGAC ACAGGCCCCT GGTGTCCCCT GCAGGGGGCT CAGCTGGACC
```

Figure 3C

```
       1090       1100       1110       1120       1130       1140
CTCCCCGGGC TCGAGGGCAG GGACTCGCGC CCACGGCACC TCTGGGNGCT GGGNTGATAA
       1150       1160       1170       1180       1190       1200
AGATGAGGCT TGCGGCTGTG GCCCGCTGGT GGGCTGAGCC ACAAGGCCCC CGATGGCCCA
       1210       1220       1230       1240       1250       1260
GGAGCAGATG GGAGGACCCC GAGGCCAGGA GTCCCAGACT CACGCACCCT GGGCCACAGG
       1270       1280       1290       1300       1310       1320
GAGCCGGGAA TCGGGGCCTG CTGCTCCTGC TGGCCTGAAG AATCTGTGGG GTCAGCACTG
       1330       1340       1350       1360       1370       1380
TACTCCGTTG CTGTTTTTTT ATAAACACAC TCTTGGAAAA AAAAAAAAAA AAAAAAAAAA
       1390       1400       1410       1420       1430       1440
AAA........ .......... .......... .......... .......... ..........
```

Figure 4A

```
        10        20        30        40        50
GGAGCGAGCTGGCGGCCCGTCGGGGGCCGCGGGGCCATGGAGCTGTGGCCG
                                   Met Glu Leu Trp Pro 60         70         80         90
TGT CTG GCC GCG GCG CTG CTG TTG CTG CTG CTG GTG CAG CTG
Cys Leu Ala Ala Ala Leu Leu Leu Leu Leu Leu Val Gln Leu
                    10                              20

100        110        120        130        140
AGC CGC GCG GCC GAG TTC TAC GCC AAG GTC GCC CTG TAC TGC GCG
Ser Arg Ala Ala Glu Phe Tyr Ala Lys Val Ala Leu Tyr Cys Ala
                         30

150        160        170        180
CTG TGC TTC ACG GTG TCC GCC GTG GCC TCG CTC GTC TGC CTG CTG
Leu Cys Phe Thr Val Ser Ala Val Ala Ser Leu Val Cys Leu Leu
                    40                              50

190        200        210        220        230
TGC CAC GGC GGC CGG ACG GTG GAG AAC ATG AGC ATC ATC GGC TGG
Cys His Gly Gly Arg Thr Val Glu Asn Met Ser Ile Ile Gly Trp
                              60
```

Figure 4B

```
240                 250                 260                 270
TTC GTG CGA AGC TTC AAG TAC TTT TAC GGG CTC CGC TTC GAG GTG
Phe Val Arg Ser Phe Lys Tyr Phe Tyr Gly Leu Arg Phe Glu Val
                                                          80

280                 290                 300                 310                 320
CGG GAC CCG CGC AGG CTG CAG GAG GCC CGT CCC TGT GTC ATC GTC
Arg Asp Pro Arg Arg Leu Gln Glu Ala Arg Pro Cys Val Ile Val
                                              90

330                 340                 350                 360
TCC AAC CAC CAG AGC ATC CTG GAC ATG ATG GGC CTC ATG GAG GTC
Ser Asn His Gln Ser Ile Leu Asp Met Met Gly Leu Met Glu Val
                    100                                 110

370                 380                 390                 400                 410
CTT CCG GAG CGC TGC GTG CAG ATC GCC AAG CGG GAG CTG CTC TTC
Leu Pro Glu Arg Cys Val Gln Ile Ala Lys Arg Glu Leu Leu Phe
                                        120

420                 430                 440                 450
CTG GGG CCC GTG GGC CTC ATC ATG TAC CTC GGG GGC GTC TTC TTC
Leu Gly Pro Val Gly Leu Ile Met Tyr Leu Gly Gly Val Phe Phe
                        130                                 140

460                 470                 480                 490                 500
ATC AAC CGG CAG CGC TCT AGC ACT GCC ATG ACA GTG ATG GCC GAC
Ile Asn Arg Gln Arg Ser Ser Thr Ala Met Thr Val Met Ala Asp
                                            150
```

Figure 4C

```
       510            520            530            540
CTG GGC GAG CGC ATG GTC AGG GAG AAC CTC AAA GTG TGG ATC TAT
Leu Gly Glu Arg Met Val Arg Glu Asn Leu Lys Val Trp Ile Tyr
                         160                               170

550            560            570            580            590
CCC GAG GGT ACT CGC AAC GAC AAT GGG GAC CTG CTG CCT TTT AAG
Pro Glu Gly Thr Arg Asn Asp Asn Gly Asp Leu Leu Pro Phe Lys
                             180

600            610            620            630
AAG GGC GCC TTC TAC CTG GCA GTC CAG GCA CAG GTG CCC ATC GTC
Lys Gly Ala Phe Tyr Leu Ala Val Gln Ala Gln Val Pro Ile Val
                     190                                   200

640            650            660            670            680
CCC GTG GTG TAC TCT TCC TTC TAC AAC ACC AAG AAG
Pro Val Val Tyr Ser Ser Phe Ser Ser Phe Tyr Asn Thr Lys Lys
                                         210

690            700            710            720
AAG TTC TTC ACT TCA GGA ACA GTC ACA GTG CAG GTG CTG GAA GCC
Lys Phe Phe Thr Ser Gly Thr Val Thr Val Gln Val Leu Glu Ala
                         220                               230
```

Figure 4D

```
730            740            750            760            770
ATC CCC ACC AGC GGC CTC ACT GCG GCG GAC GTC CCT GCG CTC GTG
Ile Pro Thr Ser Gly Leu Thr Ala Ala Asp Val Pro Ala Leu Val
                                    240

780            790            800            810
GAC ACC TGC CAC CGG GCC ATG AGG ACC ACC TTC CTC CAC ATC TCC
Asp Thr Cys His Arg Ala Met Arg Thr Thr Phe Leu His Ile Ser
                        250                                260

820            830            840            850            860
AAG ACC CCC CAG GAG AAC GGG GCC ACT GCG GGG TCT GGC GTG CAG
Lys Thr Pro Gln Glu Asn Gly Ala Thr Ala Gly Ser Gly Val Gln
                                                        270

870            880            890            900            910            920
CCG GCC CAG TAG CCCAGACCACGGGCAGGGCATGACCTGGGAGGGCAGGTGGAAGC
Pro Ala Gln ***

930
    940        950        960        970        980
CGATGGCTGGAGGATGGGCAGAGGGACTCCTCCCGGCTTCCAAATACCACTCTGTCCGG 990
   1000       1010       1020       1030       1040
CTCCCCCAGCTCTCACTCAGCCCGGGAAGCAGGAAGCCCCTTCTGTCACTGGTCTCAGAC
       1050       1060       1070       1080       1090       1100
ACAGGCCCCTGTGTCCCTGCAGGGGCTCAGCTGACCCTCCCCGGGCTGAGGGCAG
```

Figure 4E

```
1110  1120      1130      1140      1150      1160
      GGACTCGCGCCCACGGCACCTCTGGGNGCTGGGNTGATAAAGATGAGGCTTGCGGCTGTG 1170  1180      1190      1200      1210      1220
      GCCCGCTGGTGGGCTGAGCCACAAGGCCCCCGATGCCCAGGAGCAGATGGGAGGACCCC 1230  1240      1250      1260      1270      1280
      GAGGCCAGGAGTCCCAGACTCACGCACCCTGGGCCACAGGGAGCCGGGAATCGGGGCCTG 1290  1300      1310      1320      1330      1340
      CTGCTCCTGCTCCTGGCCTGAAGAATCTGTGGGGTCAGCACTGTACTCCGTTGCTGTTTTTT 1350  1360      1370      1380
      ATAAACACACTCTTGGAAAAAAAAAAAAAAAAAAAA
```

Figure 5 A

Alignment of LPAAT Sequences.

```
                 10         20         30         40         50
Human LPAAT-β    1  ---------- ---------- ---------- ----MEL WPC-----LA AALLLLLLV
Human LPAAT-α    1  ---------- ---------- ---------- ------MDL WPGAWLLLL IFLLLFLLP
Yeast LPAAT      1  ---------- ---------- ---------- -------MSV --IGRFLYYL RSVLWLALA
E.coli LPAAT     1  ---------- ---------- ---------- ---------- ---------
H.influenzae     1  ---------- ---------- ---------- ---------- ---------
S.typhimuriu     1  ---------- ---------- ---------- ---------- ---------
L.douglassi      1  MAKIRTSS-L RNR------- -------RQLKP AVAATAD-D DKDGVFM---
C. nucifera      1  MDASGASSFL RGRCLESCFK ASFGMSQPKD AAGQPSRRPA DADDFFIVDD 60         70         80         90         100
Human LPAAT-β    51 QL---SPAAE FYAKVAL-YC ALCFTVSAVA SLVCLLCHGG RTVENM-SII
Human LPAAT-α    51 TLWFCSBSAK YFFKMAF-YN GWIFLAVLA IPVCAV--RG RNVENM-KIL
Yeast LPAAT      51 G-------CG FY-------- --GVIA SILCTLIGKQ HLAQWI-TAR
E.coli LPAAT     51 ------MLYI FRLITVIYS ILVC---VFG SIYCLFSPRN PKHV----ATF
H.influenzae     51 ------MLKL LRIFLMLICC ILIC---VLG TIYSFIRFKN PSNV----GIV
S.typhimuriu     51 ------MLYI FRLIVTVIYS ILVC---VFG SIYCLFSPRN PKHV----ATF
L.douglassi      51 ------LLSC FKIFVCFAFT VVLITAVAWG LIWLLILPWP YMRIRLGNY
C. nucifera      51 DRWITVILSV VRLAACFL-- SMVTTVWN MIMILLPWP YARRQGNY
```

Figure 5 B

```
                                110                 120          130          140             150
Human LPAAT-β    101 GWFVRSFKY- ---FYGLRFEV RDPRRLQEAR PCVIVSNHQS ILDMGIMEV
Human LPAAT-α    101 RLMIHIKY-- ---LYGIRVEV RGAHHFPSQ  PYVVSNHQS  SLDILGMMEV
Yeast LPAAT      101 CFY-HMKL-  ---M.GLDVKV VGEENLAK-K PYIMLANHQS TLDIFMLGRI
E.coli LPAAT     101 GHMFGRL--  ---APLFGLKVEC RKPTDAESYG NAIYIANHQN NYDMVTASNI
H.influenzae     101 ARWFGRL-FT YPLFGLKVEH RIPQDQKQIS RAIYIGNHQN NYDMVTISYM
S.typhimuriu     101 GHMFGRL-FT APLFGLKVEC RKPADAENYG NAIYIANHQN NYDMVTAANI
L.douglassi      101 GHIIGLV--- IWYGIPIKI  QGSEHIKKRA IFTYISNHAS PIDAFFVML
C. nucifera      101 GHVTGRMLFT MMILGNPIII EGSEFSNTRA I--YICNHAS LVDIFILMWL 160                 170          180          190             200
Human LPAAT-β    151 LPERCVQIAK RELLFLGPV- -GLIMYLGGV FFINRQRSST AMT---VMADL
Human LPAAT-α    151 LPGRCVPIAK RELLWAGSA- --GLACWLAGV IFIDRKRIGD AIS---VMSEV
Yeast LPAAT      151 FPPGCTVTAK KSLKVPFL-  -GWFMALSGT YFLDRSKRQE AID---TING
E.coli LPAAT     151 VQPPTVTVGK KSLLWIPFF- -GQLYWLTGN LLIDRNNRTK AHG---TIAEV
H.influenzae     151 VQPRTVSVGK KSLIWIPFFF TGILYWVTGN IFIDRENRTK AHN---TMSQL
S.typhimuriu     151 VQPPTVTVGK KSLLWIPFFF TGQLYWLTGN LLIDRNNRAK AHS---TIAAV
L.douglassi      151 APIGTVGVAK KEVIWYPILG Q--LYTLAH  IRIDRSNPAA AIQSFTMKEA
C. nucifera      151 IPKGTVTIAK KEIIWYPLFG QFTLYVLANH QRIDRSNPSA AIES--IKEV
```

Figure 5C

|  | | 210 | 220 | 230 | 240 | 250 |
|---|---|---|---|---|---|---|
| Human LPAAT-β | 201 | GERMRENLK | VWIYPEGTRN | DNGDL—LPF | KKGAFYL—A | VQAQVPIVPV |
| Human LPAAT-α | 201 | AQILIQDVR | VWVFPEGTRN | HNGSM—LPF | KRGAFHL—A | VQAQVPIVPI |
| Yeast LPAAT | 201 | LENVKKNKRA | LWVFPEGTRS | YTSELIMLPF | KKGAFHL—A | QQKIPIVPV |
| E.coli LPAAT | 201 | VNHFKKRRIS | IWMFPEGTRS | RGRGL—LPF | KTGAF—HAA | IAAGVPIIPV |
| H.influenzae | 201 | ARRINDNLS | IWMFPEGTRN | RGRGL—LPF | KTGAFTFHAA | ISAGVPIIPV |
| S.typhimuriu | 201 | VNHFKKRRIS | IWMFPEGTRS | RGRGL—LPF | KTGAFTFHAA | IAAGVPIIPV |
| L.douglassi | 201 | VRVTEKNLS | LIMFPEGTRS | GDGRL—LPF | KKGFVHL—A | LQSHLPIVPM |
| C. nucifera | 201 | ARAWKNLS | LIIFPEGTRS | KTGRL—LPF | KKGFIHFTIA | LQIRLPIVPM |

|  | | 260 | 270 | 280 | 290 | 300 |
|---|---|---|---|---|---|---|
| Human LPAAT-β | 251 | VYSSFSS—F | YNIKKFFTS | GIVTVQLFA | IPTSGLTAAD | VPALVDTCR |
| Human LPAAT-α | 251 | VMSSYQD—F | YCKKERFETS | GQQQVRVLPP | VPTEGLTPDD | VPALADRVRH |
| Yeast LPAAT | 251 | VVSNIST—L | VSPKYGVFNR | GMIVRILKP | ISTENLTKDK | IGEFAEKVRD |
| E.coli LPAAT | 251 | CVSTTS—— | NKINLNRIHN | GLVIVEMLPP | IDVSQGKDQ | VRELAAHCR- |
| H.influenzae | 251 | VCSSTH—— | NKINLNRWDN | GKVICEIMDP | IDVSGYTKDN | VRDLAAYCHF |
| S.typhimuriu | 251 | CVSNIS—— | NKVNLNRINN | GLVIVEMLPP | VDVSEGKDQ | VRELAAHCRF |
| L.douglassi | 251 | ILTGTHLAWF | TRKGIFRVRP | VPITVKYLPP | INTDDWTVK | IDDYKMHD |
| C. nucifera | 251 | VLTGTHLAW- | -RKNSLRVRP | APITVKYFSP | IKIDDWEEK | INHYVEMHF |

Figure 5D

```
                    310        320        330        340        350
Human LPAAT-β   301 AMRTIFIHIS KIPQENGATA GGVQPAQ*-- ---------- ----------
Human LPAAT-α   301 SMITVFREIS TDGRGGDYL KKPGGGG*-- ---------- ----------
Yeast LPAAT     301 QMVDILKEIG YSPAINDTIL PPQAIEYAAL QHDKKVNKKI KNEPVPSVSI
E.coli LPAAT    301 -SIMEQKIAE LDKEVA--ER EAAGKV*--- ---------- ----------
H.influenzae    301 TLMEKRIAE  LDEEIA---- ---KGN*---  ---------- ----------
S.typhimuriu    301 TALMEQKIAE LDKEVA--ER EATGKV*--- ---------- ----------
L.douglassi     301 IYVRNLPASQ KPIGS--TNR --S-K*---- ---------- ----------
C. nucifera     301 TALYVDHLPE SQKPLVSKGR DASGRSNS*- ---------- ----------

360        370        380        390
Human LPAAT-β   351 ---------- ---------- ---------- ----------...........
Human LPAAT-α   351 ---------- ---------- ---------- ----------...........
Yeast LPAAT     351 SNDMNTHNEG SSVKKMH*.. .......... ...................
E.coli LPAAT    351 ---------- ---------- ---------- ----------...........
H.influenzae    351 ---------- ---------- ---------- ----------...........
S.typhimuriu    351 ---------- ---------- ---------- ----------...........
L.douglassi     351 ---------- ---------- ---------- ----------...........
C. nucifera     351 ---------- ---------- ---------- ----------...........
```

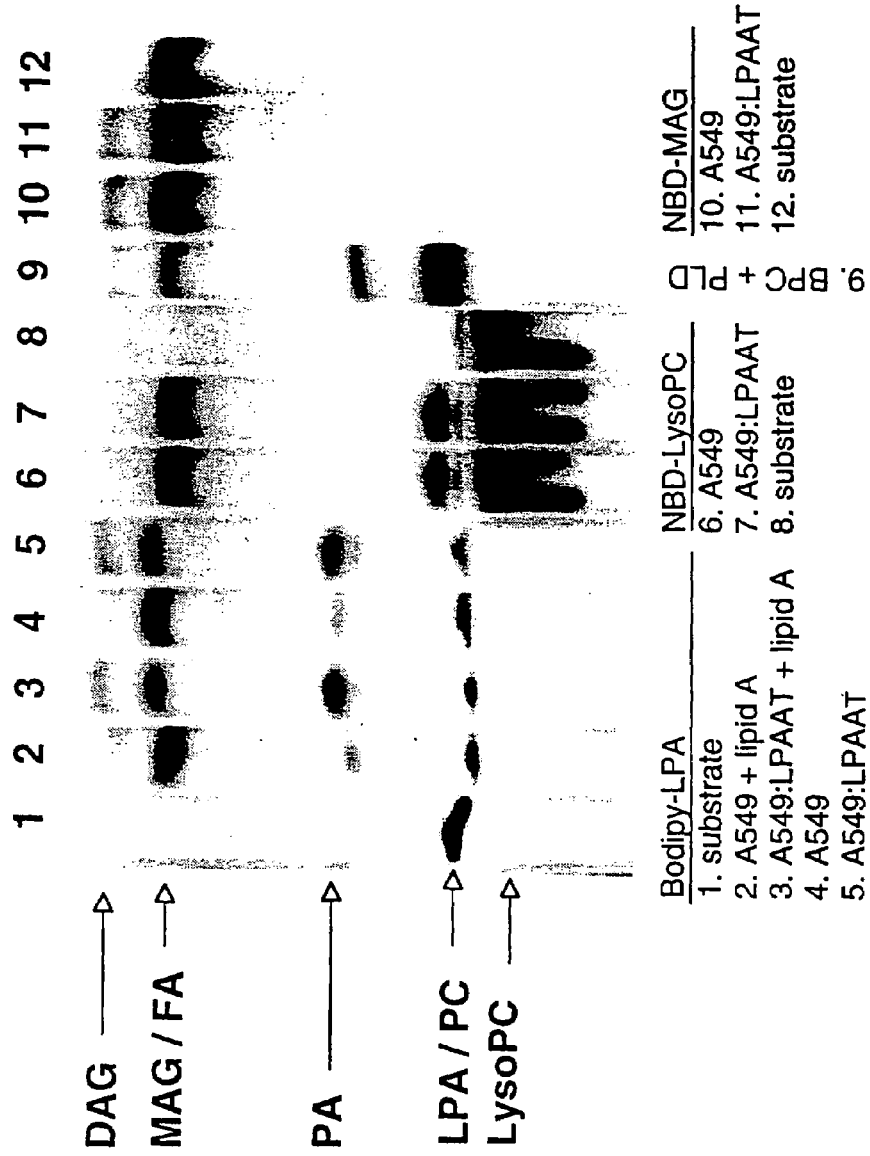

Figure 9 A

```
TCTATGAAACCAACATACATGGCGTTTGCATCACAGTTGGAGTCAGATGTGAGCCCGGAG       60
GGCAGGTGTCTGGCTTGTCCACCCGGAAGCCCTGAGGGCAGCTGTTCCCACTGGCTCTGC      120
TGACCTTGTGCCTTGGACGGCTGTCCTCAGCGAGGGCCGTGCACCCGCTCCTGAGCAGC       180
GCC ATG GGC CTG CTG GCC TTC CTG AAG ACC CAG TTC GTG CTG CAC       225
    Met Gly Leu Leu Ala Phe Leu Lys Thr Gln Phe Val Leu His
                    5                    10
CTG CTG GTC GGC TTT GTC TTC GTG GTG AGT GGT CTG GTC ATC AAC       270
Leu Leu Val Gly Phe Val Phe Val Val Ser Gly Leu Val Ile Asn
 15              20                  25
TTC GTC CAG CTG TGC ACG CTG GCG CTC TGG CCG GTC AGC AAG CAG       315
Phe Val Gln Leu Cys Thr Leu Ala Leu Trp Pro Val Ser Lys Gln
 30              35                  40
CTC TAC CGC CGC CTC AAC TGC CGC CTC GCA TAC TCA CTC TGG AGC       360
Leu Tyr Arg Arg Leu Asn Cys Arg Leu Ala Tyr Ser Leu Trp Ser
 45              50                  55
CAA CTG GTC ATG CTG CTG GAG TGG TGG TCC TGC ACG GAG TGT ACA       405
Gln Leu Val Met Leu Leu Glu Trp Trp Ser Cys Thr Glu Cys Thr
 60              65                  70
CTG TTC ACG GAC CAG GCC ACG GTA GAG CGC TTT GGG AAG GAG CAC       450
Leu Phe Thr Asp Gln Ala Thr Val Glu Arg Phe Gly Lys Glu His
 75              80                  85
GCA GTC ATC ATC CTC AAC CAC AAC TTC GAG ATC GAC TTC CTC TGT       495
Ala Val Ile Ile Leu Asn His Asn Phe Glu Ile Asp Phe Leu Cys
 90              95                  100
GGG TGG ACC ATG TGT GAG CGC TTC GGA GTG CTG GGG AGC TCC AAG       540
Gly Trp Thr Met Cys Glu Arg Phe Gly Val Leu Gly Ser Ser Lys
105              110                 115
GTC CTC GCT AAG AAG GAG CTG CTC TAC GTG CCC CTC ATC GGC TGG       585
Val Leu Ala Lys Lys Glu Leu Leu Tyr Val Pro Leu Ile Gly Trp
120              125                 130
ACG TGG TAC TTT CTG GAG ATT GTG TTC TGC AAG CGG AAG TGG GAG       630
Thr Trp Tyr Phe Leu Glu Ile Val Phe Cys Lys Arg Lys Trp Glu
135              140                 145
GAG GAC CGG GAC ACC GTG GTC GAA GGG CTG AGG CGC CTG TCG GAC       675
Glu Asp Arg Asp Thr Val Val Glu Gly Leu Arg Arg Leu Ser Asp
150              155                 160
TAC CCC GAG TAC ATG TGG TTT CTC CTG TAC TGC GAG GGG ACG CGC       720
Tyr Pro Glu Tyr Met Trp Phe Leu Leu Tyr Cys Glu Gly Thr Arg
165              170                 175
TTC ACG GAG ACC AAG CAC CGC GTT AGC ATG GAG GTG GCG GCT GCT       765
Phe Thr Glu Thr Lys His Arg Val Ser Met Glu Val Ala Ala Ala
180              185                 190
AAG GGG CTT CCT GTC CTC AAG TAC CAC CTG CTG CCG CGG ACC AAG       810
Lys Gly Leu Pro Val Leu Lys Tyr His Leu Leu Pro Arg Thr Lys
195              200                 205
GGC TTC ACC ACC GCA GTC AAG TGC CTC CGG GGG ACA GTC GCA GCT       855
Gly Phe Thr Thr Ala Val Lys Cys Leu Arg Gly Thr Val Ala Ala
210              215                 220
GTC TAT GAT GTA ACC CTG AAC TTC AGA GGA AAC AAG AAC CCG TCC       900
Val Tyr Asp Val Thr Leu Asn Phe Arg Gly Asn Lys Asn Pro Ser
225              230                 235
CTG CTG GGG ATC CTC TAC GGG AAG AAG TAC GAG GCC GAC ATG TGC       945
Leu Leu Gly Ile Leu Tyr Gly Lys Lys Tyr Glu Ala Asp Met Cys
240              245                 250
GTG AGG AGA TTT CCT CTG GAA GAC ATC CCG CTG GAT GAA AAG GAA       990
Val Arg Arg Phe Pro Leu Glu Asp Ile Pro Leu Asp Glu Lys Glu
255              260                 265
GCA GCT CAG TGG CTT CAT AAA CTG TAC CAG GAG AAG GAC GCG CTC      1035
```

Figure 9 B

```
        Ala Ala Gln Trp Leu His Lys Leu Tyr Gln Glu Lys Asp Ala Leu
        270             275             280
        CAG GAG ATA TAT AAT CAG AAG GGC ATG TTT CCA GGG GAG CAG TTT    1080
        Gln Glu Ile Tyr Asn Gln Lys Gly Met Phe Pro Gly Glu Gln Phe
        285             290             295
        AAG CCT GCC CGG AGG CCG TGG ACC CTC CTG AAC TTC CTG TCC TGG    1125
        Lys Pro Ala Arg Arg Pro Trp Thr Leu Leu Asn Phe Leu Ser Trp
        300             305             310
        GCC ACC ATT CTC CTG TCT CCC CTC TTC AGT TTT GTC TTG GGC GTC    1170
        Ala Thr Ile Leu Leu Ser Pro Leu Phe Ser Phe Val Leu Gly Val
        315             320             325
        TTT GCC AGC GGA TCA CCT CTC CTG ATC CTG ACT TTC TTG GGG TTT    1215
        Phe Ala Ser Gly Ser Pro Leu Leu Ile Leu Thr Phe Leu Gly Phe
        330             335             340
        GTG GGA GCA GCT TCC TTT GGA GTT CGC AGA CTG ATA GGA GTA ACT    1260
        Val Gly Ala Ala Ser Phe Gly Val Arg Arg Leu Ile Gly Val Thr
        345             350             355
        GAG ATA GAA AAA GGC TCC AGC TAC GGA AAC CAA GAG TTT AAG AAA    1305
        Glu Ile Glu Lys Gly Ser Ser Tyr Gly Asn Gln Glu Phe Lys Lys
        360             365             370
        AAG GAA TAA TTAATGGCTGTGACTGAACACACGCGGCCCTGACGGTGGTATCCAGTT   1362
        Lys Glu ***
        AACTCAAAACCAACACACAGAGTGCAGGAAAAGACAATTAGAAACTATTTTTCTTATTAA   1422
        CTGGTGACTAATATTAACAAAACTTGAGCCAAGAGTAAAGAATTCAGAAGGCCTGTCAGG   1482
        TGAAGTCTTCAGCCTCCCACAGCGCAGGGTCCCAGCATCTCCACGCGCGCCCGTGGGAGG   1542
        TGGGTCCGGCCGGAGAGGCCTCCCGCGGACGCCGTCTCTCCAGAACTCCGCTTCCAAGAG   1602
        GGACCTTTGGCTGCTTTCTCTCCTTAAACTTAGATCAAATTTTAAAAAAAAAAAAAAA    1660
```

Figure 10A

```
CACGCTGGCGCTCTGGCCGGTCAGCAAGCAGCTCTACCGCCGCCTCAACTGCCGCCTCGCC    61
TACTCACTCTGGAGCCTAGCACAAAACTAGAAGCAACCCAAGCACCTGTCACTGGAGACT    121
AATTATGCGGCACCCATACAGGGACCCTCTGCGGCCATCATGGAGAGCCTTCATCTTGCC    181
CGTACAGTTTTAAGCGAAAAAGGAAGTATACAACAAAGTCCATAACTGGTC ATG CTG    238
                                                    Met Leu
```

| Codons | # |
|---|---|
| CTG GAG TGG TGG TCC TGC ACG GAG TGT ACA CTG TTC ACG GAC CAG<br>Leu Glu Trp Trp Ser Cys Thr Glu Cys Thr Leu Phe Thr Asp Gln<br>    5              10             15 | 283 |
| GCC ACG GTA GAG CGC TTT GGG AAG GAG CAC GCA GTC ATC ATC CTC<br>Ala Thr Val Glu Arg Phe Gly Lys Glu His Ala Val Ile Ile Leu<br>   20              25             30 | 328 |
| AAC CAC AAC TTC GAG ATC GAC TTC CTC TGT GGG TGG ACC ATG TGT<br>Asn His Asn Phe Glu Ile Asp Phe Leu Cys Gly Trp Thr Met Cys<br>   35              40             45 | 373 |
| GAG CGC TTC GGA GTG CTG GGG AGC TCC AAG GTC CTC GCT AAG AAG<br>Glu Arg Phe Gly Val Leu Gly Ser Ser Lys Val Leu Ala Lys Lys<br>   50              55             60 | 418 |
| GAG CTG CTC TAC GTG CCC CTC ATC GGC TGG ACG TGG TAC TTT CTG<br>Glu Leu Leu Tyr Val Pro Leu Ile Gly Trp Thr Trp Tyr Phe Leu<br>   65              70             75 | 463 |
| GAG ATT GTG TTC TGC AAG CGG AAG TGG GAG GAG GAC CGG GAC ACC<br>Glu Ile Val Phe Cys Lys Arg Lys Trp Glu Glu Asp Arg Asp Thr<br>   80              85             90 | 508 |
| GTG GTC GAA GGG CTG AGG CGC CTG TCG GAC TAC CCC GAG TAC ATG<br>Val Val Glu Gly Leu Arg Arg Leu Ser Asp Tyr Pro Glu Tyr Met<br>   95             100            105 | 553 |
| TGG TTT CTC CTG TAC TGC GAG GGG ACG CGC TTC ACG GAG ACC AAG<br>Trp Phe Leu Leu Tyr Cys Glu Gly Thr Arg Phe Thr Glu Thr Lys<br>  110             115            120 | 598 |
| CAC CGC GTT AGC ATG GAG GTG GCG GCT GCT AAG GGG CTT CCT GTC<br>His Arg Val Ser Met Glu Val Ala Ala Ala Lys Gly Leu Pro Val<br>  125             130            135 | 643 |
| CTC AAG TAC CAC CTG CTG CCG CGG ACC AAG GGC TTC ACC ACC GCA<br>Leu Lys Tyr His Leu Leu Pro Arg Thr Lys Gly Phe Thr Thr Ala<br>  140             145            150 | 688 |
| GTC AAG TGC CTC CGG GGG ACA GTC GCA GCT GTC TAT GAT GTA ACC<br>Val Lys Cys Leu Arg Gly Thr Val Ala Ala Val Tyr Asp Val Thr<br>  155             160            165 | 733 |
| CTG AAC TTC AGA GGA AAC AAG AAC CCG TCC CTG CTG GGG ATC CTC<br>Leu Asn Phe Arg Gly Asn Lys Asn Pro Ser Leu Leu Gly Ile Leu<br>  170             175            180 | 778 |
| TAC GGG AAG AAG TAC GAG GCG GAC ATG TGC GTG AGG AGA TTT CCT<br>Tyr Gly Lys Lys Tyr Glu Ala Asp Met Cys Val Arg Arg Phe Pro<br>  185             190            195 | 823 |
| CTG GAA GAC ATC CCG CTG GAT GAA AAG GAA GCA GCT CAG TGG CTT<br>Leu Glu Asp Ile Pro Leu Asp Glu Lys Glu Ala Ala Gln Trp Leu<br>  200             205            210 | 868 |
| CAT AAA CTG TAC CAG GAG AAG GAC GCG CTC CAG GAG ATA TAT AAT<br>His Lys Leu Tyr Gln Glu Lys Asp Ala Leu Gln Glu Ile Tyr Asn<br>  215             220            225 | 913 |
| CAG AAG GGC ATG TTT CCA GGG GAG CAG TTT AAG CCT GCC CGG AGG<br>Gln Lys Gly Met Phe Pro Gly Glu Gln Phe Lys Pro Ala Arg Arg<br>  230             235            240 | 958 |
| CCG TGG ACC CTC CTG AAC TTC CTG TCC TGG GCC ACC ATT CTC CTG<br>Pro Trp Thr Leu Leu Asn Phe Leu Ser Trp Ala Thr Ile Leu Leu<br>  245             250            255 | 1003 |
| TCT CCC CTC TTC AGT TTT GTC TTG GGC GTC TTT GCC AGC GGA TCA<br>Ser Pro Leu Phe Ser Phe Val Leu Gly Val Phe Ala Ser Gly Ser | 1048 |

Figure 10 B

|  | 260 |  |  |  |  | 265 |  |  |  |  | 270 |  |  |  |
|---|---|---|---|---|---|---|---|---|---|---|---|---|---|---|
| CCT | CTC | CTG | ATC | CTG | ACT | TTC | TTG | GGG | TTT | GTG | GGA | GCA | GCT | TCC | 1093
| Pro | Leu | Leu | Ile | Leu | Thr | Phe | Leu | Gly | Phe | Val | Gly | Ala | Ala | Ser |
|  | 275 |  |  |  |  | 280 |  |  |  |  | 285 |  |  |  |
| TTT | GGA | GTT | CGC | AGA | CTG | ATA | GGA | GTA | ACT | GAG | ATA | GAA | AAA | GGC | 1138
| Phe | Gly | Val | Arg | Arg | Leu | Ile | Gly | Val | Thr | Glu | Ile | Glu | Lys | Gly |
|  | 290 |  |  |  |  | 295 |  |  |  |  | 300 |  |  |  |
| TCC | AGC | TAC | GGA | AAC | CAA | GAG | TTT | AAG | AAA | AAG | GAA | TAA | TTAATGGC | | 1185
| Ser | Ser | Tyr | Gly | Asn | Gln | Glu | Phe | Lys | Lys | Lys | Glu | *** |  |  |
|  | 305 |  |  |  |  | 310 |  |  |  |  |  |  |  |  |

```
TGTGACTGAACACACGCGGCCCTGACGGTGGTATCCAGTTAACTCAAAACCAACACACAG     1245
AGTGCAGGAAAAGACAATTAGAAACTATTTTTCTTATTAACTGGTGACTAATATTAACAA     1305
AACTTGAGCCAAGAGTAAAGAATTCAGAAGGCCTGTCAGGTGAAGTCTTCAGCCTCCCAC     1365
AGCGCAGGGTCCCAGCATCTCCACGCGCGCCCGTGGGAGGTGGGTCCGGCCGGAGAGGCC     1425
TCCCGCGGACGCCGTCTCTCCAGAACTCCGCTTCCAAGAGGGACCTTTGGCTGCTTTCTC     1485
TCCTTAAACTTAGATCAAATTTTAAAAAAAAAAAAAAA                          1523
```

Figure 11A

```
TGAACCCAGCCGGCTCCATCTCAGCTTCTGGTTTCTAAGTCCATGTGCCAAAGGCTGCCAG    61
GAAGGAGACGCCTTCCTGAGTCCTGGATCTTTCTTCCTTCTGGAAATCTTTGACTGTGGG    121
TAGTTATTTATTTCTGAATAAGAGCGTCCACGCATC ATG GAC CTC GCG GGA CTG    175
                                     Met Asp Leu Ala Gly Leu
                                                         5
CTG AAG TCT CAG TTC CTG TGC CAC CTG GTC TTC TGC TAC GTC TTT     220
Leu Lys Ser Gln Phe Leu Cys His Leu Val Phe Cys Tyr Val Phe
         10                  15                  20
ATT GCC TCA GGG CTA ATC ATC AAC ACC ATT CAG CTC TTC ACT CTC     265
Ile Ala Ser Gly Leu Ile Ile Asn Thr Ile Gln Leu Phe Thr Leu
         25                  30                  35
CTC CTC TGG CCC ATT AAC AAG CAG CTC TTC CGG AAG ATC AAC TGC     310
Leu Leu Trp Pro Ile Asn Lys Gln Leu Phe Arg Lys Ile Asn Cys
         40                  45                  50
AGA CTG TCC TAT TGC ATC TCA AGC CAG CTG GTG ATG CTG CTG GAG     355
Arg Leu Ser Tyr Cys Ile Ser Ser Gln Leu Val Met Leu Leu Glu
         55                  60                  65
TGG TGG TCG GGC ACG GAA TGC ACC ATC TTC ACG GAC CCG CGC GCC     400
Trp Trp Ser Gly Thr Glu Cys Thr Ile Phe Thr Asp Pro Arg Ala
         70                  75                  80
TAC CTC AAG TAT GGG AAG GAA AAT GCC ATC GTG GTT CTC AAC CAC     445
Tyr Leu Lys Tyr Gly Lys Glu Asn Ala Ile Val Val Leu Asn His
         85                  90                  95
AAG TTT GAA ATT GAC TTT CTG TGT GGC TGG AGC CTG TCC GAA CGC     490
Lys Phe Glu Ile Asp Phe Leu Cys Gly Trp Ser Leu Ser Glu Arg
         100                 105                 110
TTT GGG CTG TTA GGG GGC TCC AAG GTC CTG GCC AAG AAA GAG CTG     535
Phe Gly Leu Leu Gly Gly Ser Lys Val Leu Ala Lys Lys Glu Leu
         115                 120                 125
GCC TAT GTC CCA ATT ATC GGC TGG ATG TGG TAC TTC ACC GAG ATG     580
Ala Tyr Val Pro Ile Ile Gly Trp Met Trp Tyr Phe Thr Glu Met
         130                 135                 140
GTC TTC TGT TCG CGC AAG TGG GAG CAG GAT CGC AAG ACG GTT GCC     625
Val Phe Cys Ser Arg Lys Trp Glu Gln Asp Arg Lys Thr Val Ala
         145                 150                 155
ACC AGT TTG CAG CAC CTC CGG GAC TAC CCC GAG AAG TAT TTT TTC     670
Thr Ser Leu Gln His Leu Arg Asp Tyr Pro Glu Lys Tyr Phe Phe
         160                 165                 170
CTG ATT CAC TGT GAG GGC ACA CGG TTC ACG GAG AAG AAG CAT GAG     715
Leu Ile His Cys Glu Gly Thr Arg Phe Thr Glu Lys Lys His Glu
         175                 180                 185
ATC AGC ATG CAG GTG GCC CGG GCC AAG GGG CTG CCT CGC CTC AAG     760
Ile Ser Met Gln Val Ala Arg Ala Lys Gly Leu Pro Arg Leu Lys
         190                 195                 200
CAT CAC CTG TTG CCA CGA ACC AAG GGC TTC GCC ATC ACC GTG AGG     805
His His Leu Leu Pro Arg Thr Lys Gly Phe Ala Ile Thr Val Arg
         205                 210                 215
AGC TTG AGA AAT GTA GTT TCA GCT GTA TAT GAC TGT ACA CTC AAT     850
Ser Leu Arg Asn Val Val Ser Ala Val Tyr Asp Cys Thr Leu Asn
         220                 225                 230
TTC AGA AAT AAT GAA AAT CCA ACA CTG CTG GGA GTC CTA AAC GGA     895
Phe Arg Asn Asn Glu Asn Pro Thr Leu Leu Gly Val Leu Asn Gly
         235                 240                 245
AAG AAA TAC CAT GCA GAT TTG TAT GTT AGG AGG ATC CCA CTG GAA     940
Lys Lys Tyr His Ala Asp Leu Tyr Val Arg Arg Ile Pro Leu Glu
         250                 255                 260
GAC ATC CCT GAA GAC GAT GAC GAG TGC TCG GCC TGG CTG CAC AAG     985
Asp Ile Pro Glu Asp Asp Asp Glu Cys Ser Ala Trp Leu His Lys
         265                 270                 275
```

Figure 11B

```
CTC TAC CAG GAG AAG GAT GCC TTT CAG GAG GAG TAC TAC AGG ACG      1030
Leu Tyr Gln Glu Lys Asp Ala Phe Gln Glu Glu Tyr Tyr Arg Thr
            280             285                 290
GGC ACC TTC CCA GAG ACG CCC ATG GTG CCC CCC CGG CGG CCC TGG      1075
Gly Thr Phe Pro Glu Thr Pro Met Val Pro Pro Arg Arg Pro Trp
            295             300                 305
ACC CTC GTG AAC TGG CTG TTT TGG GCC TCG CTG GTG CTC TAC CCT      1120
Thr Leu Val Asn Trp Leu Phe Trp Ala Ser Leu Val Leu Tyr Pro
            310             315                 320
TTC TTC CAG TTC CTG GTC AGC ATG ATC AGG AGC GGG TCT TCC CTG      1165
Phe Phe Gln Phe Leu Val Ser Met Ile Arg Ser Gly Ser Ser Leu
            325             330                 335
ACG CTG GCC AGC TTC ATC CTC GTC TTC TTT GTG GCC TCC GTG GGA      1210
Thr Leu Ala Ser Phe Ile Leu Val Phe Phe Val Ala Ser Val Gly
            340             345                 350
GTT CGA TGG ATG ATT GGT GTG ACG GAA ATT GAC AAG GGC TCT GCC      1255
Val Arg Trp Met Ile Gly Val Thr Glu Ile Asp Lys Gly Ser Ala      366
            355             360                 365
TAC GGC AAC TCT GAC AGC AAG CAG AAA CTG AAT GAC TGA CTCAGGG      1301
Tyr Gly Asn Ser Asp Ser Lys Gln Lys Leu Asn Asp ***
            370             375
AGGTGTCACCATCCGAAGGGAACCTTGGGGAACTGGTGGCCTCTGCATATCCTCCTTAGT    1361
GGGACACGGTGACAAAGGCTGGGTGAGCCCCTGCTGGGCACGGCGGAAGTCACGACCTC     1421
CCAGCCAGGGAGTCTGGTCTCAAGGCCGGATGGGGAGGAAGATGTTTTGTAATCTTTTTT    1481
TCCCCATGTGCTTTAGTGGGCTTTGGTTTTCTTTTTGTGCGAGTGTGTGTGAGAATGGCT    1541
GTGTGGTGAGTGTGAACTTTGTTCTGTGATCATAGAAAGGGTATTTTAGGCTGCAGGGGA    1601
GGGCAGGGCTGGGGACCGAAGGGGACAAGTTCCCCTTTCATCCTTTGGTGCTGAGTTTTC    1661
TGTAACCCTTGGTTGCCAGAGATAAAGTGAAAAGTGCTTTAGGTGAGATGACTAAATTAT    1721
GCCTCCAAGAAAAAAAATTAAAGTGCTTTTCTGGGTCAAAAAAAAAAAAAAA            1774
```

Figure 12

```
                   10         20         30         40         50
LPAAT-γ1    MGLLAFLKTQ FVLHLLVGFV FVVSGLVINF VQ-LCTLALW PVSKQLYRRL
LPAAT-γ2    ---------- ---------- ---------- ---------- ----------
LPAAT-δ     MDLAGLLKSQ FLCHLVFCYV FIASGLIINT IQ-LFTLLLW PINKQLFRKI 60         70         80         90        100
LPAAT-γ1    NCRLAYSLWS QLVMLLEWWS CTECTLFTDQ ATVERFGKEH AVIILNHNFE
LPAAT-γ2    ---------- ---MLLEWWS CTECTLFTDQ ATVERFGKEH AVIILNHNFE
LPAAT-δ     NCRLSYCISS QLVMLLEWWS GTECTIFTDP RAYLKYGKEN AIVVLNHKFE 110        120        130        140        150
LPAAT-γ1    IDFLCGWTMC ERFGVLGSSK VLAKKELLYV PLIGWTWYFL EIVFCKRKWE
LPAAT-γ2    IDFLCGWTMC ERFGVLGSSK VLAKKELLYV PLIGWTWYFL EIVFCKRKWE
LPAAT-δ     IDFLCGWSES ERFGLLGGSK VLAKKELAYV PIIGWMWYFT EMVFCSRKWE 160        170        180        190        200
LPAAT-γ1    EDRDTVVEGL RRLSDYPEYM WFLLYCEGTR FTETKHRVSM EVAAAKGLPV
LPAAT-γ2    EDRDTVVEGL RRLSDYPEYM WFLLYCEGTR FTETKHRVSM EVAAAKGLPV
LPAAT-δ     QDRKTVATSL QHLRDYPEKY FFLIHCEGTR FTEKKHEISM QVARAKGLPR 210        220        230        240        250
LPAAT-γ1    LKYHLLPRTK GFTTAVKCLR GTVAAVYDVT LNF-RGNKNP SLLGILYGKK
LPAAT-γ2    LKYHLLPRTK GFTTAVKCLR GTVAAVYDVT LNF-RGNKNP SLLGILYGKK
LPAAT-δ     LKHHLLPRTK GFAITVRSLR NVVSAVYDCT LNF-RNNENP ILLGVLNGKK 260        270        280        290        300
LPAAT-γ1    YEADMCVRRF PLEDIPLDEK EAAQWLHKLY QEKDALQEIY NQKGMFPGEQ
LPAAT-γ2    YEADMCVRRF PLEDIPLDEK EAAQWLHKLY QEKDALQEIY NQKGMFPGEQ
LPAAT-δ     YHADLYVRRI PLEDIPEDDD ECSAWLHKLY QEKDAFQEEY YRIGTFPETP 310        320        330        340        350
LPAAT-γ1    FKPARRPWTL LNFLSWATIL LSPLFSFVLG VFASGSPLLI ---LTFLGFV
LPAAT-γ2    FKPARRPWTL LNFLSWATIL LSPLFSFVLG VFASGSPLLI ---LTFLGFV
LPAAT-δ     MVPPRRPWTL VNWLFWASLV LYPFFQFLVS MIRSGSSLTL ---ASFILVF 360        370        380
LPAAT-γ1    GAASFGVRRL IGVTEIEKGS SYGNQEF--K KKE*
LPAAT-γ2    GAASFGVRRL IGVTEIEKGS SYGNQEF--K KKE*
LPAAT-δ     FVASVGVRWM IGVTEIDKGS AYGNSDSKQK LND*
```

HUMAN LYSOPHOSHATIDIC ACID ACYLTRANSFERASE GAMMA-1 POLYPEPTIDE

This is a Divisional Application of application Ser. No. 09/970,989, filed on Oct. 5, 2001, now U.S. Pat. No. 6,670,143, which is a Divisional Application of application Ser. No. 09/215,252, filed on Dec. 18, 1998, now U.S. Pat. No. 6,300,487, which is a Continuation-in-Part of application Ser. No. 08/618,651, filed Mar. 19, 1996, now U.S. Pat. No. 6,136,964.

TECHNICAL FIELD OF THE INVENTION

The present invention provides polypeptides having lysophosphatidic acid acyltransferase (LPAAT) activity and polynucleotides encoding polypeptides having LPAAT activity. The present invention further provides for isolation and production of polypeptides involved in phosphatidic acid metabolism and signaling in mammalian cells, in particular, the production of purified forms of LPAAT.

BACKGROUND OF THE INVENTION

LPAAT, also referred to as 1-acyl sn-glycerol-3-phosphate acyltransferase (EC 2.3.1.51), is known to catalyze the acylation of lysophosphatidic acid (LPA) to phosphatidic acid (PA) by acylating the sn-2 position of LPA with a fatty acid acyl-chain moiety. LPA and PA, while originally identified as intermediates in lipid biosynthesis (Kent, *Anal. Rev. Biochem.* 64:315–343, 1995), have more recently been identified as phospholipid signaling molecules that affect a wide range of biological responses (McPhail et al., *Proc. Natl. Acad. Sci. USA* 92:7931–7935, 1995; Williger et al., *J. Biol. Chem.* 270:29656–29659, 1995; Moolenaar, *Curr. Opin. Cell Biol.* 7:203–210, 1995).

Cellular activation in monocytic and lymphoid cells is associated with rapid upregulation of synthesis of phospholipids (PL) that includes PA, diacylglycerol (DAG) and glycan phosphatidylinositol (PI). PAs are a molecularly diverse group of phospholipid second messengers coupled to cellular activation and mitogenesis (Singer et al., *Exp. Opin. Invest. Drugs* 3:631–643, 1994). PA can be generated through hydrolysis of phosphatidylcholine (PC) (Exton, *Biochim. Biophys. Acta* 1212:26–42, 1994) or glycan PI (Eardley et al., *Science* 251:78–81, 1991; Merida et al., *DNA Cell Biol.* 12:473–479, 1993), through phosphorylation of DAG by DAG kinase (Kanoh et al., *Trends Biochem. Sci.* 15:47–50, 1990) or through acylation of LPA at the SN2 position (Bursten et al., *Am. J. Physiol.* 266:C1093–C1104, 1994).

Compounds that block PA generation and hence diminish lipid biosynthesis and the signal involved in cell activation are therefore of therapeutic interest in, for example, the areas of inflammation and oncology as well as obesity treatment. Therefore, compounds that block LPAAT activity have a similar therapeutic value.

The genes coding for LPAAT have been isolated in bacteria (Coleman, *Mol. Gen. Genet.* 232:295–303, 1992), in yeast (Nagiec et al., *J. Biol. Chem.* 268:22156–22163, 1993) and in plants (Brown et al., *Plant Mol. Biol.* 26:211–223, 1994; and Hanke et al., *Eur J. Biochem.* 232: 806–810, 1995; Knutzon, et al., *Plant Physiol.* 109: 999–1006, 1995). Moreover, two human isoforms of LPAAT have been reported (West, et al., *DNA Cell Biol.* 6: 691–701, 1997). These isoforms are denominated LPAATα and LPAATβ (West, et al., *DNA Cell Biol.* 6: 691–701, 1997) and are described herein. There remains, however, a need for the isolation of additional mammalian LPAATs, which can be used, for example, to screen for compounds that inhibit LPAAT activity.

SUMMARY OF THE INVENTION

The present invention provides cDNA sequences, polypeptide sequences, and transformed cells for producing isolated recombinant mammalian LPAAT. The present invention provides four polypeptides corresponding to human LPAAT isoforms. These polypeptides are designated hLPAATα, hLPAATβ, hLPAATγ1, hLPAATγ2, and hLPAATδ. The invention further provides fragments of these polypeptides which are biologically active, i.e., which retain LPAAT activity. LPAAT activity is defined catalyzing acylation of lysophosphatidic acid (LPA) to phosphatidic acid (PA), specifically by acylating the sn-2 position of LPA with a fatty acid acyl-chain moiety.

The present invention further provides nucleic acid sequences encoding hLPAATα, hLPAATβ, hLPAATγ1, hLPAATγ2, and hLPAATδ and polynucleotides coding for biologically active fragments of hLPAATα, hLPAATβ, hLPAATγ1, hLPAATγ2, and hLPAATδ. The invention further provides "biologically active" polynucleotide fragments, which connotes polynucleotide fragments which encode polypeptides having LPAAT activity. The invention further provides purified LPAATs and antisense oligonucleotides for modulation of expression of the genes coding for LPAAT polypeptides. Assays for screening test compounds for their ability to inhibit LPAATs are also provided.

The present invention includes the following polynucleotides coding for hLPAATα, hLPAATβ, hLPAATγ1, hLPAATγ2, and hLPAATδ. The invention provides the DNA sequences of: SEQ ID NO. 1 which encodes for hLPAATα; SEQ ID NO. 7, which encodes hLPAATβ; FIG. 9, which encodes hLPAATγ1 FIG. 10, which encodes hLPAATγ2; and FIG. 11, which encodes and hLPAATδ.

The invention further includes the polypeptides for hLPAATα, hLPAATβ, hLPAATγ1, hLPAATγ2, and hLPAATδ, specifically, the amino acid sequences of: SEQ ID NO. 2, which represents hLPAATα; SEQ ID NO. 8, which represents hLPAATβ; FIG. 9, which represents hLPAATγ1; FIG. 10, which represents hLPAATγ2; and FIG. 11, which represents hLPAATδ.

The invention further comprises biologically active fragments of the amino acid sequences of SEQ ID NO. 2, SEQ ID NO. 8, FIG. 9, FIG. 10, and FIG. 11 or nucleotide fragments of SEQ ID NO. 1, SEQ ID NO. 7, FIG. 9, FIG. 10, and FIG. 11 which encode biologically active LPAAT. The invention further includes polynucleotides which due to the degeneracy of the genetic code encode a polypeptide of SEQ ID NO. 2, SEQ. ID NO. 8, FIG. 9, FIG. 10, and FIG. 11. The invention further includes polynucleotides capable of hybridizing to the nucleic acid sequences of SEQ ID NO. 1, SEQ ID NO. 7, FIG. 9, FIG. 10, and FIG. 11, under high stringency conditions, and which are biologically active.

Also provided by the present invention are vectors containing a DNA sequence encoding a mammalian LPAAT enzyme in operative association with an expression control sequence. Host cells, transformed with such vectors for use in producing recombinant LPAAT, are also provided with the present invention. The inventive vectors and transformed cells are employed in a process for producing recombinant mammalian LPAAT. In this process, a cell line transformed with a DNA sequence encoding LPAAT in operative association with an expression control sequence, is cultured. The claimed process may employ a number of known cells as host cells for expression of the LPAAT polypeptide, including, for example, mammalian cells, yeast cells, insect cells and bacterial cells. The present invention further provides transformed cells that expresses active mammalian LPAAT.

The present invention further provides methods for identifying compounds that increase or decrease LPAAT activity, i.e., acylation of LPA to PA. Because PA concentration is involved in numerous cellular pathways, compounds that increase or decrease acylation of LPA to PA are useful in regulating a number of cellular pathways. Such compounds can be used, for example, to augment trilineage hematopoiesis after cytoreductive therapy or to inhibit inflammation following hypoxia and reoxygenation injury (e.g., sepsis, trauma, and ARDS). Moreover, the present invention contemplates the use of such compounds in an in vitro or in vivo context.

The present invention further includes: An isolated polynucleotide encoding a polypeptide having Lysophosphatidic Acid Acyltransferase (LPAAT) activity, comprising a nucleotide sequence selected from the group consisting of:

(a) the DNA sequence of FIG. 9, FIG. 10, or FIG. 11 and biologically active fragments thereof; and (b) a DNA sequence which encodes the polypeptide of FIG. 9, FIG. 10, or FIG. 11 and biologically active fragments thereof.

An isolated polypeptide having LPAAT activity, comprising the amino acid sequence of FIG. 9, FIG. 10, or FIG. 11 and biologically active fragments thereof.

A method for screening one or more compounds to determine whether the one or more compounds increases or decreases LPAAT activity, comprising:

(a) contacting the polypeptide of the present invention with one or more substrates for the polypeptide and with the one or more compounds; and (b) measuring whether the LPAAT activity of the polypeptide is increased or decreased by the one or more compounds.

A method of expressing the polypeptide of the present invention, comprising:

(a) introducing into a cell a polynucleotide comprising a nucleotide sequence selected from the group consisting of:

(i) the DNA sequence of FIG. 9, FIG. 10, or FIG. 11 and biologically active fragments thereof; and (ii) a DNA sequence which encodes the polypeptide of FIG. 9, FIG. 10, or FIG. 11 and biologically active fragments thereof, wherein the polynucleotide is operably linked to a promoter; and (b) maintaining or growing said cell under conditions that result in the expression of the polypeptide.

An isolated polynucleotide encoding a polypeptide having Lysophosphatidic Acid Acyltransferase (LPAAT) activity, comprising a DNA sequence capable of hybridizing under high stringency conditions to the complement of the DNA sequences, (a) or (b), described above, and which encodes a polypeptide having LPAAT activity.

BRIEF DESCRIPTION OF THE DRAWINGS

FIG. 1 shows the DNA sequence (SEQ ID NO: 1) of the cDNA insert of pZplat.11 encoding hLPAATα (SEQ ID NO: 2).

FIG. 2 shows amino acid sequence alignment of the human LPAATα (SEQ ID NO: 2) coding sequence, the yeast LPAAT (SEQ ID NO: 3) coding sequence, E. coli LPAAT (SEQ ID NO: 4) coding sequence, and the maize LPAAT (SEQ ID NO: 5) coding sequence. This comparison shows that human LPAATα has the greatest extended homology with yeast or E. coli LPAAT than with the plant LPAAT.

FIG. 3 shows the DNA sequence (SEQ ID NO: 6) of the cDNA insert pSP.LPAT3 encoding hLPAATβ. The nucleotide sequence analysis and restriction mapping of the cDNA clone revealed a 5' untranslated region of 39 base pairs and an open reading frame encoding a 278 amino acid polypeptide that spans positions 40–876. It also shows a 3' untranslated region of 480 base pairs from pSP.LPAT3. The initiation site for translation was localized at nucleotide positions 40–42 and fulfilled the requirement for an adequate initiation site (Kozak, *Critical Rev. Biochem. Mol. Biol.* 27:385–402, 1992).

FIG. 4 shows the sequence of the hLPAATβ 278 (SEQ ID NOS: 6 & 7) amino acid open reading frame. The amino acid sequence was used as the query sequence to search for homologous sequences in protein databases. Search of the database based on Genbank Release 92 database from the National Center for Biotechnology Information (NCBI) using the blastp program showed that this protein was most homologous to yeast, bacterial and plant LPAATs.

FIG. 5 shows amino acid sequences alignment of this putative human LPAATβ (SEQ ID NO: 7) coding sequence, human LPAATα (SEQ ID NO: 2) coding, the yeast LPAAT (SEQ ID NO: 3) coding sequence, the bacterial (*E. coli* (SEQ ID NO: 4), *H. influenzae* (SEQ ID NO: 8), and *S. typhimurium*) (SEQ ID NO: 9)) LPAAT coding sequences, and the plant (*L. douglassi* (SEQ ID NO: 10) and *C. nucifera* (SEQ ID NO: 11)) LPAAT coding sequences, revealing that the human LPAAT coding sequences have a much more extended homology with the yeast or the bacterial LPAAT than with the plant LPAAT.

FIG. 6 shows a comparison of LPAAT activity in A549 cells transfected with pCE9.LPAAT1 DNA, or no DNA using a TLC (thin layer chromatography) assay. These data are described in more detail in examples 3 and 4.

FIG. 9 shows the DNA (SEQ ID NO: 12) and the translated sequence of LPAATγ1 (SEQ ID NO: 13).

FIG. 10 shows the DNA (SEQ ID NO: 14) and the translated sequence of LPAATγ2 (SEQ ID NO: 15).

FIG. 11 shows the DNA (SEQ ID NO: 16) and the translated sequence of LPAAT (SEQ ID NO: 17).

FIG. 12 shows the LPAAT amino acid sequence alignment for human LPAAT γ1, (SEQ ID NO: 13), γ2 (SEQ ID NO: 15), and δ (SEQ ID NO: 17).

DETAILED DESCRIPTION OF THE INVENTION

Figure 7:
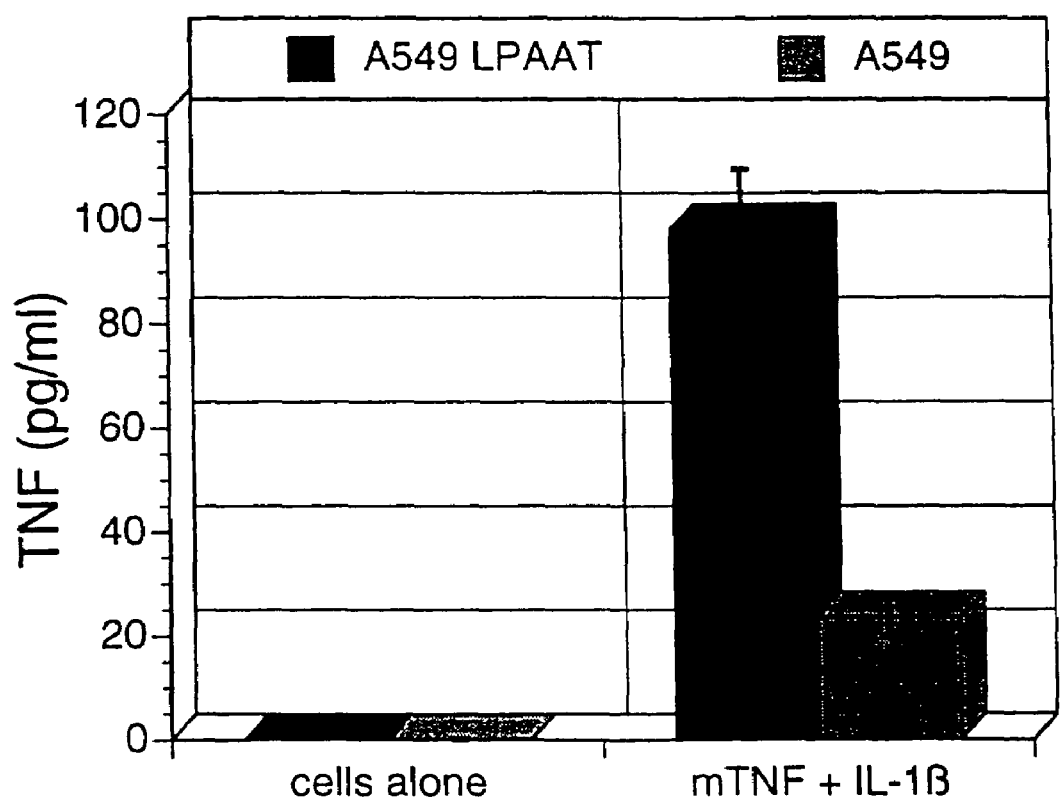
FIGS. 7 and 8 show a comparison of the production of TNF (FIG. 7) and IL-6 (FIG. 8) between A549 cells transfected with pCE9.LPAAT1 and control A549 cells after stimulation with IL-1β and murine TNF. These data show A549 overexpressing LPAAT produces >5 fold more TNF and >10 fold more IL-6 relative to untransfected A549 cells, suggesting that over expression of LPAAT enhances the cytokine signaling response in cells.

The present invention provides isolated LPAAT polypeptides and isolated polynucleotides encoding LPAAT polypeptides. The term "isolated," in this context, denotes a polypeptide or polynucleotide essentially free of other polypeptides or nucleic acid sequences, respectively, or of other contaminants normally found in nature.

The invention includes biologically active LPAAT and biologically active fragments thereof. As used herein, the term "biologically active" in the context of LPAAT activity refers to the ability to catalyze the acylation of lysophosphatidic acid (LPA) to phosphatidic acid (PA) by acylating the sn-2 position of LPA with a fatty acid acyl-chain moiety.

The term "expression product" as used throughout the specification refers to materials produced by recombinant DNA techniques.

The present invention contemplates modification of the hLPAATα, hLPAATβ, hLPAATγ1, hLPAATγ2, and hLPAATδ polypeptide sequences. Such modifications may be deliberate, as by site-directed mutagenesis, or may be spontaneous. All of the polypeptides produced by these modifications are included herein as long as the acyltransferase activity of LPAAT is present.

For example, the present invention contemplates the deletion of one or more amino acids from the polypeptide sequence of the hLPAATα, hLPAATβ, hLPAATγ1, hLPAATγ2, and hLPAATδ to create deletion variants. This deletion can be of one or more amino or carboxy terminal amino acids or one or more internal amino acids. The present invention further contemplates one or more amino acid substitutions to the polypeptide sequence of hLPAATα, hLPAATβ, hLPAATγ1, hLPAATγ2, and hLPAAT to create subsititutional variants. The present invention contemplates that such substitutional variants would contain certain functional alterations, such as stabilizing against proteolytic cleavage. Yet, it is understood that such variants retain their acyltransferase activity.

Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The present invention further contemplates the insertion of one or more amino acids to the polypeptide sequences of hLPAATα, hLPAATβ, hLPAATγ1, hLPAATγ2, and hLPAATδ to create an insertional variant. Examples of such insertional variants include fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Polypeptides of the present invention can be synthesized by such commonly used methods as t-BOC or FMOC protection of alpha-amino groups. Both methods involve step-wise syntheses whereby a single amino acid is added at each step starting from the C terminus of the peptide (Coligan et al., *Current Protocols in Immunology*, Wiley Interscience, Unit 9, 1991). In addition, polypeptide of the present invention can also be synthesized by solid phase synthesis methods (e.g., Merrifield, *J. Am. Chem. Soc.* 85:2149, 1962; and Steward and Young, *Solid Phase Peptide Synthesis*, Freeman, San Francisco pp. 27–62, 1969) using copolyol (styrene-divinylbenzene) containing 0.1–1.0 mM amines/g polymer. On completion of chemical synthesis, the polypeptides can be deprotected and cleaved from the polymer by treatment with liquid HF 10% anisole for about 15–60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopsy, molar rotation, solubility and quantitated by solid phase Edman degradation.

The invention also provides polynucleotides which encode the hLPAAT polypeptides of the invention. As used herein, "polynucleotide" refers to a polymer of deoxyribonucleotides or ribonucleotides in the form of a separate fragment or as a component of a larger construct.

Polynucleotide sequences of the invention include DNA, RNA and cDNA sequences. Preferably, the polynucleotide sequences encoding hLPAAT are the sequences of: SEQ ID NO. 1 for hLPAATα; SEQ ID NO. 7 for LPAATβ; FIG. 9 for hLPAATγ1; FIG. 10 for hLPAATγ2; and FIG. 11 for hLPAATδ. DNA sequences of the present invention can be obtained by several methods. For example, the DNA can be isolated using hybridization procedures which are known in the art. Such hybridization procedures include, for example, hybridization of probes to genomic or cDNA libraries to detect shared nucleotide sequences, antibody screening of expression libraries to detect shared structural features, such as a common antigenic epitope, and synthesis by the polymerase chain reaction (PCR).

Hybridization procedures are useful for screening of recombinant clones by using labeled mixed synthetic oligonucleotide probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions directed to avoid non-specific binding, it is possible to allow an autoradiographic visualization of a specific cDNA clone by the hybridization of the target DNA to that single probe in the mixture, which is its complement (Wallace et al. *Nucl. Acid Res.* 9:879, 1981). Stringent conditions preferably include high stringency conditions. See, for example, Maniatis et al, *Molecular Cloning (A Laboratory Manual)*, Cold Spring Harbor Laboratory, pages 387–389, 1982. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

The development of specific DNA sequences encoding hLPAAT can also be obtained by isolation of double-stranded DNA sequences from the genomic DNA, chemical manufacture of a DNA sequence to provide the necessary codons for the polypeptide of interest, and in vitro synthesis of a double-stranded DNA sequence by reverse transcription of mRNA isolated for a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of mRNA. mRNA is abundant in donor cells that have high levels of genetic expression. In the event of lower levels of expression, PCR techniques are preferred. When a significant portion of the amino acid sequence is known, production of labeled single or double stranded DNA or RNA probe sequences duplicating a sequence putatively present in the target cDNA may be employed in DNA/DNA hybridization procedures, carried out on cloned copies of the cDNA (denatured into a single-stranded form) (Jay et al., *Nucl. Acid Res.* 11:2325, 1983).

A cDNA expression library, such as lambda gt11, can be screened for hLPAATα, hLPAATβ, hLPAATγ1, hLPAATγ2, and hLPAATδ polypeptides using antibodies specific for hLPAATα, hLPAATβ, hLPAATγ1, hLPAATγ2, and hLPAATδ. Such antibodies can be either polyclonally or monoclonally derived.

The polynucleotides of this invention include sequences that are degenerate as a result of the genetic code. The genetic code is described as degenerate because more than one nucleotide triplet, called a codon, can code for a single amino acid. The present invention contemplates the degeneracy of the genetic code and includes all degenerate nucleotide sequences which encode hLPAATα, hLPAATβ, hLPAATγ1, hLPAATγ2, and hLPAATδ.

The present invention also includes polynucleotide sequences complementary to the polynucleotides encoding hLPAATα, hLPAATβ, hLPAATγ1, hLPAATγ2, and hLPAATδ. Specifically, the present invention includes antisense polynucleotides. An antisense polynucleotide is a DNA or RNA molecule complementary to at least a portion of a specific mRNA molecule (Weintraub, *Sci. Amer.* 262:40, 1990). The invention embraces all antisense polynucleotides capable of inhibiting the expression of hLPAATα, hLPAATβ, hLPAATγ1, hLPAATγ2, or hLPAATδ. In a cell, the antisense polynucleotides hybridize to the corresponding mRNA, forming a double-stranded molecule. The antisense polynucleotides interfere with the translation of mRNA since the cell cannot translate mRNA that is double-stranded. Antisense oligomers of about 15 nucleotides are preferred, since they are easily synthesized and are less likely to cause problems than larger molecules when introduced into the target of hLPAATα, hLPAATβ, hLPAATγ1, hLPAATγ2, or hLPAATδ-producing cell. The use of antisense methods to inhibit translation of genes is known (e.g., Marcus-Sakura, *Anal. Biochem.* 172:289, 1988).

The present invention further includes allelic variations, i.e., naturally-occurring base changes in a species population which may or may not result in an amino acid change, to the polynucleotide sequences encoding hLPAATα, hLPAATβ, hLPAATγ1, hLPAATγ2, or hLPAATδ. The inventive polynucleotide sequences further comprise those sequences which hybridize under high stringency conditions (see, for example, Maniatis et al, *Molecular Cloning (A Laboratory Manual)*, Cold Spring Harbor Laboratory, pages 387–389, 1982) to the coding regions or to the complement of the coding regions of hLPAATα, hLPAATβ, hLPAATγ1, hLPAATγ2, or hLPAATδ. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

In addition, ribozyme nucleotide sequences that cleave hLPAATα, hLPAATβ, hLPAATγ1, hLPAATγ2, and hLPAATδ are included in this invention. Ribozymes are RNA molecules possessing an ability to specifically cleave other single-stranded RNA in a manner analogous to DNA restriction endonucleases. Through the modification of nucleotide sequences which transcribe such RNAs, it is possible to engineer molecules that recognize specific nucleotide sequences in an RNA molecule and cleave it (Cech, *J. Amer. Med. Assn.* 260:3030, 1988).

There are two basic types of ribozymes, tetrahymena-type (Hasselhoff, *Nature* 334:585, 1988) and "hammerhead-type". Tetrahymena-type ribozymes recognize sequences which are four bases in length, while "hammerhead-type" ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species.

Production of Polypeptides

Polynucleotide sequences encoding hLPAATα, hLPAATβ, hLPAATγ1, hLPAATγ2, and hLPAATδ polypeptides of the invention can be expressed in either prokaryotes or eukaryotes. Hosts can include microbial (bacterial), yeast, insect and mammalian organisms. Methods of expressing DNA sequences inserted downstream of prokaryotic or viral regulatory sequences in prokaryotes are known in the art (Makrides, *Microbio. Rev.* 60:512, 1996). Biologically functional viral and plasmid DNA vectors capable of expression and replication in a eukaryotic host are known in the art (Cachianes, *Biotechniques* 15:255, 1993). Such vectors are used to incorporate DNA sequences of the invention. DNA sequences encoding the inventive polypeptides can be expressed in vitro by DNA transfer into a suitable host using known methods of transfection.

hLPAATα, hLPAATβ, hLPAATγ1, hLPAATγ2, and hLPAATδ sequences may be inserted into a recombinant expression vector. The term "recombinant expression vector" refers to a plasmid, virus or other vehicle that has been manipulated by inserting or incorporating genetic sequences. Such expression vectors contain a promoter sequence which facilitates efficient transcription of the inserted genetic sequence of the host. The expression vector typically contains an origin of replication and a promoter, as well as specific genes which allow phenotypic selection of the transformed cells. The DNA segment can be present in the vector, operably linked to regulatory elements, for example, a promoter (e.g., T7, metallothionein I, or polyhedren promoters). Vectors suitable for use in the present invention include, for example, bacterial expression vectors, with bacterial promoter and ribosome binding sites, for expression in bacteria (Gold, *Meth. Enzymol.* 185:11, 1990), expression vector with animal promoter and enhancer for expression in mammalian cells (Kaufman, *Meth. Enzymol.* 185:487, 1990) and baculovirus-derived vectors for expression in insect cells (Luckow et al., *J. Virol.* 67:4566, 1993).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The polynucleotide encoding LPAAT can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying a polynucleotide encoding LPAAT is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures*, Texas Agricultural Experimental Station.

The polynucleotides of the present invention can be expressed in any number of different recombinant DNA expression systems to generate large amounts of polypeptide. Included within the present invention are LPAAT polypeptides having native glycosylation sequences, and deglycosylated or unglycosylated polypeptides prepared by the methods described below. Examples of expression systems known to the skilled practitioner in the art include bacteria such as *E. coli*, yeast such as *Pichia pastoris*, baculovirus, and mammalian expression systems such as in Cos or CHO cells.

The polynucleotides of the present invention can be inserted into an expression vector by standard subcloning techniques. In a preferred embodiment, an *E. coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invitrogen, San Diego, Calif.), the Streptag II system (Genosys, Woodlands, Tex.), the FLAG system (IBI, New Haven, Conn.), and the 6xHis (SEQ ID NO: 43) system (Qiagen, Chatsworth, Calif.). Some of these systems produce recombinant polypeptides bearing only a small number of additional amino acids, which are unlikely to affect the LPAAT ability of the recombinant polypeptide. For example, both the FLAG system and the 6xHis (SEQ ID NO: 43) system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invitrogen, San Diego, Calif.).

In an embodiment of the present invention, the polynucleotides encoding LPAAT are analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially in *E. coli*, as it leads to the production of insoluble aggregates which are difficult to renature into the native conformation of the polypeptide.

Accordingly, deletion of one or more of the trrnsmembrane sequences may be desirable. Deletion of transmembrane sequences typically does not significantly alter the conformation or activity of the remaining polypeptide structure. However, one can determine whether deletion of one or more of the transmembrane sequences has effected the biological activity of the LPAAT protein by, for example, assaying the activity of the LPAAT protein containing one or more deleted sequences and comparing this activity to that of unmodified LPAAT. Assaying LPAAT activity can be accomplished by, for example, contacting the LPAAT protein of interest with the substrates LPA and fatty acyl-CoA and measuring the generation of PA or CoA, or, alternatively, measuring the formation of free CoA. Such assays for determining LPAAT activity are described in more detail below in the section describing screening assays.

Moreover, transmembrane sequences, being by definition embedded within a membrane, are inaccessible as antigenic determinants to a host inmmune system. Antibodies to these sequences will not, therefore, provide immunity to the host and, hence, little is lost in terms of generating monoclonal or polyclonal antibodies by omitting such sequences from the recombinant polypeptides of the invention. Deletion of transmembrane-encoding sequences from the polynucleotide used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

Transformation of a host cell with recombinant DNA may be carried out by conventional techniques. When the host is prokaryotic, such as *E. coli*, competent cells which are capable of DNA uptake can be prepared from cells harvested after exponential growth phases and subsequently treated by a $CaCl_2$ method using standard procedures. Alternatively, $MgCl_2$ or RbCl can be used. Transformation can also be performed after forming a protoplast of the host cell or by electroporation.

When the host is a eukaryote, methods of transfection of DNA, such as calcium phosphate co-precipitates, conventional mechanical procedures, (e.g., microinjection), electroporation, liposome-encased plasmids, or virus vectors may be used. Eukaryotic cells can also be cotransformed with DNA sequences encoding hLPAATα, hLPAATβ, hLPAATγ1, hLPAATγ2, and hLPAATδ polypeptides of the invention, and a second foreign DNA molecule encoding a selectable phenotype, such as the herpes simplex thymidine kinase gene. Another method uses a eukaryotic viral vector, such as simian virus 40 (SV40) or bovine papilloma virus to transiently infect or transform eukaryotic cells and express the hLPAATα, hLPAATβ, hLPAATγ1, hLPAATγ2, and hLPAATδ polypeptides.

Expression vectors that are suitable for production of LPAAT polypeptides preferably contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. LPAAT polypeptides of the present invention preferably are expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273, 1982); the TK promoter of Herpes virus (McKnight, *Cell* 31: 355, 1982); the SV40 early promoter (Benoist et al., *Nature* 290:304, 1981); the Rous sarcoma virus promoter (Gorman et al, *Proc. Nat'l. Acad. Sci. USA* 79:6777, 1982); and the cytomegalovirus promoter (Foecking et al., *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter (Zhou et al., *Mol. Cell. Biol.* 10:4529, 1990; Kaufman et al., *Nucl. Acids Res.* 19:4485, 1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991). Examples of mammalian host cells include COS, BHK, 293 and CHO cells.

Purification of Recombinant Polypeptides.

The LPAAT polypeptide expressed in any of a number of different recombinant DNA expression systems can be obtained in large amounts and tested for biological activity. The recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as β-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, biologically active hLPAATα, hLPAATβ, hLPAATγ1, hLPAATγ2, and hLPAATδ useful for screening compounds for, e.g., trilineage hematopoietic and anti-inflammatory therapeutic applications, and developing antibodies for therapeutic, diagnostic and research use.

Screening Assays

The hLPAATα, hLPAATβ, hLPAATγ1, hLPAATγ2, and hLPAATδ polypeptides of the present invention are also useful in a screening methodology for identifying compounds or compositions which affect cellular signaling of an inflammatory response. Such compounds or compositions to be tested can be selected from a combinatorial chemical library or any other suitable source (Hogan, Jr., *Nat. Biotechnology* 15:328, 1997).

This method comprises, for example, contacting hLPAATα, hLPAATβ, hLPAATγ1, hLPAATγ2, and/or hLPAATδ in the presence of compound and substrate for LPAAT, namely LPA and fatty acyl-CoA. These hLPAAT proteins can either be purified prior to incubation or can be contained in extracts from a cell line or cell lines (for example, Sf9, ECV304, A549) transfected with cDNA encoding these polypeptides (West et al., *DNA Cell Biol.* 16:691, 1997). Alternatively, hLPAAT protein can be purified from transfected cells, and the protein, being a transmembrane protein, can then be reconstituted in a lipid bilayer to form liposomes for delivery into cells (Weiner, *Immunomethods* 4:201, 1994).

The effect of a compound or composition on hLPAATα, hLPAATβ, hLPAATγ1, hLPAATγ2, or hLPAATδ activity can be determined, for example, by measuring the generation of PA and CoA. PA can be measured by, for example, TLC methods described in Examples 3 and 7, found below. Alternatively, LPAAT activity can be assayed by detecting the formation of free CoA in reaction. CoA, which contains a free sulfhydryl-group, can be measured either by, for example, colorimetric or fluorescenic methods with sulfhydryl-specific reagents, such as, 5,5'-dithiobis-(2-nitrobenzoic acid) (DTNB) or ThioGlo (Covalent Associates, Woburn, Mass.). The observed effect on hLPAATα, hLPAATβ, hLPAATγ1, hLPAATγ2, and hLPAATδ may be either inhibitory or stimulatory.

Peptide Sequencing

Purified polypeptides prepared by the methods described above can be sequenced using methods well known in the art, for example using a gas phase peptide sequencer (Applied Biosystems, Foster City, Calif.). Because the proteins of the present invention may be glycosylated, it is preferred that the carbohydrate groups are removed from the proteins prior to sequencing. This can be achieved by using glycosidase enzymes. Preferably, glycosidase F (Boehringer-Mannheim, Indianapolis, Ind.) is used. To determine as much of the polypeptide sequence as possible, it is preferred that the polypeptides of the present invention be cleaved into smaller fragments more suitable for gas-phase sequence analysis. This can be achieved by treatment of the polypeptides with selective peptidases, and in a particularly preferred embodiment, with endoproteinase lys-C (Boehringer). The fragments so produced can be separated by reversed-phase HPLC chromatography.

Antibodies Directed to LPAAT

Antibodies to human LPAAT can be obtained using the product of an LPAAT expression vector or synthetic peptides derived from the LPAAT coding sequence coupled to a carrier (Pasnett et al., *J. Biol. Chem.* 263:1728, 1988) as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, an LPAAT antibody of the present invention may be derived from a rodent monoclonal antibody (MAb). Rodent monoclonal antibodies to specific antigens may be obtained by methods known to those skilled in the art. See, for example, Kohler and Milstein, *Nature* 256:495, 1975, and Coligan et aL (eds.), *Current Protocols in Immunology*, 1:2.5.1–2.6.7 (John Wiley & Sons 1991). Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *Methods in Molecular Biology*, 10:79–104 Humana Press, Inc. 1992. An LPAAT antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46:310, 1990.

Alternatively, a therapeutically useful LPAAT antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad. Sci. USA* 86:3833, 1989. Techniques for producing humanized MAbs are described, for example, by Jones et al., *Nature* 321:522, 1986, Riechmann et al., *Nature* 332:323, 1988, Verhoeyen et al., *Science* 239:1534, 1988, Carter et al., *Proc. Nat'l Acad. Sci. USA* 89:4285, 1992, Sandhu, *Crit. Rev. Biotech.* 12: 437, 1992, and Singer et al., *J. Immun.* 150:2844, 1993, each of which is hereby incorporated by reference.

As an alternative, an LPAAT antibody of the present invention may be derived from human antibody fragments isolated from a combinatorial immunoglobulin library. See, for example, Barbas et al., *METHODS: A Companion to Methods in Enzymology* 2:119 1991, and Winter et al., *Ann. Rev. Immunol.* 12:433, 1994, which are incorporated by reference. Cloning and expression vectors that are useful for producing a human immunoglobulin phage library can be obtained, for example, from STRATAGENE Cloning Systems (La Jolla, Calif.). In addition, an LPAAT antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994, and Taylor et al., *Int. Immun.* 6:579, 1994.

hLPAATα and hLPAATβ hLPAATα

Search of the Genbank database of expressed sequence tag (dbest) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out by either the WashU-Merck EST or the Genexpress-Genethon program. An example of the amino acids sequence homology between the yeast LPAAT and a human cDNA clone (dbest#102250)

is shown below by comparing SEQ ID NO. 18 (top amino acid sequence) with SEQ ID NO 19 (bottom amino acid sequence):

```
PFKKGAFHLAQQGKIPIVPVVVSNTSTLVSPKYGVFNRGCMIVRILKPISTE
*   ****** *  **** * *       *   *   ** **** *  **
PSNCGAFHLAVQAQVPIVPIVMSSYQDFYCKKERRFTSGQCQVRVLPPVPTE
```

The top line refers to the yeast LPAAT sequence from amino acids 169 to 220 and the bottom line refers to the homologous region from the dbest clone#102250. Identical amino acids between these two sequences are shown in block letters with asterisks in between.

Accordingly, a synthetic oligonucleotide (o.BLPAT.2R), 5'-TGCAAGATGGAAGGCGCC-3' (SEQ ID NO. 20), was made based on the complement sequence of the conserved amino acids region, GAFHLA (SEQ ID NO. 21), of clone#102250. o.BPLAT.2R was radiolabeled at its 5'-end using $\gamma$-$^{32}$P-ATP and T4 polynucleotide kinase as a probe in screening a λzap human brain cDNA library (Stratagene).

Screening of the cDNA library was accomplished by filter hybridization using standard methods (*Current Protocols in Molecular Biology*, John Wiley & Sons, Inc., 1995). Duplicate filters containing DNA derived from λ phage plagues were prehybridized at 60° C. for 2 hr in 6×SSC (1×SSC is 0.15 M NaCl, 0.015 M sodium citrate, pH 7.0), 5× Denhardt's solution (1× Denhardt's solution is 0.02% Ficoll, 0.02% bovine serum albumin, and 0.02% polyvinyl-pyrrolidone), 0.1% sodium dodecyl sulfate (SDS), 50 mg/ml sonicated and denatured salmon sperm DNA. Hybridization was carried out in the same buffer as used for prehybridzation. After hybridization, the filters were washed in 6×SSC at 42° C., and autoradiographed.

Of the approximately $1 \times 10^6$ clones from the human brain cDNA library that were screened, twelve clones were identified that hybridized with the probe in duplicate filters. Eleven out twelve clones were enriched and recovered after a secondary screen. Ten enriched phage samples were then converted to plasmid transformed cells by co-infecting *E. coli* XL1-Blue with the helper phage R408 using Stratagene's recommended procedure. Colony filter hybridization was performed and identified those colonies that "lit up" with the probe. Seven out of the ten pools of colonies contained positive clones. Two out of these seven clones, pZlpat.10 and pZlpat.11, contained inserts >2 kb. Restriction mapping using a combination of Sst I, Pst I and BamHI digests showed these two clones contained many common fragments with respect to each other.

Nucleotide sequencing of the cDNA inserts in pZlpat.10 and pZlpat.11 was performed. FIG. 1 shows the DNA sequence of the cDNA insert of pZplat.11. The nucleotide sequence analysis and restriction mapping of the cDNA clone revealed a 5'-untranslated region of >300 bp, an open reading frame capable of encoding a 283 amino acid polypeptide, and a 3'-untranslated region of >800 bp. The initiation site for translation was localized at nucleotide positions 319–321 and fulfilled the requirement for an adequate initiation site according to Kozak (Kozak, *Critical Rev. Biochem. Mol. Biol.* 27:385–402, 1992). There was another upstream ATG at positions 131–133 with an in-phase stop codon at positions 176–178. Except with a shorter 5'-untranslated region, the cDNA insert of pZplat.10 has the same DNA sequence as that of pZplat.11.

The sequence of the 283 amino acid open reading frame in pZplat.11 was used as the query sequence to search for homologous sequences in protein databases. Search of the database based on Genbank Release 90 from the National Center for Biotechnology Information (NCBI) using the blastp program showed that the protein encoded by pZplat.11 was most homologous to the yeast and bacterial LPAATs. FIG. 2 shows amino acid sequences alignment of the putative human LPAATα coding sequence, the yeast LPAAT coding sequence, the *E. coli* LPAAT coding sequence, and the maize LPAAT coding sequence, revealing that human LPAATα has a much more extended homology with the yeast or the *E. coli* LPAAT than with the plant LPAAT.

hLPAATβ

Search of the Genbank database (Boguski, et al., *Science* 265:1993–1994, 1994) of expressed sequence tag (dbEST) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out mainly by I.M.A.G.E. Consortium [LLNL] cDNA clones program. An example of the amino acids sequence homology between the yeast LPAAT and a human cDNA clone (dbEST#363498) is shown below:

```
           180       190       200       210       220       230
           QQGKIPIVPVVVSNTSTLVSPKYGVFNRGCMIVRILKPISTENLTKDKIGEFAEKVRDQM
           ....:::::: :. :...  ..:    :...: ..:..:...:.:..::  ...  ..
           VRENVPIVPVVYSSFSSFYNTKKKFFTSGTVTVQVLEAIPTSGLTAADVPALRGTPATGP
                    70        80        90       100       110
           120
```

The top line refers to the yeast LPAAT sequence from amino acids 171 to 230 (SEQ ID NO. 22) and the bottom line refers to the homologous region from the dbest clone#363498 using the +1 reading frame (SEQ ID NO. 23). Identical and conserved amino acids between these two sequences are shown with double dots and single dot, respectively, in between. In order to find out if such cDNA clones with limited homology to yeast LPAAT sequence indeed encode human LPAATβ sequence, it was necessary to isolate the full-length cDNA clone, insert it into an expression vector, and to test if cells transformed or transfected with the cDNA expression vector produced more LPAAT activity.

Accordingly, two synthetic oligonucleotides, 5'-CCT-CAAAGTGTGGATCTATC-3' (o.LPAT3.F) (SEQ ID NO. 24) and 5'-GGAAGAGTACACCACGGGGA C-3' (o.LPAT3.R), (SEQ ID NO. 25) were ordered (Life Technologies, Gaithersburg, Md.) based on, respectively, the coding and the complement sequence of clone#363498. o.LPAT3.R was used in combination with a forward vector primer (o.sport.1), 5'-GACTCTAGCC TAGGCTTTTG C-3' (SEQ ID NO. 26) for amplification of the 5'-region, while o.LPAT3.F was used in combination with a reverse vector primer (o.sport.1R), 5'-CTAGCTTATA ATACGACTCA C-3' (SEQ ID NO. 27), for amplification of the 3'-region of potential LPAATβ sequences from a pCMV.SPORT human leukocyte cDNA library (Life Technologies, Gaithersburg, Md.). A 700 bp PCR fragment derived from o.sport.1 and o.LPAT3.R amplification was cut with EcoR I before inserting in between the Sma I and EcoR I of pBluescript(II)SK(−) (Stratagene, LaJolla, Calif.) to generate pLPAT3.5'. A 900 bp PCR fragment derived from o.sport.1R and o.LPAT3.F amplification was cut with Xba I before inserting in between the Sma I and Xba I of pBluescript(II)SK(−) (Stratagene, LaJolla, Calif.) to generate pLPAT3.3'. Nucleotide sequencing analysis of the cDNA inserts from these two plasmids showed they contained overlapping sequences with each other, sequences that matched with the dbEST#363498 as well as extensive homology with the yeast LPAAT amino acids sequence (Nagiec et al., *J. Biol. Chem.* 268:22156–22163, 1993). To assemble the two halves of the cDNA into a full-length clone, the 560 bp Nco I-Nar I fragment from pLPAT3.5' and the 780 bp Nar I-Xba I fragment from pLPAT3.3' were inserted into the Nco I/Xba I vector prepared from pSP-luc+ (Promega, Madison, Wis.) via a three-part ligation to generate pSP.LPAT3.

FIG. 3 shows the DNA sequence ID of the cDNA insert of pSP.LPAT3. The nucleotide sequence analysis and restriction mapping of the cDNA clone revealed a 5'-untranslated region of 39 bp, an open reading frame capable of encoding a 278 amino acids polypeptide that spans nucleotide positions 40 to 876 and a 3'-untranslated region of 480 bp (FIG. 3). The initiation site for translation was localized at nucleotide positions 40–42 and fulfilled the requirement for an adequate initiation site according to Kozak (Kozak, *Critical Rev. Biochem. Mol. Biol.* 27:385–402, 1992).

The sequence of the 278 amino acid open reading frame (FIG. 4) was used as the query sequence to search for homologous sequences in protein databases. Search of the database based on Genbank Release 92 from the National Center for Biotechnology Information (NCBI) using the blastp program showed that this protein was most homologous to the yeast, bacterial and plant LPAATs. FIG. 5 shows amino acid sequences alignment of this putative human LPAATβ coding sequence, human LPAATα coding, the yeast LPAAT coding sequence, the bacterial (*E. coli, H. influenzae*, and *S. typhimurium*) LPAAT coding sequences, and the plant (*L. douglassi* and *C. nucifera*) LPAAT coding sequences, revealing that the human LPAAT coding sequences have a much more extended homology with the yeast or the bacterial LPAAT than with the plant LPAAT.

hLPAATγ1, hLPAATγ2, or hLPAATδ

Described below is the isolation of human LPAAT isoforms hLPAATγ1, hLPAATγ2, or hLPAATδ, which are distinct from hLPAATα and hLPAATβ.

Search of the Genbank database (Boguski, et al., *Science* 265:1993–1994, 1994) of expressed sequence tag (dbEST) using the maize form-I LPAAT protein (Brown, et al., *Plant Mol. Biol.* 26: 211–223, 1994) sequences as probes resulted in the identification of several short stretches of human cDNA sequences with homology to the maize LPAAT protein sequence. These cDNA sequences of interest were derived from single-run partial sequencing of random human cDNA clones projects carried out mainly by I.M.A.G.E. Consortium [LLNL] cDNA clones program. An example of the amino acids sequence homology between the maize LPAAT and a human cDNA clone (GenBank#T55627) is shown below:

```
150 GLQRLKDFPRPFWLALFVEGTRF 172 (SEQ ID NO: 28)
    ::..::.:.:  .:.  :.  :::::
    GLRRLSDYPEYMWFLLYCEGTRF     (SEQ ID NO: 29)
```

The top line refers to the maize LPAAT sequence from amino acids 150 to 172 and the bottom line refers to the homologous region from the dbEST clone with GenBank#T55627. Identical and conserved amino acids between these two sequences are shown as double dots and single dots, respectively, in the row in between. In order to determine if these human cDNA clones with homology to maize LPAAT but distinct from human LPAATα or LPAATβ indeed encoded human LPAAT, it was undertaken to isolate the full-length cDNA clone, insert it into an expression vector, and to test if cells transformed or transfected with the cDNA expression vector produced more LPAAT activity.

Accordingly, a synthetic oligonucleotides, 5'-GACTAC-CCC GAGTACATGTGGTTTCTC-3' (SEQ ID NO: 30) (oLPTg_1F) was ordered (Life Technologies, Gaithersburg, Md.) based on the coding region corresponding to amino acids DYPEYMWFL (SEQ ID NO: 31) of clone GenBank#T55627. oLPTg_1F was used in combination with a reverse vector primer (o.sport.1R), 5'-CTAGCTTATA ATACGACTCA C-3' (SEQ ID NO: 32), for amplification of the 3'-region of potential LPAAT sequences from a pCMV.SPORT human leukocyte cDNA library (Life Technologies, Gaithersburg, Md.). A 1,000 bp PCR fragment derived from o.sport.1R and oLPTg_1F amplification was cut with Xho I before inserting in between the Sma I and Xho I of pBluescript(II)SK(−) (Stratagene, LaJolla, Calif.) to generate the plasmid pLPTγ_3'. Nucleotide sequencing (performed by the Seattle Biomedical Research Institute sequencing service) analysis of the cDNA inserts from plasmid pLPTg_3' showed it contained sequences that matched with the clone GenBank#T55627 as well as extensive homology with the C-terminal end of the maize LPAAT amino acids sequence (Brown, et al., *Plant Mol. Biol.* 26: 211–223, 1994). To isolate the 5'-portion of this putative LPAAT clone, a synthetic oligonucleotide, 5'-CACATGTC-CGCCTCGTACTT CTTC-3' (SEQ ID NO: 44) (oLPTg_1R), complementary to a region just downstream of the Bam HI site of the cDNA within generate the plasmid pLPTg_3' was used in combination with a forward vector primer (o.sport.1), 5'-GACTCTAGCCTAGGCTTTTG C-3' (SEQ ID NO: 45) for amplification of the 5'-region from a pCMV.SPORT human leukocyte cDNA library (Life Technologies, Gaithersburg, Md.). The PCR fragments generated were cut with Acc65 I and BamH I before inserting in between the Acc65 I and BamH I of pBluescript(II)SK(−) (Stratagene, LaJolla, Calif.). DNA sequence analysis of two cDNA clones containing, respectively, a 980 bp and a 770 bp Acc65 I-BamH I inserts showed they contained sequences that overlapped with the cDNA insert of pLPTγ_3' as well as extensive homology with the N-terminal end of the maize LPAAT amino acids sequence. The DNA sequence of these two cDNA clones diverged at the 5'-regions, suggesting the presence of two alternatively spliced variants with one variant (pLPγ1_5') containing an additional 62 amino acids at the N-terminus relative to the other one (pLPγ2_5'). To assemble the two halves of each cDNA into full-length clones, the 980 bp Acc65I-BamH I fragment from pLPγ1_5' or the 770 bp Acc65I-BamH I fragment from pLPγ2_5' were inserted into the Acc65I/Xho I vector prepared from pBluescript(II)SK(−) (Stratagene, LaJolla, Calif.) along with the 870 bp Bam HI-Xho I fragment from pLPTγ_3' via a three-part ligation to generate pSK_Lpγ1 and pSK_Lpγ2, respectively.

FIG. 9 shows the DNA and the translated sequence (LPAAT-γ1) of the cDNA insert of pSK_LPγ1. The nucleotide sequence analysis and restriction mapping of the cDNA clone revealed a 5'-untranslated region of 183 bp with two ATGs and an in-phase stop codon, an open reading frame capable of encoding a 376 amino acids polypeptide that spans nucleotide positions 184 to 1314 and a 3'-untranslated region of 345 bp. The initiation site for translation was localized at nucleotide positions 184–186 and fulfilled the requirement for an adequate initiation site (Kozak, *Critical Rev. Biochem. Mol. Biol.* 27:385–402, 1992).

FIG. 10 shows the DNA and the translated sequence (hLPAATγ2) of the cDNA insert of pSK_LPγ2. The nucleotide sequence analysis and restriction mapping of the cDNA clone revealed a 5'-untranslated region of 232 bp with two upstream ATGs with in-phase stop codons, an open reading frame capable of encoding a 314 amino acids polypeptide that spans nucleotide positions 133 to 1177 and a 3'-untranslated region of 346 bp. The initiation site for translation was localized at nucleotide positions 233–235 and fulfilled the requirement for an adequate initiation site (Kozak, *Critical Rev. Biochem. Mol. Biol.* 27:385–402, 1992).

The sequence of the 376 amino acid open reading frame of hLPAATγ1 (FIG. 9) was used as the query sequence to search for homologous sequences in protein databases. Search of the Genbank database from the National Center for Biotechnology Information (NCBI) using the tblastn program showed that this protein was distinct but homologous to a human EST sequence with GenBank #H18562. Shown below is the amino acid sequences alignment of LPAAT-γ1 with this putative human LPAAT coding sequence (LPAAT-δ): (SEQ ID NOS 33 & 34)

FIG. 12 shows the LPAAT amino acid sequence alignment from the human isoforms γ1, γ2, and δ. Amino acids identical in at least two sequences are highlighted. LPAAT-γ1 and LPAAT-δ have an overall amino acid match of 54% with respect to each other.

EXAMPLE 1

This example illustrates an experiment to determine if the human LPAATα clone encodes a protein with LPAAT activity, an *E. coli* vector expressing the human LPAATα as a fusion protein with β-galactosidase was transformed into a LPAAT minus strain of *E. coli* to see if it would complement the defect in *E. coli*. Specifically, the 840 bp Bgl II-Nco I fragment, which spans the coding region of human LPAATα from amino acid 68 to beyond the stop codon, derived from pZplat.11 was inserted into a Bgl II/Nco I digested cloning vector pLitmus28 (Evans et al., *BioTechniques* 19:130–135, 1995) to generate the plasmid p28BgN. This plasmid is expected to express the human LPAATα as a fusion protein containing the first 16 amino acids of β-galactosidase and the last 216 residues of the human LPAATα coding sequence using the lac promoter in pLitmus28. This plasmid was transformed into the *E. coli* strain JC201 (obtained from Dr. Jack Coleman, Louisiana State University). JC201 (Coleman, *Mol. Gen. Genet.* 232:295–303, 1992; Nagiec et al., *J. Biol. Chem.* 268: 22156–22163, 1993; and Brown et al., *Plant Mol. Biol.* 26:211–223, 1994) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with p28BgN was able to grow normally at 44° C. when compared to the wild type strain JC200 (plsC⁺), while JC201 transformed with pLitmus28 vector was not able to support growth at 44° C. These data suggest that the putative human LPAATα cDNA isolated here does possess LPAAT activity, as the last 216 amino

```
(SEQ ID NOS 33 & 34)
LPAAT-γ1    MGLLAFLKTQFVLHLLVGFVFVVSGLVINFVQLCTLALWPVSKQLY          46
            : :   ::.::.  ::.   .::. :::.::  .::  ::  :::.  :::.
LPAAT-δ     MDLAGLLKSQFLCHLVFCYVFIASGLIINTIQLFTLLLWPINKQLF         340
```

The top line refers to the human LPAAT-γ1 sequence from amino acids 1 to 46 and the bottom line refers to the homologous region from the dbEST clone with GenBank #H18562. Identical and conserved amino acids between these two sequences are shown as double dots and single dots, respectively, in the row in between. The cDNA for this putative LPAAT-δ clone (Genome Systems Inc., St. Louis, Mo.) was isolated for further analysis.

FIG. 11 shows the DNA and the translated sequence (LPAAT-δ) of this cDNA insert. Nucleotide sequence analysis and restriction mapping revealed a 5'-untranslated region of 157 bp with an upstream ATG and stop codons in all three reading frames, an open reading frame capable of encoding a 378 amino acids polypeptide that spans nucleotide positions 158 to 1294 and a 3'-untranslated region of 480 bp. The initiation site for translation was localized at nucleotide positions 158–160 and fulfilled the requirement for an adequate initiation site (Kozak, *Critical Rev. Biochem. Mol. Biol.* 27:385–402, 1992).

acids of this cDNA is sufficient to complement the defective LPAAT gene (plsC) in JC201.

EXAMPLE 2

To see if the putative human LPAATβ clone encodes a protein with LPAAT activity, an *E. coli* vector expressing this human LPAATβ as a direct product was transformed into a LPAAT minus strain of *E. coli* to see if it would complement the defect in *E. coli*. Specifically, the 1350 bp Nco I-Xba I fragment from pSP.LPAT3, which spans the entire coding region from amino acid 1 to beyond the stop codon, was inserted into a Nco I/Xba I digested cloning vector pKK388-1 (Clontech, Palo Alto, Calif.) to generate the plasmid pTrc.LPAT3. This plasmid was transformed into the *E. coli* strain JC201 (obtained from Dr. Jack Coleman, Louisiana State University). JC201 (Coleman, *Mol. Gen. Genet.* 232:295–303, 1992) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with pTrc.LPAT3 was able to grow normally at 44° C. when compared to the wild type strain JC200 (plsC+), while JC201 transformed with pKK388-1 vector was not able to support growth at 44° C. These data suggest that the putative human LPAATβ cDNA isolated here does possess LPAAT activity, as the putative protein product of this cDNA is able to complement the defective LPAAT gene (plsC) in JC201.

EXAMPLE 3

This example illustrates a group of experiments to see if overexpression of this human LPAATα would have any effect on mammalian cells. The entire cDNA insert (~2,300 bp) from pZplat.11 was cleaved with Asp718 I and Xho I for insertion into the mammnalian expression vector pCE9 to generate pCE9.LPAAT1. pCE9 was derived from pCE2 with two modifications. The 550 bp BstY I fragment within the elongation factor-1a (EF-1a) intron of pCE2 was deleted. The multiple cloning region of pCE2 between the Asp718 I and BamH I site was replaced with the multiple cloning region spanning the Asp718 I and Bgl II sites from pLitmus28. The plasmid pCE2 was derived from pREP7b (Leung, et al., *Proc. Natl. Acad. Sci. USA*, 92: 4813–4817, 1995) with the RSV promoter region replaced by the CMV enhancer and the elongation factor-1a (EF-1a) promoter and intron. The CMV enhancer came from a 380 bp Xba I-Sph I fragment produced by PCR from pCEP4 (Invitrogen, San Diego, Calif.) using the primers 5'-GGCTCTAGAT ATTAATAGTA ATCAATTAC-3' (SEQ ID NO: 35) and 5'-CCTCACGCAT GCACCATGGT AATAGC-3' (SEQ ID NO: 36). The EF-1a promoter and intron (Uetsuki, et al., *J. Biol. Chem.*, 264: 5791–5798, 1989) came from a 1200 bp Sph I-Asp718 I fragment produced by PCR from human genomic DNA using the primers 5'-GGTGCATGCG TGAGGCTCCG GTGC-3' (SEQ ID NO: 37) and 5'-GTAGTTTTCA CGGTACCTGA AATGGAAG-3' (SEQ ID NO: 38). These 2 fragments were ligated into a Xba I/Asp718 I digested vector derived from pREP7b to generate pCE2.

pCE9.LPAAT1 DNA was transfected into several mammalian cell lines, including A549 cells, ECV304 cells (American Type Culture Collection, Rockville, Md.), two human cell line that would produce IL-6 and TNF upon stimulation with IL-1b and murine TNF and 293-EBNA cells (Invitrogen, San Diego, Calif.). pCE9.LPAAT1 was digested with BspH I before electroporating into these cell lines with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 μg/ml Hygromycin B (Hyg) (Calbiochem, La Jolla, Calif.) to select for cells that had incorporated both plasmids. Hyg-resistant clones that expressed LPAAT mRNA at a level more than 20 fold higher relative to untransfected cells based on Northern Blot analysis (Kroczek, et al., *Anal. Biochem.* 184: 90–95, 1990) were selected for further study.

FIG. 6 compares the LPAAT activity in A549 cells and in A549 cells transfected with pCE9.LPAAT1 DNA using a TLC assay. This screening assay for LPAAT activity in cell extracts was based on a fluorecent assay using fluorescent lipid substrates (Ella, et al., *Anal. Biochem.* 218: 136–142, 1994). Instead of using the PC-substrate, BPC (Molecular Probes, Eugene, Oreg.), a synthetic PC that contains an ether linkage at the SN1 position with a fluorescent Bodipy moiety incorporated into the end of the alkyl-chain at the SN1 position, BPC was converted to Bodipy-PA using cabbage phospholipase D (Sigma, St. Louis, Mo.). Bodipy-PA was then converted to Bodipy-LPA using snake venom phospholipase A2. The Bodipy-LPA obtained was purified by preparative TLC for use in the LPAAT assay. The assay was carried out in total cell extracts resuspended in lysis buffer (Ella, et al., *Anal. Biochem.* 218: 136–142, 1994) supplemented with 0.5 mM ATP, 0.3 mM $MgCl_2$, 100 μM oleoyl-CoA and 10 μM Bodipy LPA. The samples were incubated for 30 min before loading onto TLC plates.

Lane 1 refers to Bodipy LPA incubated with buffer only without any cell extract added. Lane 9 refers to BPC treated with cabbage phospholipase D for generating a Bodipy-PA marker. Lanes 2 and 4 refer to Bodipy LPA incubated with control A549 cell extracts with or without lipid A, respectively. Lanes 3 and 5 refer to Bodipy LPA incubated with A549 cell extracts transfected with pCE9.LPAAT1 DNA with or without lipid A, respectively. FIG. 3 shows A549 cells transfected with the LPAAT cDNA (lanes 3 and 5) contain much more LPAAT activity than those of control cells (lanes 2 and 4) as evidenced by the increased conversion of Bodipy-LPA to Bodipy-PA. Addition of lipid A to the cell extracts has little effect on LPAAT activity (lanes 2 vs 4 and 3 vs 5). A549 cell extract also contains a phosphohydrolase activity that converts Bodipy-LPA to Bodipy-monoalkylglycerol (lanes 2 to 5). Interestingly, A549 cells overexpressing LPAAT (lanes 3 and 5) have less of this activity compared to control cells (lanes 2 and 4), suggesting this phosphohydrolase prefers LPA to PA as substrate. There is also an increase of DAG in transfected cells (lanes 3 and 5) compared to control cells (lanes 2 and 4) possibly due to partial conversion of the PA formed to DAG from this endogenous phosphohydrolase.

EXAMPLE 4

To see if the expressed LPAAT cDNA clone described here would also use other glycerol-lipids that contain a free-hydroxyl group at the SN2 position, the cell extracts were incubated with the substrates NBD-lysoPC (lanes 6 and 7) and NBD-monoacylglycerol (MAG) (lanes 10 and 11) to see if there is increased conversion to lysoPC and DAG, respectively. Lane 8 and 12 refer, respectively, to NBD-lysoPC and NBD-MAG incubated with buffer only without any cell extract added. TLC analysis shows little difference in the lipid profile between the transfected and control cells (lanes 7 vs 6, lanes 11 vs 10), suggesting the cloned LPAAT enzyme uses LPA as the preferred substrate. It is likely that the acyltransferases for lysoPC (Fyrst, et al., *Biochem. J.* 306:793–799, 1995) and for MAG (Bhat, et al., *Biochemistry* 34: 11237–11244, 1995) represent different enzymes from the LPAAT described here.

EXAMPLE 5 pCE9.LPAAT1 DNA was transfected into A549 cells (American Type Culture Collection, Rockville, Md.), a human cell line that would produce IL-6 and TNF upon stimulation with IL-1β and murine TNF. pCE9.LPAAT1 was digested with BspH I before electroporating into A549 cells with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 μg/ml Hygromycin B (Hyg) (Calbiochem, La Jolla, Calif.) to select for cells that had incorporated both plasmids. A Hyg-resistant clone that expressed LPAAT mRNA at a level more than 20 fold higher relative to untransfected A549 cells based on Northern Blot analysis (Kroczek et al., *Anal. Biochem.* 184:90–95, 1990) was selected for further study.

Figure 8:
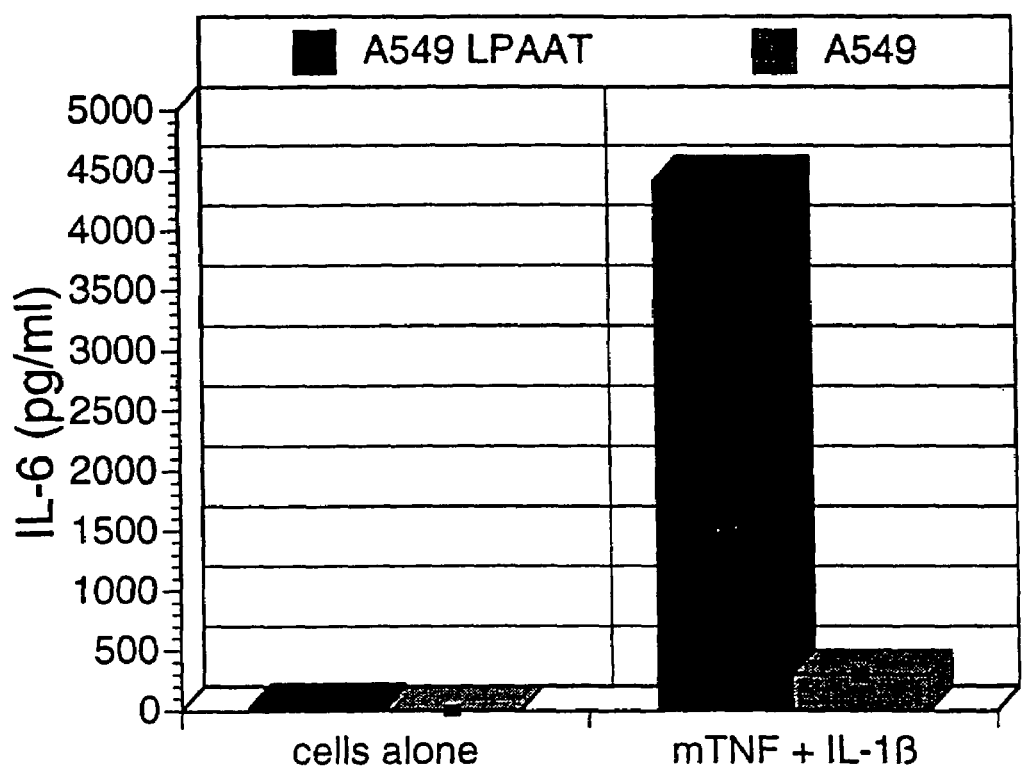

A comparison of the production of TNF (FIG. 7) and IL-6 (FIG. 8) between A549 cells transfected with pCE9.LPAAT1 and control A549 cells after stimulation with IL-1β and murine TNF shows A549 overexpressing LPAAT produces >5 fold more TNF and >10 fold more IL-6 relative to untransfected A549 cells, suggesting that overexpression of LPAAT would enhance the cytokine signaling response in cells. Development of compounds that would modulate LPAAT activity should therefore be of therapeutic interest in the field of inflammation.

EXAMPLE 6

Construction of pC9LPTγ1 and pC2LPTδ: The primers 5'-ggcccggtacc ATGGGCCTG CTGGCCTTC C-3' (SEQ ID NO: 39) (oLPγ1_1F) and 5'-taactcCTCGAG TTATTCCTT TTTCTTAAA CTC-3' (SEQ ID NO: 40) (oLPγ1_1R) were used to amplify the 1100 bp Acc65I-XhoI fragment by PCR from the template pSK_LPg1. The fragment generated was then inserted into a Acc65I/Xho I digested pCE9 (West, et al., *DNA Cell Biol.* 6: 691–701, 1997) expression vector to make pC9LPTγ1. Similarly, the primers 5'-atggtggtaccacc ATGGACCTC GCGGGACTG CTG-3' (SEQ ID NO: 41) (oLPTδ_1F) and 5'-GGAgGATATctAGAgGCCAC CAGTTC-3' (SEQ ID NO: 42) (oLPTδ_1R) were used to amplify the 1100 bp Acc65I-Xba I fragment by PCR from the template #H18562. The fragment generated was then inserted into a Acc65I/Nhe I digested pCE2 (West, et al., *DNA Cell Biol.* 6: 691–701, 1997) expression vector to make pC2LPTδ.

EXAMPLE 7

Expression of hLPAATγ1 and hLPAATδ in mammalian cells. Plasmids pC9LPTγ1 or pC2LPTδ were stably transfected into endothelial ECV304 cells (American Type Culture Collection, Rockville, Md.). Specifically, pC9LPTγ1 or pC2LPTδ were digested with BspH I before electroporating into these cell lines with a Cell-Porator™ (Life Technologies, Gaithersburg, Md.). After adherence of the transfected cells 24 hours later, the cells were grown in the presence of 500 μg/ml Hygromycin B (Hyg) (Calbiochem, La Jolla, Calif.) to select for cells that had incorporated plasmids. Hyg-resistant clones that expressed LPAAT-γ1 or LPAAT-δ mRNA at a level more than 10 fold higher than that of cells transfected with pCE9 or pCE2 vector, based on Northern Blot analysis, were selected for further study.

Figure 13:
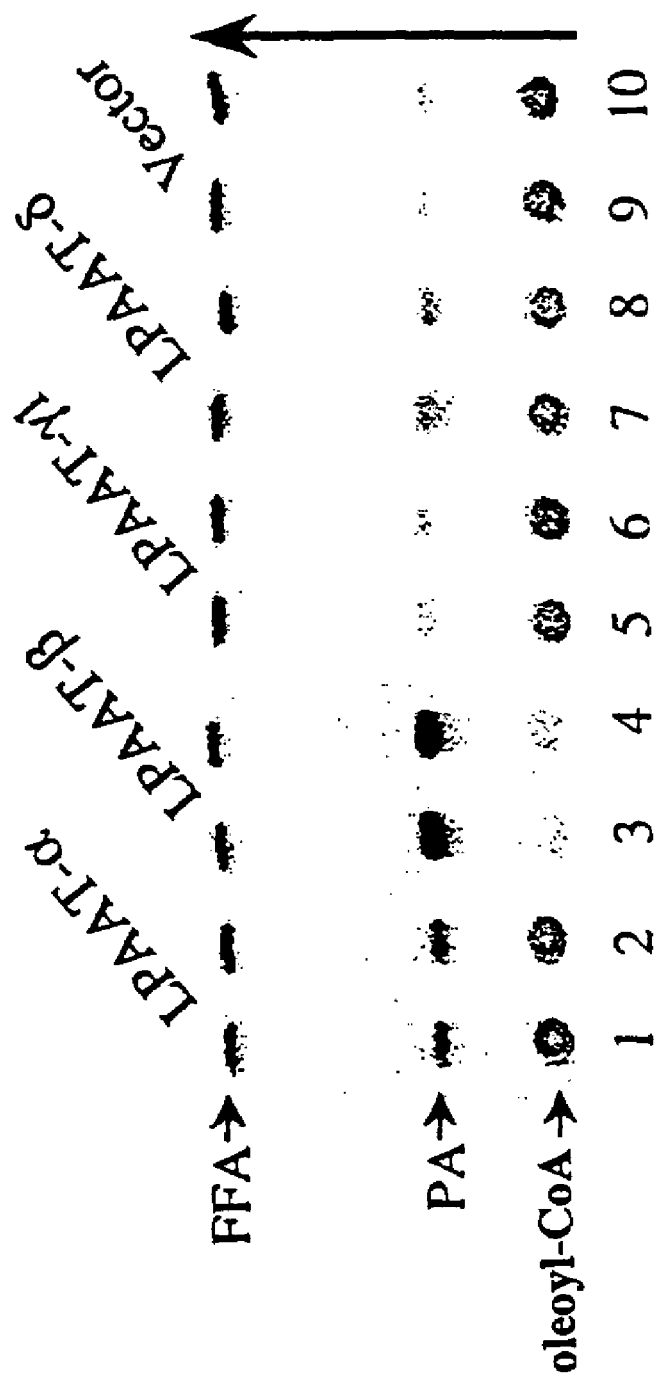
FIG. 13 compares the LPAAT activity in ECV304 cells stably transfected with the expression plasmids for LPAATα (pCE9.LPAAT-α), LPAATβ (pCE9.LPAAT-β) DNA, LPAATγ1 (pC9LPTγ1), LPAATδ (pC2LPTδ), or the control vector (pCE9).

FIG. 13 compares the LPAAT activity in ECV304 cells stably transfected with the expression plasmids for LPAAT-α (pCE9.LPAAT-α), LPAAT-β (pCE9.LPAAT-β) DNA, LPAAT-γ1 (pC9LPTγ1), LPAAT-δ (pC2LPTδ), or the control vector (pCE9). This screening assay for LPAAT activity in cell extracts was based on the conversion of [$^{14}$C]oleoyl-CoA to [$^{14}$C]PA using a TLC assay. The assay was carried out in total cell extracts resuspended in lysis buffer (Ella, et al., *Anal. Biochem.* 218: 136–142, 1994) supplemented with 50 μM [$^{14}$C]oleoyl-CoA and 200 μM LPA. The samples were incubated for 10 min, extracted from chloroform, before loading onto TLC plates. Lanes 1 and 2 refer to [$^{14}$C]oleoyl-CoA and LPA incubated with cell extract transfected with LPAAT-α plasmid; lanes 3 and 4, with LPAAT-β plasmid; lanes 5 and 6, with LPAAT-γ1 plasmid; lanes 7 and 8, with LPAAT-δ plasmid; and lanes 9 and 10, with control vector. ECV304 cells transfected with LPAAT-α or -β cDNA (lanes 1 to 4) contain more than 3 and 20 times, respectively, LPAAT activity when compared to those of control cells (lanes 9 and 10) as evidenced by the increased conversion of [$^{14}$C]oleoyl-CoA to [$^{14}$C]PA. Cells transfected with LPAAT-δ cDNA (lanes 7 and 8) contain about 2.5 times more LPAAT activity than those of control cells (lanes 9 and 10), whereas cells transfected with LPAAT-δ cDNA show no increase in activity when compared to those of control cells (lanes 9 and 10).

We claim:

1. An isolated polypeptide having lysophosphatidic acid acyltransferase activity, comprising the amino acid sequence SEQ ID NO: 13.

* * * * *

SEQUENCE LISTING

```
<160> NUMBER OF SEQ ID NOS: 45

<210> SEQ ID NO 1
<211> LENGTH: 2242
<212> TYPE: DNA
<213> ORGANISM: Homo sapiens
<220> FEATURE:
<221> NAME/KEY: CDS
<222> LOCATION: (319)..(1167)

<400> SEQUENCE: 1
ggaagtcagc aggcgttggg gagggtggc ggggaatag cggcggcagc agccccagcc        60
ctcagagaga cagcagaaag ggagggaggg agggtgctgg ggggacagcc ccccaccatt     120
cctaccgcta tgggcccaac ctcccactcc cacctcccct ccatcggccg gggctaggac     180 accccaaat cccgtcgccc ccttggcacc gacaccccga cagagacaga gacacagcca      240
tccgccacca ccgctgccgc agcctggctg gggaggggc cagcccccca ggcccctac      300 ccctctgagg tggccaga atg gat ttg tgg cca ggg gca tgg atg ctg ctg       351
                      Met Asp Leu Trp Pro Gly Ala Trp Met Leu Leu
                       1               5                  10
```

-continued

| | | |
|---|---|---|
| ctg ctg ctc ttc ctg ctg ctc ttc ctg ctg ccc acc ctg tgg ttc<br>Leu Leu Leu Phe Leu Leu Leu Phe Leu Leu Pro Thr Leu Trp Phe<br>                15                  20                25 | 399 |
| tgc agc ccc agt gcc aag tac ttc ttc aag atg gcc ttc tac aat ggc<br>Cys Ser Pro Ser Ala Lys Tyr Phe Phe Lys Met Ala Phe Tyr Asn Gly<br>        30                  35                  40 | 447 |
| tgg atc ctc ttc ctg gct gtg ctc gcc atc cct gtg tgt gcc gtg cga<br>Trp Ile Leu Phe Leu Ala Val Leu Ala Ile Pro Val Cys Ala Val Arg<br>      45                  50                  55 | 495 |
| gga cgc aac gtc gag aac atg aag atc ttg cgt cta atg ctg ctc cac<br>Gly Arg Asn Val Glu Asn Met Lys Ile Leu Arg Leu Met Leu Leu His<br>60                  65                  70                  75 | 543 |
| atc aaa tac ctg tac ggg atc cga gtg gag gtg cga ggg gct cac cac<br>Ile Lys Tyr Leu Tyr Gly Ile Arg Val Glu Val Arg Gly Ala His His<br>                80                  85                  90 | 591 |
| ttc cct ccc tcg cag ccc tat gtt gtt gtc tcc aac cac cag agc tct<br>Phe Pro Pro Ser Gln Pro Tyr Val Val Val Ser Asn His Gln Ser Ser<br>              95                  100                105 | 639 |
| ctc gat ctg ctt ggg atg atg gag gta ctg cca ggc cgc tgt gtg ccc<br>Leu Asp Leu Leu Gly Met Met Glu Val Leu Pro Gly Arg Cys Val Pro<br>            110                  115                120 | 687 |
| att gcc aag cgc gag cta ctg tgg gct ggc tct gcc ggg ctg gcc tgc<br>Ile Ala Lys Arg Glu Leu Leu Trp Ala Gly Ser Ala Gly Leu Ala Cys<br>            125                  130                135 | 735 |
| tgg ctg gca gga gtc atc ttc atc gac cgg aag cgc acg ggg gat gcc<br>Trp Leu Ala Gly Val Ile Phe Ile Asp Arg Lys Arg Thr Gly Asp Ala<br>140                  145                  150                155 | 783 |
| atc agt gtc atg tct gag gtc gcc cag acc ctg ctc acc cag gac gtg<br>Ile Ser Val Met Ser Glu Val Ala Gln Thr Leu Leu Thr Gln Asp Val<br>                  160                165                170 | 831 |
| agg gtc tgg gtg ttt cct gag gga acg aga aac cac aat ggc tcc atg<br>Arg Val Trp Val Phe Pro Glu Gly Thr Arg Asn His Asn Gly Ser Met<br>            175                  180                185 | 879 |
| ctg ccc ttc aaa cgt ggc gcc ttc cat ctt gca gtg cag gcc cag gtt<br>Leu Pro Phe Lys Arg Gly Ala Phe His Leu Ala Val Gln Ala Gln Val<br>            190                  195                200 | 927 |
| ccc att gtc ccc ata gtc atg tcc tcc tac caa gac ttc tac tgc aag<br>Pro Ile Val Pro Ile Val Met Ser Ser Tyr Gln Asp Phe Tyr Cys Lys<br>            205                  210                215 | 975 |
| aag gag cgt cgc ttc acc tcg gga caa tgt cag gtg cgg gtg ctg ccc<br>Lys Glu Arg Arg Phe Thr Ser Gly Gln Cys Gln Val Arg Val Leu Pro<br>220                225                  230                235 | 1023 |
| cca gtg ccc acg gaa ggg ctg aca cca gat gac gtc cca gct ctg gct<br>Pro Val Pro Thr Glu Gly Leu Thr Pro Asp Asp Val Pro Ala Leu Ala<br>                  240                245                250 | 1071 |
| gac aga gtc cgg cac tcc atg ctc act gtt ttc cgg gaa atc tcc act<br>Asp Arg Val Arg His Ser Met Leu Thr Val Phe Arg Glu Ile Ser Thr<br>            255                  260                265 | 1119 |
| gat ggc cgg ggt ggt ggt gac tat ctg aag aag cct ggg ggc ggt ggg<br>Asp Gly Arg Gly Gly Gly Asp Tyr Leu Lys Lys Pro Gly Gly Gly Gly<br>            270                  275                280 | 1167 |
| tgaaccctgg ctctgagctc tcctcccatc tgtccccatc ttcctcccca cacctaccca | 1227 |
| cccagtgggc cctgaagcag ggccaaaccc tcttccttgt ctccctctc cccacttatt | 1287 |
| ctcctctttg gaatcttcaa cttctgaagt gaatgtggat acagcgccac tcctgccccc | 1347 |
| tcttggcccc atccatggac tcttgcctcg gtgcagtttc cactcttgac ccccacctcc | 1407 |
| tactgtcttg tctgtgggac agttgcctcc ccctcatctc cagtgactca gcctacacaa | 1467 |
| gggaggggaa cattccatcc ccagtggagt ctcttcctat gtggtcttct ctacccctct | 1527 |

```
acccccacat tggccagtgg actcatccat tctttggaac aaatcccccc ccactccaaa    1587
gtccatggat tcaatggact catccatttg tgaggaggac ttctcgccct ctggctggaa    1647
gctgatacct gaagcactcc caggctcatc ctgggagctt tcctcagcac cttcaccttc    1707
cctcccagtg tagcctcctg tcagtggggg ctggacccct ctaattcaga ggtctcatgc    1767
ctgcccttgc ccagatgccc aggtcgtgc actctctggg ataccagttc agtctccaca     1827
tttctggttt tctgtcccca tagtacagtt cttcagtgga catgacccca cccagccccc    1887
tgcagccctg ctgaccatct caccagacac aagggggaaga agcagacatc aggtgctgca   1947
ctcacttctg cccctgggg agttggggaa aggaacgaac cctggctgga ggggatagga     2007
gggcttttaa tttatttctt tttctgttga ggcttccccc tctctgagcc agttttcatt    2067
tcttcctggt ggcattagcc actccctgcc tctcactcca gacctgttcc cacaactggg    2127
gaggtaggct gggagcaaaa ggagagggtg ggacccagtt ttgcgtggtt ggttttatt     2187 aattatctgg ataacagcaa aaaaactgaa aataaagaga gagagaaaaa aaaaa         2242
```

<210> SEQ ID NO 2
<211> LENGTH: 283
<212> TYPE: PRT
<213> ORGANISM: Homo sapiens

<400> SEQUENCE: 2

```
Met Asp Leu Trp Pro Gly Ala Trp Met Leu Leu Leu Leu Phe Leu
  1               5                  10                  15

Leu Leu Leu Phe Leu Leu Pro Thr Leu Trp Phe Cys Ser Pro Ser Ala
                 20                  25                  30

Lys Tyr Phe Phe Lys Met Ala Phe Tyr Asn Gly Trp Ile Leu Phe Leu
             35                  40                  45

Ala Val Leu Ala Ile Pro Val Cys Ala Val Arg Gly Arg Asn Val Glu
         50                  55                  60

Asn Met Lys Ile Leu Arg Leu Met Leu Leu His Ile Lys Tyr Leu Tyr
 65                  70                  75                  80

Gly Ile Arg Val Glu Val Arg Gly Ala His His Phe Pro Pro Ser Gln
                 85                  90                  95

Pro Tyr Val Val Val Ser Asn His Gln Ser Ser Leu Asp Leu Leu Gly
            100                 105                 110

Met Met Glu Val Leu Pro Gly Arg Cys Val Pro Ile Ala Lys Arg Glu
        115                 120                 125

Leu Leu Trp Ala Gly Ser Ala Gly Leu Ala Cys Trp Leu Ala Gly Val
    130                 135                 140

Ile Phe Ile Asp Arg Lys Arg Thr Gly Asp Ala Ile Ser Val Met Ser
145                 150                 155                 160

Glu Val Ala Gln Thr Leu Leu Thr Gln Asp Val Arg Val Trp Val Phe
                165                 170                 175

Pro Glu Gly Thr Arg Asn His Asn Gly Ser Met Leu Pro Phe Lys Arg
            180                 185                 190

Gly Ala Phe His Leu Ala Val Gln Ala Gln Val Pro Ile Val Pro Ile
        195                 200                 205

Val Met Ser Ser Tyr Gln Asp Phe Tyr Cys Lys Lys Glu Arg Arg Phe
    210                 215                 220

Thr Ser Gly Gln Cys Gln Val Arg Val Leu Pro Pro Val Pro Thr Glu
225                 230                 235                 240

Gly Leu Thr Pro Asp Asp Val Pro Ala Leu Ala Asp Arg Val Arg His
```

```
                    245                 250                 255
Ser Met Leu Thr Val Phe Arg Glu Ile Ser Thr Asp Gly Arg Gly
            260                 265                 270
Gly Asp Tyr Leu Lys Lys Pro Gly Gly Gly Gly
            275                 280
```

<210> SEQ ID NO 3
<211> LENGTH: 303
<212> TYPE: PRT
<213> ORGANISM: Saccharomyces cerevisiae

<400> SEQUENCE: 3

```
Met Ser Val Ile Gly Arg Phe Leu Tyr Tyr Leu Arg Ser Val Leu Val
  1               5                  10                  15
Val Leu Ala Leu Ala Gly Cys Gly Phe Tyr Gly Val Ile Ala Ser Ile
                 20                  25                  30
Leu Cys Thr Leu Ile Gly Lys Gln His Leu Ala Gln Trp Ile Thr Ala
             35                  40                  45
Arg Cys Phe Tyr His Val Met Lys Leu Met Leu Gly Leu Asp Val Lys
         50                  55                  60
Val Val Gly Glu Glu Asn Leu Ala Lys Lys Pro Tyr Ile Met Ile Ala
 65                  70                  75                  80
Asn His Gln Ser Thr Leu Asp Ile Phe Met Leu Gly Arg Ile Phe Pro
                 85                  90                  95
Pro Gly Cys Thr Val Thr Ala Lys Lys Ser Leu Lys Tyr Val Pro Phe
            100                 105                 110
Leu Gly Trp Phe Met Ala Leu Ser Gly Thr Tyr Phe Leu Asp Arg Ser
            115                 120                 125
Lys Arg Gln Glu Ala Ile Asp Thr Leu Asn Lys Gly Leu Glu Asn Val
        130                 135                 140
Lys Lys Asn Lys Arg Ala Leu Trp Val Phe Pro Glu Gly Thr Arg Ser
145                 150                 155                 160
Tyr Thr Ser Glu Leu Thr Met Leu Pro Phe Lys Lys Gly Ala Phe His
                165                 170                 175
Leu Ala Gln Gln Gly Lys Ile Pro Ile Val Pro Val Val Val Ser Asn
            180                 185                 190
Thr Ser Thr Leu Val Ser Pro Lys Tyr Gly Val Phe Asn Arg Gly Cys
        195                 200                 205
Met Ile Val Arg Ile Leu Lys Pro Ile Ser Thr Glu Asn Leu Thr Lys
    210                 215                 220
Asp Lys Ile Gly Glu Phe Ala Glu Lys Val Arg Asp Gln Met Val Asp
225                 230                 235                 240
Thr Leu Lys Glu Ile Gly Tyr Ser Pro Ala Ile Asn Asp Thr Thr Leu
                245                 250                 255
Pro Pro Gln Ala Ile Glu Tyr Ala Ala Leu Gln His Asp Lys Lys Val
            260                 265                 270
Asn Lys Lys Ile Lys Asn Glu Pro Val Pro Ser Val Ser Ile Ser Asn
        275                 280                 285
Asp Val Asn Thr His Asn Glu Gly Ser Ser Val Lys Lys Met His
    290                 295                 300
```

<210> SEQ ID NO 4
<211> LENGTH: 245
<212> TYPE: PRT
<213> ORGANISM: Escheria coli

```
<400> SEQUENCE: 4

Met Leu Tyr Ile Phe Arg Leu Ile Ile Thr Val Ile Tyr Ser Ile Leu
 1               5                  10                  15

Val Cys Val Phe Gly Ser Ile Tyr Cys Leu Phe Ser Pro Arg Asn Pro
                20                  25                  30

Lys His Val Ala Thr Phe Gly His Met Phe Gly Arg Leu Ala Pro Leu
            35                  40                  45

Phe Gly Leu Lys Val Glu Cys Arg Lys Pro Thr Asp Ala Glu Ser Tyr
        50                  55                  60

Gly Asn Ala Ile Tyr Ile Ala Asn His Gln Asn Asn Tyr Asp Met Val
 65                 70                  75                  80

Thr Ala Ser Asn Ile Val Gln Pro Pro Thr Val Thr Val Gly Lys Lys
                85                  90                  95

Ser Leu Leu Trp Ile Pro Phe Phe Gly Gln Leu Tyr Trp Leu Thr Gly
                100                 105                 110

Asn Leu Leu Ile Asp Arg Asn Asn Arg Thr Lys Ala His Gly Thr Ile
            115                 120                 125

Ala Glu Val Val Asn His Phe Lys Lys Arg Ile Ser Ile Trp Met
130                 135                 140

Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
                180                 185                 190

Asn Gly Leu Val Ile Val Glu Met Leu Pro Pro Ile Asp Val Ser Gln
            195                 200                 205

Tyr Gly Lys Asp Gln Val Arg Glu Leu Ala Ala His Cys Arg Ser Ile
        210                 215                 220

Met Glu Gln Lys Ile Ala Glu Leu Asp Lys Glu Val Ala Glu Arg Glu
225                 230                 235                 240

Ala Ala Gly Lys Val
                245

<210> SEQ ID NO 5
<211> LENGTH: 374
<212> TYPE: PRT
<213> ORGANISM: Zea mays

<400> SEQUENCE: 5

Met Ala Ile Pro Leu Val Leu Val Leu Pro Leu Gly Leu Leu Phe
 1               5                  10                  15

Leu Leu Ser Gly Leu Ile Val Asn Ala Ile Gln Ala Val Leu Phe Val
                20                  25                  30

Thr Ile Arg Pro Phe Ser Lys Ser Phe Tyr Arg Arg Ile Asn Arg Phe
            35                  40                  45

Leu Ala Glu Leu Leu Trp Leu Gln Leu Val Trp Val Asp Trp Trp
        50                  55                  60

Ala Gly Val Lys Val Gln Leu His Ala Asp Glu Thr Tyr Arg Ser
 65                 70                  75                  80

Met Gly Lys Glu His Ala Leu Ile Ile Ser Asn His Arg Ser Asp Ile
                85                  90                  95

Asp Trp Leu Ile Gly Trp Ile Leu Ala Gln Arg Ser Gly Cys Leu Gly
                100                 105                 110
```

```
Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
        130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
                165                 170                 175

Thr Pro Ala Lys Leu Leu Ala Ala Gln Glu Tyr Ala Ala Ser Gln Gly
                180                 185                 190

Leu Pro Ala Pro Arg Asn Val Leu Ile Pro Arg Thr Lys Gly Phe Val
                195                 200                 205

Ser Ala Val Ser Ile Met Arg Asp Phe Val Pro Ala Ile Tyr Asp Thr
        210                 215                 220

Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                245                 250                 255

Met Ser Glu Met Pro Lys Ser Asp Glu Asp Val Ser Lys Trp Cys Lys
                260                 265                 270

Asp Ile Phe Val Ala Lys Asp Ala Leu Leu Asp Lys His Leu Ala Thr
        275                 280                 285

Gly Thr Phe Asp Glu Glu Ile Arg Pro Ile Gly Arg Pro Val Lys Ser
        290                 295                 300

Leu Leu Val Thr Leu Phe Trp Ser Cys Leu Leu Phe Gly Ala Ile
305                 310                 315                 320

Glu Phe Phe Lys Trp Thr Gln Leu Leu Ser Thr Trp Arg Gly Val Ala
                325                 330                 335

Phe Thr Ala Ala Gly Met Ala Leu Val Thr Gly Val Met His Val Phe
                340                 345                 350

Ile Met Phe Ser Gln Ala Glu Arg Ser Ser Ser Ala Arg Ala Ala Arg
        355                 360                 365

Asn Arg Val Lys Lys Glu
        370

<210> SEQ ID NO 6
<211> LENGTH: 1383
<212> TYPE: DNA
<213> ORGANISM: Homo sapiens
<220> FEATURE:
<221> NAME/KEY: CDS
<222> LOCATION: (40)..(876)
<220> FEATURE:
<221> NAME/KEY: modified_base
<222> LOCATION: (1127)
<223> OTHER INFORMATION: a, t, c, g, other or unknown
<220> FEATURE:
<221> NAME/KEY: modified_base
<222> LOCATION: (1134)
<223> OTHER INFORMATION: a, t, c, g, other or unknown

<400> SEQUENCE: 6
ggagcgagct ggcggcgccg tcgggcgccg ggccgggcc atg gag ctg tgg ccg       54
                                          Met Glu Leu Trp Pro
                                            1               5 tgt ctg gcc gcg gcg ctg ctg ttg ctg ctg ctg gtg cag ctg agc         102
Cys Leu Ala Ala Ala Leu Leu Leu Leu Leu Leu Val Gln Leu Ser
             10                  15                  20 cgc gcg gcc gag ttc tac gcc aag gtc gcc ctg tac tgc gcg ctg tgc    150
```

-continued

| | | |
|---|---|---|
| Arg Ala Ala Glu Phe Tyr Ala Lys Val Ala Leu Tyr Cys Ala Leu Cys<br>                 25                     30                    35 | | |
| ttc acg gtg tcc gcc gtg gcc tcg ctc gtc tgc ctg ctg tgc cac ggc<br>Phe Thr Val Ser Ala Val Ala Ser Leu Val Cys Leu Leu Cys His Gly<br>            40                     45                     50 | 198 |
| ggc cgg acg gtg gag aac atg agc atc atc ggc tgg ttc gtg cga agc<br>Gly Arg Thr Val Glu Asn Met Ser Ile Ile Gly Trp Phe Val Arg Ser<br>     55                     60                     65 | 246 |
| ttc aag tac ttt tac ggg ctc cgc ttc gag gtg cgg gac ccg cgc agg<br>Phe Lys Tyr Phe Tyr Gly Leu Arg Phe Glu Val Arg Asp Pro Arg Arg<br> 70                    75                     80                    85 | 294 |
| ctg cag gag gcc cgt ccc tgt gtc atc gtc tcc aac cac cag agc atc<br>Leu Gln Glu Ala Arg Pro Cys Val Ile Val Ser Asn His Gln Ser Ile<br>                  90                     95                   100 | 342 |
| ctg gac atg atg ggc ctc atg gag gtc ctt ccg gag cgc tgc gtg cag<br>Leu Asp Met Met Gly Leu Met Glu Val Leu Pro Glu Arg Cys Val Gln<br>                 105                   110               115 | 390 |
| atc gcc aag cgg gag ctg ctc ttc ctg ggg ccc gtg ggc ctc atc atg<br>Ile Ala Lys Arg Glu Leu Leu Phe Leu Gly Pro Val Gly Leu Ile Met<br>       120                 125                   130 | 438 |
| tac ctc ggg ggc gtc ttc ttc atc aac cgg cag cgc tct agc act gcc<br>Tyr Leu Gly Gly Val Phe Phe Ile Asn Arg Gln Arg Ser Ser Thr Ala<br> 135                   140                   145 | 486 |
| atg aca gtg atg gcc gac ctg ggc gag cgc atg gtc agg gag aac ctc<br>Met Thr Val Met Ala Asp Leu Gly Glu Arg Met Val Arg Glu Asn Leu<br>150                   155                   160               165 | 534 |
| aaa gtg tgg atc tat ccc gag ggt act cgc aac gac aat ggg gac ctg<br>Lys Val Trp Ile Tyr Pro Glu Gly Thr Arg Asn Asp Asn Gly Asp Leu<br>                 170                   175               180 | 582 |
| ctg cct ttt aag aag ggc gcc ttc tac ctg gca gtc cag gca cag gtg<br>Leu Pro Phe Lys Lys Gly Ala Phe Tyr Leu Ala Val Gln Ala Gln Val<br>             185                   190                  195 | 630 |
| ccc atc gtc ccc gtg gtg tac tct tcc ttc tcc tcc ttc tac aac acc<br>Pro Ile Val Pro Val Val Tyr Ser Ser Phe Ser Ser Phe Tyr Asn Thr<br>                 200                   205                 210 | 678 |
| aag aag aag ttc ttc act tca gga aca gtc aca gtg cag gtg ctg gaa<br>Lys Lys Lys Phe Phe Thr Ser Gly Thr Val Thr Val Gln Val Leu Glu<br>215                   220                   225 | 726 |
| gcc atc ccc acc agc ggc ctc act gcg gcg gac gtc cct gcg ctc gtg<br>Ala Ile Pro Thr Ser Gly Leu Thr Ala Ala Asp Val Pro Ala Leu Val<br>230                   235                   240               245 | 774 |
| gac acc tgc cac cgg gcc atg agg acc acc ttc ctc cac atc tcc aag<br>Asp Thr Cys His Arg Ala Met Arg Thr Thr Phe Leu His Ile Ser Lys<br>             250                   255                   260 | 822 |
| acc ccc cag gag aac ggg gcc act gcg ggg tct ggc gtg cag ccg gcc<br>Thr Pro Gln Glu Asn Gly Ala Thr Ala Gly Ser Gly Val Gln Pro Ala<br>                 265                   270               275 | 870 |
| cag tag cccagaccac ggcagggcat gacctgggga gggcaggtgg aagccgatgg<br>Gln | 926 |
| ctggaggatg ggcagagggg actcctcccg gcttccaaat accactctgt ccggctcccc | 986 |
| cagctctcac tcagcccggg aagcaggaag ccccttctgt cactggtctc agacacaggc | 1046 |
| ccctggtgtc ccctgcaggg ggctcagctg gaccctcccc gggctcgagg gcagggactc | 1106 |
| gcgcccacgg cacctctggg ngctgggntg ataaagatga ggcttgcggc tgtgcccgc | 1166 |
| tggtgggctg agccacaagg ccccgatgg cccaggagca gatgggagga ccccgaggcc | 1226 |
| aggagtccca gactcacgca ccctgggcca caggagccg ggaatcgggg cctgctgctc | 1286 |
| ctgctggcct gaagaatctg tggggtcagc actgtactcc gttgctgttt ttttataaac | 1346 |

```
acactcttgg aaaaaaaaaa aaaaaaaaaa aaaaaaa                    1383
```

<210> SEQ ID NO 7
<211> LENGTH: 278
<212> TYPE: PRT
<213> ORGANISM: Homo sapiens

<400> SEQUENCE: 7

```
Met Glu Leu Trp Pro Cys Leu Ala Ala Ala Leu Leu Leu Leu Leu
 1               5                  10                  15

Leu Val Gln Leu Ser Arg Ala Ala Glu Phe Tyr Ala Lys Val Ala Leu
             20                  25                  30

Tyr Cys Ala Leu Cys Phe Thr Val Ser Ala Val Ala Ser Leu Val Cys
         35                  40                  45

Leu Leu Cys His Gly Gly Arg Thr Val Glu Asn Met Ser Ile Ile Gly
     50                  55                  60

Trp Phe Val Arg Ser Phe Lys Tyr Phe Tyr Gly Leu Arg Phe Glu Val
 65                  70                  75                  80

Arg Asp Pro Arg Arg Leu Gln Glu Ala Arg Pro Cys Val Ile Val Ser
                 85                  90                  95

Asn His Gln Ser Ile Leu Asp Met Met Gly Leu Met Glu Val Leu Pro
            100                 105                 110

Glu Arg Cys Val Gln Ile Ala Lys Arg Glu Leu Leu Phe Leu Gly Pro
            115                 120                 125

Val Gly Leu Ile Met Tyr Leu Gly Gly Val Phe Phe Ile Asn Arg Gln
            130                 135                 140

Arg Ser Ser Thr Ala Met Thr Val Met Ala Asp Leu Gly Glu Arg Met
145                 150                 155                 160

Val Arg Glu Asn Leu Lys Val Trp Ile Tyr Pro Glu Gly Thr Arg Asn
                165                 170                 175

Asp Asn Gly Asp Leu Leu Pro Phe Lys Lys Gly Ala Phe Tyr Leu Ala
            180                 185                 190

Val Gln Ala Gln Val Pro Ile Val Pro Val Val Tyr Ser Ser Phe Ser
            195                 200                 205

Ser Phe Tyr Asn Thr Lys Lys Lys Phe Phe Thr Ser Gly Thr Val Thr
        210                 215                 220

Val Gln Val Leu Glu Ala Ile Pro Thr Ser Gly Leu Thr Ala Ala Asp
225                 230                 235                 240

Val Pro Ala Leu Val Asp Thr Cys His Arg Ala Met Arg Thr Thr Phe
                245                 250                 255

Leu His Ile Ser Lys Thr Pro Gln Glu Asn Gly Ala Thr Ala Gly Ser
            260                 265                 270

Gly Val Gln Pro Ala Gln
        275
```

<210> SEQ ID NO 8
<211> LENGTH: 248
<212> TYPE: PRT
<213> ORGANISM: Haemophilus influenzae

<400> SEQUENCE: 8

```
Met Leu Lys Leu Leu Arg Ile Phe Leu Val Leu Ile Cys Cys Ile Leu
 1               5                  10                  15

Ile Cys Val Leu Gly Thr Ile Tyr Ser Phe Ile Arg Phe Lys Asn Pro
             20                  25                  30
```

```
Ser Asn Val Gly Ile Val Ala Arg Trp Phe Gly Arg Leu Phe Thr Tyr
            35                  40                  45

Pro Leu Phe Gly Leu Lys Val Glu His Arg Ile Pro Gln Asp Gln Lys
 50                  55                  60

Gln Ile Ser Arg Ala Ile Tyr Ile Gly Asn His Gln Asn Asn Tyr Asp
 65                  70                  75                  80

Met Val Thr Ile Ser Tyr Met Val Gln Pro Arg Thr Val Ser Val Gly
                85                  90                  95

Lys Lys Ser Leu Ile Trp Ile Pro Phe Phe Thr Gly Ile Leu Tyr
                100                 105                 110

Trp Val Thr Gly Asn Ile Phe Leu Asp Arg Glu Asn Arg Thr Lys Ala
                115                 120                 125

His Asn Thr Met Ser Gln Leu Ala Arg Arg Ile Asn Glu Asp Asn Leu
    130                 135                 140

Ser Ile Trp Met Phe Pro Glu Gly Thr Arg Asn Arg Gly Arg Gly Leu
145                 150                 155                 160

Leu Pro Phe Lys Thr Gly Ala Phe Thr Phe His Ala Ala Ile Ser Ala
                165                 170                 175

Gly Val Pro Ile Ile Pro Val Val Cys Ser Ser Thr His Asn Lys Ile
                180                 185                 190

Asn Leu Asn Arg Trp Asp Asn Gly Lys Val Ile Cys Glu Ile Met Asp
                195                 200                 205

Pro Ile Asp Val Ser Gly Tyr Thr Lys Asp Asn Val Arg Asp Leu Ala
    210                 215                 220

Ala Tyr Cys His Phe Thr Asp Leu Met Glu Lys Arg Ile Ala Glu Leu
225                 230                 235                 240

Asp Glu Glu Ile Ala Lys Gly Asn
                245

<210> SEQ ID NO 9
<211> LENGTH: 253
<212> TYPE: PRT
<213> ORGANISM: Salmonella typhimurium

<400> SEQUENCE: 9

Met Leu Tyr Ile Phe Arg Leu Ile Val Thr Val Ile Tyr Ser Ile Leu
 1               5                   10                  15

Val Cys Val Phe Gly Ser Ile Tyr Cys Leu Phe Ser Pro Arg Asn Pro
                20                  25                  30

Lys His Val Ala Thr Phe Gly His Met Phe Gly Arg Leu Phe Thr Ala
            35                  40                  45

Pro Leu Phe Gly Leu Lys Val Glu Cys Arg Lys Pro Ala Asp Ala Glu
 50                  55                  60

Asn Tyr Gly Asn Ala Ile Tyr Ile Ala Asn His Gln Asn Asn Tyr Asp
 65                  70                  75                  80

Met Val Thr Ala Ala Asn Ile Val Gln Pro Pro Thr Val Thr Val Gly
                85                  90                  95

Lys Lys Ser Leu Leu Trp Ile Pro Phe Phe Thr Gly Gln Leu Tyr
                100                 105                 110

Trp Leu Thr Gly Asn Leu Leu Ile Asp Arg Asn Asn Arg Ala Lys Ala
                115                 120                 125

His Ser Thr Ile Ala Ala Val Val Asn His Phe Lys Lys Arg Arg Ile
    130                 135                 140

Ser Ile Trp Met Phe Pro Glu Gly Thr Arg Ser Arg Gly Arg Gly Leu
145                 150                 155                 160
```

```
Leu Pro Phe Lys Thr Gly Ala Phe Thr Phe His Ala Ala Ile Ala Ala
                165                 170                 175

Gly Val Pro Ile Ile Pro Val Cys Val Ser Asn Thr Ser Asn Lys Val
            180                 185                 190

Asn Leu Asn Arg Leu Asn Asn Gly Leu Val Ile Val Glu Met Leu Pro
        195                 200                 205

Pro Val Asp Val Ser Glu Tyr Gly Lys Asp Gln Val Arg Glu Leu Ala
    210                 215                 220

Ala His Cys Arg Phe Thr Ala Leu Met Glu Gln Lys Ile Ala Glu Leu
225                 230                 235                 240

Asp Lys Glu Val Ala Glu Arg Glu Ala Thr Gly Lys Val
                245                 250

<210> SEQ ID NO 10
<211> LENGTH: 289
<212> TYPE: PRT
<213> ORGANISM: Lupinus douglassi

<400> SEQUENCE: 10

Met Ala Lys Thr Arg Thr Ser Ser Leu Arg Asn Arg Arg Gln Leu Lys
1               5                   10                  15

Pro Ala Val Ala Ala Thr Ala Asp Asp Lys Asp Gly Val Phe Met
            20                  25                  30

Val Leu Leu Ser Cys Phe Lys Ile Phe Val Cys Phe Ala Phe Thr Val
        35                  40                  45

Val Leu Ile Thr Ala Val Ala Trp Gly Leu Ile Met Val Leu Leu Leu
    50                  55                  60

Pro Trp Pro Tyr Met Arg Ile Arg Leu Gly Asn Leu Tyr Gly His Ile
65                  70                  75                  80

Ile Gly Gly Leu Val Ile Trp Ile Tyr Gly Ile Pro Ile Lys Ile Gln
                85                  90                  95

Gly Ser Glu His Thr Lys Lys Arg Ala Ile Phe Thr Tyr Ile Ser Asn
            100                 105                 110

His Ala Ser Pro Ile Asp Ala Phe Phe Val Met Trp Leu Ala Pro Ile
        115                 120                 125

Gly Thr Val Gly Val Ala Lys Lys Glu Val Ile Trp Tyr Pro Leu Leu
    130                 135                 140

Gly Gln Leu Tyr Thr Leu Ala His His Ile Arg Ile Asp Arg Ser Asn
145                 150                 155                 160

Pro Ala Ala Ala Ile Gln Ser Phe Thr Met Lys Glu Ala Val Arg Val
                165                 170                 175

Ile Thr Glu Lys Asn Leu Ser Leu Ile Met Phe Pro Glu Gly Thr Arg
            180                 185                 190

Ser Gly Asp Gly Arg Leu Leu Pro Phe Lys Lys Gly Phe Val His Leu
        195                 200                 205

Ala Leu Gln Ser His Leu Pro Ile Val Pro Met Ile Leu Thr Gly Thr
    210                 215                 220

His Leu Ala Trp Phe Thr Arg Lys Gly Thr Phe Arg Val Arg Pro Val
225                 230                 235                 240

Pro Ile Thr Val Lys Tyr Leu Pro Pro Ile Asn Thr Asp Asp Trp Thr
                245                 250                 255

Val Asp Lys Ile Asp Asp Tyr Val Lys Met Ile His Asp Ile Tyr Val
            260                 265                 270

Arg Asn Leu Pro Ala Ser Gln Lys Pro Leu Gly Ser Thr Asn Arg Ser
```

275                 280                 285
Lys

<210> SEQ ID NO 11
<211> LENGTH: 318
<212> TYPE: PRT
<213> ORGANISM: Cocos nucifera

<400> SEQUENCE: 11

Met Asp Ala Ser Gly Ala Ser Ser Phe Leu Arg Gly Arg Cys Leu Glu
 1               5                  10                  15

Ser Cys Phe Lys Ala Ser Phe Gly Met Ser Gln Pro Lys Asp Ala Ala
                20                  25                  30

Gly Gln Pro Ser Arg Arg Pro Ala Asp Ala Asp Phe Phe Thr Val
                35                  40                  45

Asp Asp Asp Arg Trp Ile Thr Val Ile Leu Ser Val Val Arg Ile Ala
        50                  55                  60

Ala Cys Phe Leu Ser Met Met Val Thr Thr Ile Val Trp Asn Met Ile
 65                  70                  75                  80

Met Leu Ile Leu Leu Pro Trp Pro Tyr Ala Arg Ile Arg Gln Gly Asn
                85                  90                  95

Leu Tyr Gly His Val Thr Gly Arg Met Leu Phe Thr Met Trp Ile Leu
                100                 105                 110

Gly Asn Pro Ile Thr Ile Glu Gly Ser Glu Phe Ser Asn Thr Arg Ala
            115                 120                 125

Ile Tyr Ile Cys Asn His Ala Ser Leu Val Asp Ile Phe Leu Ile Met
        130                 135                 140

Trp Leu Ile Pro Lys Gly Thr Val Thr Ile Ala Lys Lys Glu Ile Ile
145                 150                 155                 160

Trp Tyr Pro Leu Phe Gly Gln Phe Thr Leu Tyr Val Leu Ala Asn His
                165                 170                 175

Gln Arg Ile Asp Arg Ser Asn Pro Ser Ala Ala Ile Glu Ser Ile Lys
                180                 185                 190

Glu Val Ala Arg Ala Val Val Lys Lys Asn Leu Ser Leu Ile Ile Phe
            195                 200                 205

Pro Glu Gly Thr Arg Ser Lys Thr Gly Arg Leu Leu Pro Phe Lys Lys
        210                 215                 220

Gly Phe Ile His Phe Thr Ile Ala Leu Gln Thr Arg Leu Pro Ile Val
225                 230                 235                 240

Pro Met Val Leu Thr Gly Thr His Leu Ala Trp Arg Lys Asn Ser Leu
                245                 250                 255

Arg Val Arg Pro Ala Pro Ile Thr Val Lys Tyr Phe Ser Pro Ile Lys
                260                 265                 270

Thr Asp Asp Trp Glu Glu Glu Lys Ile Asn His Tyr Val Glu Met Ile
            275                 280                 285

His Phe Thr Ala Leu Tyr Val Asp His Leu Pro Glu Ser Gln Lys Pro
        290                 295                 300

Leu Val Ser Lys Gly Arg Asp Ala Ser Gly Arg Ser Asn Ser
305                 310                 315

<210> SEQ ID NO 12
<211> LENGTH: 1660
<212> TYPE: DNA
<213> ORGANISM: Homo sapiens
<220> FEATURE:
<221> NAME/KEY: CDS

<222> LOCATION: (184)..(1311)

<400> SEQUENCE: 12

```
tctatgaaac caacatacat ggcgtttgca tcacagttgg agtcagatgt gagcccggag    60
ggcaggtgtc tggcttgtcc acccggaagc cctgagggca gctgttccca ctggctctgc   120
tgaccttgtg ccttggacgg ctgtcctcag cgagggccg tgcacccgct cctgagcagc    180
```

| | | | | | | | | | | | | | | | | |
|---|---|---|---|---|---|---|---|---|---|---|---|---|---|---|---|---|
| gcc | atg | ggc | ctg | ctg | gcc | ttc | ctg | aag | acc | cag | ttc | gtg | ctg | cac | ctg | 228 |
| | Met | Gly | Leu | Leu | Ala | Phe | Leu | Lys | Thr | Gln | Phe | Val | Leu | His | Leu | |
| | 1 | | | 5 | | | | | 10 | | | | | 15 | | |

| ctg | gtc | ggc | ttt | gtc | ttc | gtg | gtg | agt | ggt | ctg | gtc | atc | aac | ttc | gtc | 276 |
|---|---|---|---|---|---|---|---|---|---|---|---|---|---|---|---|---|
| Leu | Val | Gly | Phe | Val | Phe | Val | Val | Ser | Gly | Leu | Val | Ile | Asn | Phe | Val | |
| | | 20 | | | | | 25 | | | | | 30 | | | | |

| cag | ctg | tgc | acg | ctg | gcg | ctc | tgg | ccg | gtc | agc | aag | cag | ctc | tac | cgc | 324 |
|---|---|---|---|---|---|---|---|---|---|---|---|---|---|---|---|---|
| Gln | Leu | Cys | Thr | Leu | Ala | Leu | Trp | Pro | Val | Ser | Lys | Gln | Leu | Tyr | Arg | |
| | | | 35 | | | | | 40 | | | | | 45 | | | |

| cgc | ctc | aac | tgc | cgc | ctc | gca | tac | tca | ctc | tgg | agc | caa | ctg | gtc | atg | 372 |
|---|---|---|---|---|---|---|---|---|---|---|---|---|---|---|---|---|
| Arg | Leu | Asn | Cys | Arg | Leu | Ala | Tyr | Ser | Leu | Trp | Ser | Gln | Leu | Val | Met | |
| | 50 | | | | | 55 | | | | | 60 | | | | | |

| ctg | ctg | gag | tgg | tgg | tcc | tgc | acg | gag | tgt | aca | ctg | ttc | acg | gac | cag | 420 |
|---|---|---|---|---|---|---|---|---|---|---|---|---|---|---|---|---|
| Leu | Leu | Glu | Trp | Trp | Ser | Cys | Thr | Glu | Cys | Thr | Leu | Phe | Thr | Asp | Gln | |
| 65 | | | | | 70 | | | | | 75 | | | | | | |

| gcc | acg | gta | gag | cgc | ttt | ggg | aag | gag | cac | gca | gtc | atc | atc | ctc | aac | 468 |
|---|---|---|---|---|---|---|---|---|---|---|---|---|---|---|---|---|
| Ala | Thr | Val | Glu | Arg | Phe | Gly | Lys | Glu | His | Ala | Val | Ile | Ile | Leu | Asn | |
| 80 | | | | | 85 | | | | | 90 | | | | | 95 | |

| cac | aac | ttc | gag | atc | gac | ttc | ctc | tgt | ggg | tgg | acc | atg | tgt | gag | cgc | 516 |
|---|---|---|---|---|---|---|---|---|---|---|---|---|---|---|---|---|
| His | Asn | Phe | Glu | Ile | Asp | Phe | Leu | Cys | Gly | Trp | Thr | Met | Cys | Glu | Arg | |
| | | | | 100 | | | | | 105 | | | | | 110 | | |

| ttc | gga | gtg | ctg | ggg | agc | tcc | aag | gtc | ctc | gct | aag | aag | gag | ctg | ctc | 564 |
|---|---|---|---|---|---|---|---|---|---|---|---|---|---|---|---|---|
| Phe | Gly | Val | Leu | Gly | Ser | Ser | Lys | Val | Leu | Ala | Lys | Lys | Glu | Leu | Leu | |
| | | | 115 | | | | | 120 | | | | | 125 | | | |

| tac | gtg | ccc | ctc | atc | ggc | tgg | acg | tgg | tac | ttt | ctg | gag | att | gtg | ttc | 612 |
|---|---|---|---|---|---|---|---|---|---|---|---|---|---|---|---|---|
| Tyr | Val | Pro | Leu | Ile | Gly | Trp | Thr | Trp | Tyr | Phe | Leu | Glu | Ile | Val | Phe | |
| | 130 | | | | | 135 | | | | | 140 | | | | | |

| tgc | aag | cgg | aag | tgg | gag | gag | gac | cgg | gac | acc | gtg | gtc | gaa | ggg | ctg | 660 |
|---|---|---|---|---|---|---|---|---|---|---|---|---|---|---|---|---|
| Cys | Lys | Arg | Lys | Trp | Glu | Glu | Asp | Arg | Asp | Thr | Val | Val | Glu | Gly | Leu | |
| 145 | | | | | 150 | | | | | 155 | | | | | | |

| agg | cgc | ctg | tcg | gac | tac | ccc | gag | tac | atg | tgg | ttt | ctc | ctg | tac | tgc | 708 |
|---|---|---|---|---|---|---|---|---|---|---|---|---|---|---|---|---|
| Arg | Arg | Leu | Ser | Asp | Tyr | Pro | Glu | Tyr | Met | Trp | Phe | Leu | Leu | Tyr | Cys | |
| 160 | | | | | 165 | | | | | 170 | | | | | 175 | |

| gag | ggg | acg | cgc | ttc | acg | gag | acc | aag | cac | cgc | gtt | agc | atg | gag | gtg | 756 |
|---|---|---|---|---|---|---|---|---|---|---|---|---|---|---|---|---|
| Glu | Gly | Thr | Arg | Phe | Thr | Glu | Thr | Lys | His | Arg | Val | Ser | Met | Glu | Val | |
| | | | 180 | | | | | 185 | | | | | 190 | | | |

| gcg | gct | gct | aag | ggg | ctt | cct | gtc | ctc | aag | tac | cac | ctg | ctg | ccg | cgg | 804 |
|---|---|---|---|---|---|---|---|---|---|---|---|---|---|---|---|---|
| Ala | Ala | Ala | Lys | Gly | Leu | Pro | Val | Leu | Lys | Tyr | His | Leu | Leu | Pro | Arg | |
| | | | 195 | | | | | 200 | | | | | 205 | | | |

| acc | aag | ggc | ttc | acc | acc | gca | gtc | aag | tgc | ctc | cgg | ggg | aca | gtc | gca | 852 |
|---|---|---|---|---|---|---|---|---|---|---|---|---|---|---|---|---|
| Thr | Lys | Gly | Phe | Thr | Thr | Ala | Val | Lys | Cys | Leu | Arg | Gly | Thr | Val | Ala | |
| | | 210 | | | | | 215 | | | | | 220 | | | | |

| gct | gtc | tat | gat | gta | acc | ctg | aac | ttc | aga | gga | aac | aag | aac | ccg | tcc | 900 |
|---|---|---|---|---|---|---|---|---|---|---|---|---|---|---|---|---|
| Ala | Val | Tyr | Asp | Val | Thr | Leu | Asn | Phe | Arg | Gly | Asn | Lys | Asn | Pro | Ser | |
| 225 | | | | | 230 | | | | | 235 | | | | | | |

| ctg | ctg | ggg | atc | ctc | tac | ggg | aag | aag | tac | gag | gcg | gac | atg | tgc | gtg | 948 |
|---|---|---|---|---|---|---|---|---|---|---|---|---|---|---|---|---|
| Leu | Leu | Gly | Ile | Leu | Tyr | Gly | Lys | Lys | Tyr | Glu | Ala | Asp | Met | Cys | Val | |
| 240 | | | | | 245 | | | | | 250 | | | | | 255 | |

| agg | aga | ttt | cct | ctg | gaa | gac | atc | ccg | ctg | gat | gaa | aag | gaa | gca | gct | 996 |
|---|---|---|---|---|---|---|---|---|---|---|---|---|---|---|---|---|
| Arg | Arg | Phe | Pro | Leu | Glu | Asp | Ile | Pro | Leu | Asp | Glu | Lys | Glu | Ala | Ala | |
| | | | | 260 | | | | | 265 | | | | | 270 | | |

```
cag tgg ctt cat aaa ctg tac cag gag aag gac gcg ctc cag gag ata    1044
```

-continued

```
Gln Trp Leu His Lys Leu Tyr Gln Glu Lys Asp Ala Leu Gln Glu Ile
                275                 280                 285 tat aat cag aag ggc atg ttt cca ggg gag cag ttt aag cct gcc cgg      1092
Tyr Asn Gln Lys Gly Met Phe Pro Gly Glu Gln Phe Lys Pro Ala Arg
            290                 295                 300 agg ccg tgg acc ctc ctg aac ttc ctg tcc tgg gcc acc att ctc ctg      1140
Arg Pro Trp Thr Leu Leu Asn Phe Leu Ser Trp Ala Thr Ile Leu Leu
        305                 310                 315 tct ccc ctc ttc agt ttt gtc ttg ggc gtc ttt gcc agc gga tca cct      1188
Ser Pro Leu Phe Ser Phe Val Leu Gly Val Phe Ala Ser Gly Ser Pro
320                 325                 330                 335 ctc ctg atc ctg act ttc ttg ggg ttt gtg gga gca gct tcc ttt gga      1236
Leu Leu Ile Leu Thr Phe Leu Gly Phe Val Gly Ala Ala Ser Phe Gly
                340                 345                 350 gtt cgc aga ctg ata gga gta act gag ata gaa aaa ggc tcc agc tac      1284
Val Arg Arg Leu Ile Gly Val Thr Glu Ile Glu Lys Gly Ser Ser Tyr
            355                 360                 365 gga aac caa gag ttt aag aaa aag gaa taattaatgg ctgtgactga            1331
Gly Asn Gln Glu Phe Lys Lys Lys Glu
        370                 375 acacacgcgg ccctgacggt ggtatccagt taactcaaaa ccaacacaca gagtgcagga    1391
aaagacaatt agaaactatt tttcttatta actggtgact aatattaaca aaacttgagc    1451
caagagtaaa gaattcagaa ggcctgtcag gtgaagtctt cagcctccca cagcgcaggg    1511
tcccagcatc tccacgcgcg cccgtgggag gtgggtccgg ccggagaggc ctcccgcgga    1571
cgccgtctct ccagaactcc gcttccaaga gggacctttg gctgctttct ctccttaaac    1631
ttagatcaaa ttttaaaaaa aaaaaaaaa                                       1660
```

```
<210> SEQ ID NO 13
<211> LENGTH: 376
<212> TYPE: PRT
<213> ORGANISM: Homo sapiens

<400> SEQUENCE: 13

Met Gly Leu Leu Ala Phe Leu Lys Thr Gln Phe Val Leu His Leu Leu
1               5                   10                  15

Val Gly Phe Val Phe Val Val Ser Gly Leu Val Ile Asn Phe Val Gln
            20                  25                  30

Leu Cys Thr Leu Ala Leu Trp Pro Val Ser Lys Gln Leu Tyr Arg Arg
        35                  40                  45

Leu Asn Cys Arg Leu Ala Tyr Ser Leu Trp Ser Gln Leu Val Met Leu
    50                  55                  60

Leu Glu Trp Trp Ser Cys Thr Glu Cys Thr Leu Phe Thr Asp Gln Ala
65                  70                  75                  80

Thr Val Glu Arg Phe Gly Lys Glu His Ala Val Ile Ile Leu Asn His
                85                  90                  95

Asn Phe Glu Ile Asp Phe Leu Cys Gly Trp Thr Met Cys Glu Arg Phe
            100                 105                 110

Gly Val Leu Gly Ser Ser Lys Val Leu Ala Lys Glu Leu Leu Tyr
        115                 120                 125

Val Pro Leu Ile Gly Trp Thr Trp Tyr Phe Leu Glu Ile Val Phe Cys
    130                 135                 140

Lys Arg Lys Trp Glu Glu Asp Arg Asp Thr Val Val Glu Gly Leu Arg
145                 150                 155                 160

Arg Leu Ser Asp Tyr Pro Glu Tyr Met Trp Phe Leu Leu Tyr Cys Glu
                165                 170                 175
```

```
Gly Thr Arg Phe Thr Glu Thr Lys His Arg Val Ser Met Glu Val Ala
            180                 185                 190

Ala Ala Lys Gly Leu Pro Val Leu Lys Tyr His Leu Leu Pro Arg Thr
        195                 200                 205

Lys Gly Phe Thr Thr Ala Val Lys Cys Leu Arg Gly Thr Val Ala Ala
        210                 215                 220

Val Tyr Asp Val Thr Leu Asn Phe Arg Gly Asn Lys Asn Pro Ser Leu
225                 230                 235                 240

Leu Gly Ile Leu Tyr Gly Lys Lys Tyr Glu Ala Asp Met Cys Val Arg
                245                 250                 255

Arg Phe Pro Leu Glu Asp Ile Pro Leu Asp Glu Lys Glu Ala Ala Gln
        260                 265                 270

Trp Leu His Lys Leu Tyr Gln Glu Lys Asp Ala Leu Gln Glu Ile Tyr
        275                 280                 285

Asn Gln Lys Gly Met Phe Pro Gly Glu Gln Phe Lys Pro Ala Arg Arg
        290                 295                 300

Pro Trp Thr Leu Leu Asn Phe Leu Ser Trp Ala Thr Ile Leu Leu Ser
305                 310                 315                 320

Pro Leu Phe Ser Phe Val Leu Gly Val Phe Ala Ser Gly Ser Pro Leu
                325                 330                 335

Leu Ile Leu Thr Phe Leu Gly Phe Val Gly Ala Ala Ser Phe Gly Val
            340                 345                 350

Arg Arg Leu Ile Gly Val Thr Glu Ile Glu Lys Gly Ser Ser Tyr Gly
        355                 360                 365

Asn Gln Glu Phe Lys Lys Lys Glu
        370                 375

<210> SEQ ID NO 14
<211> LENGTH: 1523
<212> TYPE: DNA
<213> ORGANISM: Homo sapiens
<220> FEATURE:
<221> NAME/KEY: CDS
<222> LOCATION: (233)..(1174)

<400> SEQUENCE: 14
cacgctggcg ctctggccgg tcagcaagca gctctaccgc cgcctcaact gccgcctcgc        60
ctactcactc tggagcctag cacaaaacta gaagcaaccc aagcacctgt cactggagac       120
taattatgcg gcacccatac agggaccctc tgcggccatc atggagagcc ttcatcttgc       180
ccgtacagtt ttaagcgaaa aggaagtat acaacaaagt ccataactgg tc atg ctg       238
                                                          Met Leu
                                                            1 ctg gag tgg tgg tcc tgc acg gag tgt aca ctg ttc acg gac cag gcc        286
Leu Glu Trp Trp Ser Cys Thr Glu Cys Thr Leu Phe Thr Asp Gln Ala
      5                  10                  15 acg gta gag cgc ttt ggg aag gag cac gca gtc atc atc ctc aac cac        334
Thr Val Glu Arg Phe Gly Lys Glu His Ala Val Ile Ile Leu Asn His
         20                  25                  30 aac ttc gag atc gac ttc ctc tgt ggg tgg acc atg tgt gag cgc ttc        382
Asn Phe Glu Ile Asp Phe Leu Cys Gly Trp Thr Met Cys Glu Arg Phe
 35                  40                  45                  50 gga gtg ctg ggg agc tcc aag gtc ctc gct aag aag gag ctg ctc tac        430
Gly Val Leu Gly Ser Ser Lys Val Leu Ala Lys Lys Glu Leu Leu Tyr
             55                  60                  65 gtg ccc ctc atc ggc tgg acg tgg tac ttt ctg gag att gtg ttc tgc        478
Val Pro Leu Ile Gly Trp Thr Trp Tyr Phe Leu Glu Ile Val Phe Cys
         70                  75                  80
```

```
                    70                  75                  80
aag cgg aag tgg gag gag gac cgg gac acc gtg gtc gaa ggg ctg agg      526
Lys Arg Lys Trp Glu Glu Asp Arg Asp Thr Val Val Glu Gly Leu Arg
            85                  90                  95 cgc ctg tcg gac tac ccc gag tac atg tgg ttt ctc ctg tac tgc gag      574
Arg Leu Ser Asp Tyr Pro Glu Tyr Met Trp Phe Leu Leu Tyr Cys Glu
100                 105                 110 ggg acg cgc ttc acg gag acc aag cac cgc gtt agc atg gag gtg gcg      622
Gly Thr Arg Phe Thr Glu Thr Lys His Arg Val Ser Met Glu Val Ala
115                 120                 125                 130 gct gct aag ggg ctt cct gtc ctc aag tac cac ctg ctg ccg cgg acc      670
Ala Ala Lys Gly Leu Pro Val Leu Lys Tyr His Leu Leu Pro Arg Thr
                135                 140                 145 aag ggc ttc acc acc gca gtc aag tgc ctc cgg ggg aca gtc gca gct      718
Lys Gly Phe Thr Thr Ala Val Lys Cys Leu Arg Gly Thr Val Ala Ala
                150                 155                 160 gtc tat gat gta acc ctg aac ttc aga gga aac aag aac ccg tcc ctg      766
Val Tyr Asp Val Thr Leu Asn Phe Arg Gly Asn Lys Asn Pro Ser Leu
                165                 170                 175 ctg ggg atc ctc tac ggg aag aag tac gag gcg gac atg tgc gtg agg      814
Leu Gly Ile Leu Tyr Gly Lys Lys Tyr Glu Ala Asp Met Cys Val Arg
180                 185                 190 aga ttt cct ctg gaa gac atc ccg ctg gat gaa aag gaa gca gct cag      862
Arg Phe Pro Leu Glu Asp Ile Pro Leu Asp Glu Lys Glu Ala Ala Gln
195                 200                 205                 210 tgg ctt cat aaa ctg tac cag gag aag gac gcg ctc cag gag ata tat      910
Trp Leu His Lys Leu Tyr Gln Glu Lys Asp Ala Leu Gln Glu Ile Tyr
                215                 220                 225 aat cag aag ggc atg ttt cca ggg gag cag ttt aag cct gcc cgg agg      958
Asn Gln Lys Gly Met Phe Pro Gly Glu Gln Phe Lys Pro Ala Arg Arg
                230                 235                 240 ccg tgg acc ctc ctg aac ttc ctg tcc tgg gcc acc att ctc ctg tct     1006
Pro Trp Thr Leu Leu Asn Phe Leu Ser Trp Ala Thr Ile Leu Leu Ser
                245                 250                 255 ccc ctc ttc agt ttt gtc ttg ggc gtc ttt gcc agc gga tca cct ctc     1054
Pro Leu Phe Ser Phe Val Leu Gly Val Phe Ala Ser Gly Ser Pro Leu
260                 265                 270 ctg atc ctg act ttc ttg ggg ttt gtg gga gca gct tcc ttt gga gtt     1102
Leu Ile Leu Thr Phe Leu Gly Phe Val Gly Ala Ala Ser Phe Gly Val
275                 280                 285                 290 cgc aga ctg ata gga gta act gag ata gaa aaa ggc tcc agc tac gga     1150
Arg Arg Leu Ile Gly Val Thr Glu Ile Glu Lys Gly Ser Ser Tyr Gly
                295                 300                 305 aac caa gag ttt aag aaa aag gaa taattaatgg ctgtgactga acacacgcgg    1204
Asn Gln Glu Phe Lys Lys Lys Glu
                310 ccctgacggt ggtatccagt taactcaaaa ccaacacaca gagtgcagga aaagacaatt   1264 agaaactatt tttcttatta actggtgact aatattaaca aaacttgagc caagagtaaa   1324 gaattcagaa ggcctgtcag gtgaagtctt cagcctccca cagcgcaggg tcccagcatc   1384 tccacgcgcg cccgtgggag gtgggtccgg ccggagaggc ctcccgcgga cgccgtctct   1444 ccagaactcc gcttccaaga gggacctttg gctgctttct ctccttaaac ttagatcaaa   1504 ttttaaaaaa aaaaaaaaa                                                1523

<210> SEQ ID NO 15
<211> LENGTH: 314
<212> TYPE: PRT
<213> ORGANISM: Homo sapiens
```

<400> SEQUENCE: 15

| | | | | | | | | | | | | | | |
|---|---|---|---|---|---|---|---|---|---|---|---|---|---|---|
|Met|Leu|Leu|Glu|Trp|Trp|Ser|Cys|Thr|Glu|Cys|Thr|Leu|Phe|Thr|Asp|
|1| | | |5| | | |10| | | |15| | |

Met Leu Leu Glu Trp Trp Ser Cys Thr Glu Cys Thr Leu Phe Thr Asp
1               5                   10                  15

Gln Ala Thr Val Glu Arg Phe Gly Lys Glu His Ala Val Ile Ile Leu
            20                  25                  30

Asn His Asn Phe Glu Ile Asp Phe Leu Cys Gly Trp Thr Met Cys Glu
        35                  40                  45

Arg Phe Gly Val Leu Gly Ser Ser Lys Val Leu Ala Lys Lys Glu Leu
    50                  55                  60

Leu Tyr Val Pro Leu Ile Gly Trp Thr Trp Tyr Phe Leu Glu Ile Val
65                  70                  75                  80

Phe Cys Lys Arg Lys Trp Glu Glu Asp Arg Asp Thr Val Val Glu Gly
                85                  90                  95

Leu Arg Arg Leu Ser Asp Tyr Pro Glu Tyr Met Trp Phe Leu Leu Tyr
            100                 105                 110

Cys Glu Gly Thr Arg Phe Thr Glu Thr Lys His Arg Val Ser Met Glu
        115                 120                 125

Val Ala Ala Lys Gly Leu Pro Val Leu Lys Tyr His Leu Leu Pro
    130                 135                 140

Arg Thr Lys Gly Phe Thr Thr Ala Val Lys Cys Leu Arg Gly Thr Val
145                 150                 155                 160

Ala Ala Val Tyr Asp Val Thr Leu Asn Phe Arg Gly Asn Lys Asn Pro
                165                 170                 175

Ser Leu Leu Gly Ile Leu Tyr Gly Lys Lys Tyr Glu Ala Asp Met Cys
            180                 185                 190

Val Arg Arg Phe Pro Leu Glu Asp Ile Pro Leu Asp Glu Lys Glu Ala
        195                 200                 205

Ala Gln Trp Leu His Lys Leu Tyr Gln Glu Lys Asp Ala Leu Gln Glu
    210                 215                 220

Ile Tyr Asn Gln Lys Gly Met Phe Pro Gly Glu Gln Phe Lys Pro Ala
225                 230                 235                 240

Arg Arg Pro Trp Thr Leu Leu Asn Phe Leu Ser Trp Ala Thr Ile Leu
                245                 250                 255

Leu Ser Pro Leu Phe Ser Phe Val Leu Gly Val Phe Ala Ser Gly Ser
            260                 265                 270

Pro Leu Leu Ile Leu Thr Phe Leu Gly Phe Val Gly Ala Ala Ser Phe
        275                 280                 285

Gly Val Arg Arg Leu Ile Gly Val Thr Glu Ile Glu Lys Gly Ser Ser
    290                 295                 300

Tyr Gly Asn Gln Glu Phe Lys Lys Lys Glu
305                 310

<210> SEQ ID NO 16
<211> LENGTH: 1774
<212> TYPE: DNA
<213> ORGANISM: Homo sapiens
<220> FEATURE:
<221> NAME/KEY: CDS
<222> LOCATION: (158)..(1291)

<400> SEQUENCE: 16
tgaacccagc cggctccatc tcagcttctg gtttctaagt ccatgtgcca aaggctgcca      60
ggaaggagac gccttcctga gtcctggatc tttcttcctt ctggaaatct ttgactgtgg     120 ygtagttattt atttctgaat aagagcgtcc acgcatc atg gac ctc gcg gga ctg     175

|  |  |  |  |  | Met<br>1 | Asp | Leu | Ala | Gly<br>5 | Leu |  |  |  |  |  |  | |
|---|---|---|---|---|---|---|---|---|---|---|---|---|---|---|---|---|---|

```
ctg aag tct cag ttc ctg tgc cac ctg gtc ttc tgc tac gtc ttt att       223
Leu Lys Ser Gln Phe Leu Cys His Leu Val Phe Cys Tyr Val Phe Ile
         10                  15                  20 gcc tca ggg cta atc atc aac acc att cag ctc ttc act ctc ctc ctc       271
Ala Ser Gly Leu Ile Ile Asn Thr Ile Gln Leu Phe Thr Leu Leu Leu
     25                  30                  35 tgg ccc att aac aag cag ctc ttc cgg aag atc aac tgc aga ctg tcc       319
Trp Pro Ile Asn Lys Gln Leu Phe Arg Lys Ile Asn Cys Arg Leu Ser
         40                  45                  50 tat tgc atc tca agc cag ctg gtg atg ctg ctg gag tgg tgg tcg ggc       367
Tyr Cys Ile Ser Ser Gln Leu Val Met Leu Leu Glu Trp Trp Ser Gly
 55                  60                  65                  70 acg gaa tgc acc atc ttc acg gac ccg cgc gcc tac ctc aag tat ggg       415
Thr Glu Cys Thr Ile Phe Thr Asp Pro Arg Ala Tyr Leu Lys Tyr Gly
                 75                  80                  85 aag gaa aat gcc atc gtg gtt ctc aac cac aag ttt gaa att gac ttt       463
Lys Glu Asn Ala Ile Val Val Leu Asn His Lys Phe Glu Ile Asp Phe
             90                  95                 100 ctg tgt ggc tgg agc ctg tcc gaa cgc ttt ggg ctg tta ggg ggc tcc       511
Leu Cys Gly Trp Ser Leu Ser Glu Arg Phe Gly Leu Leu Gly Gly Ser
         105                 110                 115 aag gtc ctg gcc aag aaa gag ctg gcc tat gtc cca att atc ggc tgg       559
Lys Val Leu Ala Lys Lys Glu Leu Ala Tyr Val Pro Ile Ile Gly Trp
     120                 125                 130 atg tgg tac ttc acc gag atg gtc ttc tgt tcg cgc aag tgg gag cag       607
Met Trp Tyr Phe Thr Glu Met Val Phe Cys Ser Arg Lys Trp Glu Gln
135                 140                 145                 150 gat cgc aag acg gtt gcc acc agt ttg cag cac ctc cgg gac tac ccc       655
Asp Arg Lys Thr Val Ala Thr Ser Leu Gln His Leu Arg Asp Tyr Pro
                 155                 160                 165 gag aag tat ttt ttc ctg att cac tgt gag ggc aca cgg ttc acg gag       703
Glu Lys Tyr Phe Phe Leu Ile His Cys Glu Gly Thr Arg Phe Thr Glu
             170                 175                 180 aag aag cat gag atc agc atg cag gtg gcc cgg gcc aag ggg ctg cct       751
Lys Lys His Glu Ile Ser Met Gln Val Ala Arg Ala Lys Gly Leu Pro
         185                 190                 195 cgc ctc aag cat cac ctg ttg cca cga acc aag ggc ttc gcc atc acc       799
Arg Leu Lys His His Leu Leu Pro Arg Thr Lys Gly Phe Ala Ile Thr
     200                 205                 210 gtg agg agc ttg aga aat gta gtt tca gct gta tat gac tgt aca ctc       847
Val Arg Ser Leu Arg Asn Val Val Ser Ala Val Tyr Asp Cys Thr Leu
215                 220                 225                 230 aat ttc aga aat aat gaa aat cca aca ctg ctg gga gtc cta aac gga       895
Asn Phe Arg Asn Asn Glu Asn Pro Thr Leu Leu Gly Val Leu Asn Gly
                 235                 240                 245 aag aaa tac cat gca gat ttg tat gtt agg agg atc cca ctg gaa gac       943
Lys Lys Tyr His Ala Asp Leu Tyr Val Arg Arg Ile Pro Leu Glu Asp
             250                 255                 260 atc cct gaa gac gat gac gag tgc tcg gcc tgg ctg cac aag ctc tac       991
Ile Pro Glu Asp Asp Asp Glu Cys Ser Ala Trp Leu His Lys Leu Tyr
         265                 270                 275 cag gag aag gat gcc ttt cag gag gag tac tac agg acg ggc acc ttc      1039
Gln Glu Lys Asp Ala Phe Gln Glu Glu Tyr Tyr Arg Thr Gly Thr Phe
     280                 285                 290 cca gag acg ccc atg gtg ccc ccc cgg cgg ccc tgg acc ctc gtg aac      1087
Pro Glu Thr Pro Met Val Pro Pro Arg Arg Pro Trp Thr Leu Val Asn
295                 300                 305                 310
```

```
tgg ctg ttt tgg gcc tcg ctg gtg ctc tac cct ttc ttc cag ttc ctg      1135
Trp Leu Phe Trp Ala Ser Leu Val Leu Tyr Pro Phe Phe Gln Phe Leu
                315                 320                 325 gtc agc atg atc agg agc ggg tct tcc ctg acg ctg gcc agc ttc atc      1183
Val Ser Met Ile Arg Ser Gly Ser Ser Leu Thr Leu Ala Ser Phe Ile
            330                 335                 340 ctc gtc ttc ttt gtg gcc tcc gtg gga gtt cga tgg atg att ggt gtg      1231
Leu Val Phe Phe Val Ala Ser Val Gly Val Arg Trp Met Ile Gly Val
        345                 350                 355 acg gaa att gac aag ggc tct gcc tac ggc aac tct gac agc aag cag      1279
Thr Glu Ile Asp Lys Gly Ser Ala Tyr Gly Asn Ser Asp Ser Lys Gln
    360                 365                 370 aaa ctg aat gac tgactcaggg aggtgtcacc atccgaaggg aaccttgggg          1331
Lys Leu Asn Asp
375 aactggtggc tctgcatat cctccttagt gggacacggt gacaaaggct gggtgagccc     1391 ctgctgggca cggcgaagt cacgacctct ccagccaggg agtctggtct caaggccgga     1451 tggggaggaa gatgttttgt aatctttttt tccccatgtg ctttagtggg ctttggtttt    1511 cttttttgtgc gagtgtgtgt gagaatggct gtgtggtgag tgtgaacttt gttctgtgat   1571 catagaaagg gtattttagg ctgcagggga gggcagggct ggggaccgaa ggggacaagt    1631 tcccctttca tcctttggtg ctgagttttc tgtaaccctt ggttgccaga gataaagtga    1691 aaagtgcttt aggtgagatg actaaattat gcctccaaga aaaaaaaatt aaagtgcttt    1751 tctgggtcaa aaaaaaaaaa aaa                                            1774

<210> SEQ ID NO 17
<211> LENGTH: 378
<212> TYPE: PRT
<213> ORGANISM: Homo sapiens

<400> SEQUENCE: 17

Met Asp Leu Ala Gly Leu Leu Lys Ser Gln Phe Leu Cys His Leu Val
 1               5                  10                  15

Phe Cys Tyr Val Phe Ile Ala Ser Gly Leu Ile Ile Asn Thr Ile Gln
            20                  25                  30

Leu Phe Thr Leu Leu Leu Trp Pro Ile Asn Lys Gln Leu Phe Arg Lys
        35                  40                  45

Ile Asn Cys Arg Leu Ser Tyr Cys Ile Ser Ser Gln Leu Val Met Leu
    50                  55                  60

Leu Glu Trp Trp Ser Gly Thr Glu Cys Thr Ile Phe Thr Asp Pro Arg
65                  70                  75                  80

Ala Tyr Leu Lys Tyr Gly Lys Glu Asn Ala Ile Val Val Leu Asn His
                85                  90                  95

Lys Phe Glu Ile Asp Phe Leu Cys Gly Trp Ser Leu Ser Glu Arg Phe
            100                 105                 110

Gly Leu Leu Gly Gly Ser Lys Val Leu Ala Lys Glu Leu Ala Tyr
        115                 120                 125

Val Pro Ile Ile Gly Trp Met Trp Tyr Phe Thr Glu Met Val Phe Cys
    130                 135                 140

Ser Arg Lys Trp Glu Gln Asp Arg Lys Thr Val Ala Thr Ser Leu Gln
145                 150                 155                 160

His Leu Arg Asp Tyr Pro Glu Lys Tyr Phe Phe Leu Ile His Cys Glu
                165                 170                 175

Gly Thr Arg Phe Thr Glu Lys Lys His Glu Ile Ser Met Gln Val Ala
            180                 185                 190
```

-continued

```
Arg Ala Lys Gly Leu Pro Arg Leu Lys His His Leu Leu Pro Arg Thr
            195                 200                 205

Lys Gly Phe Ala Ile Thr Val Arg Ser Leu Arg Asn Val Val Ser Ala
210                 215                 220

Val Tyr Asp Cys Thr Leu Asn Phe Arg Asn Asn Glu Asn Pro Thr Leu
225                 230                 235                 240

Leu Gly Val Leu Asn Gly Lys Lys Tyr His Ala Asp Leu Tyr Val Arg
                245                 250                 255

Arg Ile Pro Leu Glu Asp Ile Pro Glu Asp Asp Glu Cys Ser Ala
            260                 265                 270

Trp Leu His Lys Leu Tyr Gln Glu Lys Asp Ala Phe Gln Glu Glu Tyr
            275                 280                 285

Tyr Arg Thr Gly Thr Phe Pro Glu Thr Pro Met Val Pro Pro Arg Arg
            290                 295                 300

Pro Trp Thr Leu Val Asn Trp Leu Phe Trp Ala Ser Leu Val Leu Tyr
305                 310                 315                 320

Pro Phe Phe Gln Phe Leu Val Ser Met Ile Arg Ser Gly Ser Ser Leu
                325                 330                 335

Thr Leu Ala Ser Phe Ile Leu Val Phe Phe Val Ala Ser Val Gly Val
                340                 345                 350

Arg Trp Met Ile Gly Val Thr Glu Ile Asp Lys Gly Ser Ala Tyr Gly
            355                 360                 365

Asn Ser Asp Ser Lys Gln Lys Leu Asn Asp
    370                 375
```

<210> SEQ ID NO 18
<211> LENGTH: 52
<212> TYPE: PRT
<213> ORGANISM: Saccharomyces cerevisiae

<400> SEQUENCE: 18

```
Pro Phe Lys Lys Gly Ala Phe His Leu Ala Gln Gln Gly Lys Ile Pro
1               5                   10                  15

Ile Val Pro Val Val Ser Asn Thr Ser Thr Leu Val Ser Pro Lys
            20                  25                  30

Tyr Gly Val Phe Asn Arg Gly Cys Met Ile Val Arg Ile Leu Lys Pro
        35                  40                  45

Ile Ser Thr Glu
    50
```

<210> SEQ ID NO 19
<211> LENGTH: 52
<212> TYPE: PRT
<213> ORGANISM: Homo sapiens

<400> SEQUENCE: 19

```
Pro Ser Asn Cys Gly Ala Phe His Leu Ala Val Gln Ala Gln Val Pro
1               5                   10                  15

Ile Val Pro Ile Val Met Ser Ser Tyr Gln Asp Phe Tyr Cys Lys Lys
            20                  25                  30

Glu Arg Arg Phe Thr Ser Gly Gln Cys Gln Val Arg Val Leu Pro Pro
        35                  40                  45

Val Pro Thr Glu
    50
```

<210> SEQ ID NO 20

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcaagatgg aaggcgcc                                                   18

<210> SEQ ID NO 21
<211> LENGTH: 6
<212> TYPE: PRT
<213> ORGANISM: Homo sapiens

<400> SEQUENCE: 21

Gly Ala Phe His Leu Ala
 1               5

<210> SEQ ID NO 22
<211> LENGTH: 60
<212> TYPE: PRT
<213> ORGANISM: Saccharomyces cerevisiae

<400> SEQUENCE: 22

Gln Gln Gly Lys Ile Pro Ile Val Pro Val Val Ser Asn Thr Ser
 1               5                  10                  15

Thr Leu Val Ser Pro Lys Tyr Gly Val Phe Asn Arg Gly Cys Met Ile
                20                  25                  30

Val Arg Ile Leu Lys Pro Ile Ser Thr Glu Asn Leu Thr Lys Asp Lys
            35                  40                  45

Ile Gly Glu Phe Ala Glu Lys Val Arg Asp Gln Met
        50                  55                  60

<210> SEQ ID NO 23
<211> LENGTH: 60
<212> TYPE: PRT
<213> ORGANISM: Homo sapiens

<400> SEQUENCE: 23

Val Arg Glu Asn Val Pro Ile Val Pro Val Val Tyr Ser Ser Phe Ser
 1               5                  10                  15

Ser Phe Tyr Asn Thr Lys Lys Lys Phe Phe Thr Ser Gly Thr Val Thr
                20                  25                  30

Val Gln Val Leu Glu Ala Ile Pro Thr Ser Gly Leu Thr Ala Ala Asp
            35                  40                  45

Val Pro Ala Leu Arg Gly Thr Pro Ala Thr Gly Pro
        50                  55                  60

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cctcaaagtg tggatctatc                                                 20

<210> SEQ ID NO 25
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 25
ggaagagtac accacgggga c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
gactctagcc taggcttttg c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 27
ctagcttata atacgactca c                                              21

<210> SEQ ID NO 28
<211> LENGTH: 23
<212> TYPE: PRT
<213> ORGANISM: Zea mays

<400> SEQUENCE: 28

Gly Leu Gln Arg Leu Lys Asp Phe Pro Arg Pro Phe Trp Leu Ala Leu
 1               5                  10                  15

Phe Val Glu Gly Thr Arg Phe
             20

<210> SEQ ID NO 29
<211> LENGTH: 23
<212> TYPE: PRT
<213> ORGANISM: Homo sapiens

<400> SEQUENCE: 29

Gly Leu Arg Arg Leu Ser Asp Tyr Pro Glu Tyr Met Trp Phe Leu Leu
 1               5                  10                  15

Tyr Cys Glu Gly Thr Arg Phe
             20

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gactaccccg agtacatgtg gtttctc                                        27

<210> SEQ ID NO 31
<211> LENGTH: 9
<212> TYPE: PRT
<213> ORGANISM: Homo sapiens

```
<400> SEQUENCE: 31

Asp Tyr Pro Glu Tyr Met Trp Phe Leu
 1               5

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cacatgtccg cctcgtactt cttc                                            24

<210> SEQ ID NO 33
<211> LENGTH: 46
<212> TYPE: PRT
<213> ORGANISM: Homo sapiens

<400> SEQUENCE: 33

Met Gly Leu Leu Ala Phe Leu Lys Thr Gln Phe Val Leu His Leu Leu
 1               5                  10                  15

Val Gly Phe Val Phe Val Val Ser Gly Leu Val Ile Asn Phe Val Gln
                20                  25                  30

Leu Cys Thr Leu Ala Leu Trp Pro Val Ser Lys Gln Leu Tyr
            35                  40                  45

<210> SEQ ID NO 34
<211> LENGTH: 46
<212> TYPE: PRT
<213> ORGANISM: Homo sapiens

<400> SEQUENCE: 34

Met Asp Leu Ala Gly Leu Leu Lys Ser Gln Phe Leu Cys His Leu Val
 1               5                  10                  15

Phe Cys Tyr Val Phe Ile Ala Ser Gly Leu Ile Ile Asn Thr Ile Gln
                20                  25                  30

Leu Phe Thr Leu Leu Leu Trp Pro Ile Asn Lys Gln Leu Phe
            35                  40                  45

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 35
ggctctagat attaatagta atcaattac                                       29

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 36
cctcacgcat gcaccatggt aatagc                                          26

<210> SEQ ID NO 37
```

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 37
ggtgcatgcg tgaggctccg gtgc                                              24

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 38
gtagttttca cggtacctga aatggaag                                          28

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 39
ggcccggtac catgggcctg ctggccttcc                                        30

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
taactcctcg agttattcct ttttcttaaa ctc                                    33

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 41
atggtggtac caccatggac ctcgcgggac tgctg                                  35

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 42
ggaggatatc tagaggccac cagttc                                            26

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag
```

```
<400> SEQUENCE: 43

His His His His His His
  1               5

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cacatgtccg cctcgtactt cttc                                          24

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
gactctagcc taggcttttg c                                             21
```